United States Patent
Hamilton et al.

(10) Patent No.: US 9,528,116 B2
(45) Date of Patent: Dec. 27, 2016

(54) **METHOD FOR PRODUCING THERAPEUTIC PROTEINS IN *PICHIA PASTORIS* LACKING DIPEPTIDYL AMINOPEPTIDASE ACTIVITY**

(75) Inventors: Stephen R. Hamilton, Enfield, NH (US); Terrance A. Stadheim, Lyme, NH (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 252 days.

(21) Appl. No.: 13/503,663

(22) PCT Filed: Oct. 27, 2010

(86) PCT No.: PCT/US2010/054183
§ 371 (c)(1),
(2), (4) Date: May 31, 2012

(87) PCT Pub. No.: WO2011/053612
PCT Pub. Date: May 5, 2011

(65) Prior Publication Data
US 2012/0231502 A1 Sep. 13, 2012

Related U.S. Application Data

(60) Provisional application No. 61/256,369, filed on Oct. 30, 2009.

(51) Int. Cl.
| | | |
|---|---|---|
| *C07K 16/00* | (2006.01) | |
| *C12N 15/81* | (2006.01) | |
| *C12N 9/48* | (2006.01) | |
| *C12P 21/00* | (2006.01) | |
| *C12P 21/02* | (2006.01) | |

(52) U.S. Cl.
CPC ............... *C12N 15/81* (2013.01); *C12N 9/48* (2013.01); *C12P 21/005* (2013.01); *C12P 21/02* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 2005/0124036 A1* | 6/2005 | Susilo et al. | 435/69.1 |
| 2006/0110747 A1* | 5/2006 | Ramseier et al. | 435/6 |
| 2006/0121565 A1* | 6/2006 | Jonson et al. | 435/69.1 |
| 2006/0286637 A1* | 12/2006 | Hamilton | 435/69.1 |

FOREIGN PATENT DOCUMENTS

WO  WO 2007148345 A2 * 12/2007

OTHER PUBLICATIONS

Prabha et al. Protein Expression and Purification 64 (2009) 155-161.*
Prabha L, Govindappa N, Adhikary L, Melarkode R, Sastry K. Identification of the dipeptidyl aminopeptidase responsible for N-terminal clipping of recombinant Exendin-4 precursor expressed in Pichia pastoris. Protein Expr Purif. Apr. 2009;64(2):155-61. Epub Nov. 8, 2008.
Hamilton SR, Bobrowicz P, Bobrowicz B, Davidson RC, Li H, Mitchell T, Nett JH, Rausch S, Stadheim TA, Wischnewski H, Wildt S, Gerngross TU. Production of complex human glycoproteins in yeast. Science. Aug. 29, 2003;301(5637):1244-6.
Li H, Sethuraman N, Stadheim TA, Zha D, Prinz B, Ballew N, Bobrowicz P, Choi BK, Cook WJ, Cukan M, Houston-Cummings NR, Davidson R, Gong B, Hamilton SR, Hoopes JP, Jiang Y, Kim N, Mansfield R, Nett JH, Rios S, Strawbridge R, Wildt S, Gerngross TU. Optimization of humanized IgGs in glycoengineered Pichia pastoris. Nat Biotechnol. Feb. 2006;24(2):210-5. Epub Jan. 22, 2006.
Bobrowicz P, Davidson RC, Li H, Potgieter TI, Nett JH, Hamilton SR, Stadheim TA, Miele RG, Bobrowicz B, Mitchell T, Rausch S, Renfer E, Wildt S. Engineering of an artificial glycosylation pathway blocked in core oligosaccharide assembly in the yeast *Pichia pastoris*: production of complex humanized glycoproteins with terminal galactose. Glycobiology. Sep. 2004;14(9):757-66. Epub Jun. 9, 2004.
Daniel Hopkins, "Elimination of diaminopeptidase activity in Pichia pastoris for therapeutic protein production", *Applied Genetics and Molecular Biotechnology* (2014) 98: 2573-2583.
Hopkins et al., Elimination of diaminopeptidase activity in Pichia pastoris for therapeutic protein production, Appl. Microbiol. Biotechnol, (2014), 98:2573-2583.

* cited by examiner

*Primary Examiner* — Jeanette Lieb

(57) ABSTRACT

The present invention related to methods and compositions for producing therapeutic proteins in yeast cell lines, and in particular *Pichia pastoris*, lacking dipeptidyl aminopeptidase (DAP) activity. DAP activity has been eliminated by genetically modifying a *Pichia pastoris* cell line such that STE13 and DAP2 have been deleted.

12 Claims, 24 Drawing Sheets

↓
LPAQVAF (SEQ ID NO: 1)

FIG.2A

AQVAF (SEQ ID NO: 2)

FIG.2B

TNFRII-Fc (SEQ ID NO:3)

LPAQVAFTPYAPEPGSTCRLREYYDQTAQMCCSKCSPGQHAKVFCTKTSDTV
CDSCEDSTYTQLWNWVPECLSCGSRCSSDQVETQACTREQNRICTCRPGWYC
ALSKQEGCRLCAPLRKCRPGFGVARPGTETSDVVCKPCAPGTFSNTTSSTDIC
RPHQICNVVAIPGNASMDAVCTSTSPTRSMAPGAVHLPQPVSTRSQHTQPTPE
PSTAPSTSFLLPMGPSPPAEGSTGDEPKSCDKTHTCPPCPAPELLGGPSVFLFPP
KPKDTLMISRTPEVTCVVVDVSHEDPVKFNWYVDGVEVHNAKTKPREEQYN
STYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDG
SFFLYSKLTVDKSRWQQGNVFSCSVMHEALHNHYTQKSLSLSPGK

FIG.3

↓
TPLGPAS (SEQ ID NO:4)

FIG.4A

LGPAS (SEQ ID NO:5)

FIG.4B

GCSF (SEQ ID NO:6)

TPLGPASSLPQSFLLCLEQVRKIQGDGAALQEKLCATYKLCHPEELVLLGHS
LGIPWAPLSSCPSQALQLAGCLSQLHSGLFLYQGLLQALEGISPELGPTLDTLQ
LDVADFATTIWQQMEELGMAPALQPTQGAMPAFASAFQRRAGGVLVASHLQ
SFLEVSYRVLRHLAQP

FIG.5

Pichia pastoris DAP2 gene sequence (SEQ ID NO: 37):

```
GTGAAGTAGATAGCTTTGTTGTTGGAGTGAGCGATGGCAATACCAAACTC
GTTACGTTTAGCAAACTCTTTCACAAACTGGCGCAATTCAGTAACGTCATC
GAATTCCTTCTCTTGGATCCATGGCGTCACAAAAACTGCTTCATCGTCCTC
AGGTAGAATTGGAATATCCTTAGGTCCTCCTGGGGTGGCAGGAATAACAT
AGTGTTGCACGTGACTGGGAACTCTCATAGTGTTTACATGGCTATGACCGT
GAAGGACATGCTGATGGCTTGCCGCAGTCGGTTGATGGTGATACTCGATG
TTTAAGTGTGACAAATCGTTACTGGCAGCTGCTGTGTACTTCGGTATAAGA
TGCTGGATCTTTGCCTCGGCACTTTCATCCTGAGGATCTTGGTCCTGACCG
GGCTGGTGGTGGTCAATGTGAACCTGGGCCTGTTGCTGCTGGTACTGCTGT
TGGAACTGTTGGTATTGTTGCTGATCTAAGGCCGCCTGTTCCACACCGTGT
GTATCGAATGCTTGGGCAAAATCATCGCCTGCCGGAGGCCCCACTACCGC
TTGTTCCTCCTGCTCTTGTTTGTTTTGCTCATTGATGATATCGGCGTCAATG
AATTGATCCTCAATCGTGTGGTGGTGGTGTCGTGA1CCTCTTCTTTCTTGA
GTGCCTTATCCATATTCCTATCTTAGTGTACCAATAATTTTGTTAAACACA
CGCTGTTG1TTATGAAAAGTCGTCAAAAGGTTAAAAATTCTACTTGGTGTG
TGTCAGAGAAAGTAGTGCAGACCCCCAGTTTGTTGACTAGTTGAGAAGGC
GGCTCACTATTGCGCGAATAGCATGAGAAATTTGCAAACATCTGGCAAAG
TGGTCAATACCTGCCAACCTGCCAATCTTCGCGACGGAGGCTGTTAAGCG
GGTTGGGTTCCCAAAGTGAATGGATATTACGGGCAGGAAAAACAGCCCCT
TCCACACTAGTCTTTGCTACTGACATCTTCCCTCTCATGTATCCCGAACAC
AAGTATCGGGAGTATCAACGGAGGGTGCCCTTATGGCAGTACTCCCT
GTTGGTGATTGTACTGCTATACGGGTCTCATTTGCTTATCAGCACCAT
CAACTTGATACACTATAACCACAAAAATTATCATGCACACCCAGTCAA
TAGTGGTATCGTTCTTAATGAGTTTGCTGATGACGATTCATTCTCTTT
GAATGGCACTCTGAACTTGGAGAACTGGAGAAATGGTACCTTTTCCC
CTAAATTTCATTCCATTCAGTGGACCGAAATAGGTCAGGAAGATGACC
AGGGATATTACATTCTCTCTTCCAATTCCTCTTACATAGTAAAGTCTTT
ATCCGACCCAGACTTTGAATCTGTTCTATTCAACGAGTCTACAATCAC
TTACAACGGTGAAGAACATCATGTGGAAGACGTCATAGTGTCCAATA
ATCTTCAATATGCATTGGTAGTTACGGATAAGAGACATAATTGGCGCC
ATTCTTTTTTTTGCGAATTACTGGCTGTATAAAGTCAACAATCCTGAAC
AGGTTCAGCCTTTGTTTGATACAGATCTATCGTTGAATGGTCTTATTA
GCCTTGTCCATTGGTCTCCGGATTCTTCCCAAGTTGCATTTGTGTTGG
AAAATAACATATATTTGAAGCATCTTAACAACTTTTCTGATTCAAGGA
TTGATCAACTAACTTATGATGGAGGCGAAAACATATTTTATGGCAAAC
CAGATTGGGTTTATGAAGAAGAAGTGTTTGAAAGCAACTCTGCTATGT
GGTGGTCTCCAAATGGAAAGTTTTTATCAATATTGCGAACTAATGACA
```

FIG.8A-1

```
CCCAAGTGCCTGTCTATCCTATTCCATATTTTGTTCAGTCTGATGCTG
AAACAGCTATCGATGAATACCCTCTTCTGAAACACATAAAATACCCAA
AGGCAGGATTTTCCCAATCCAGTTGTTGATGTGATTGTATACGATGTTC
AACGCCAGCACATATCTAGGTTACCTGCTGGTGATCCTTTCTACAACG
ATGAGAACATTACCAATGAGGACAGACTTATCACTGAGATCATCTGG
GTTGGTGATTCACGGTTCCTGACCAAGATTACGAACAGGGAAAGTGA
CTTGTTAGCATTTTATCTGGTAGACGCTGAGGCTAACAATAGTAAGCT
GGTAAGATTCCAAGATGCTAAGAGCACCAAGTCTTGGTTTGAAATTGA
ACACAACACATTGTATATTCCTAAGGATACTTCAGTGGGAAGGGCACA
AGATGGCTACATCGACACCATAGATGTTAACGGCTACAACCATTTAGC
CTATTTCTCACCACCAGACAACCCAGACCCCAAGGTCATTCTTACGCG
TGGTGATTGGGAAGTCGTTGACAGTCCATCTGCATTTGACTTCAAAAG
AAATTTGGTTTACTTTACAGCAACCAAGAAATCCTCAATAGAAAGACA
TGTTTATTGTGTTGGGATAGACGGGAAACAATTCAACAATGTAACTGA
TGTTTCATCAGATGGATACTACAGTACAAGCTTTTCCCCTGGAGCAAG
ATATGTATTGCTATCACACCAAGGTCCCCGTGTACCTTATCAAAAGAT
GATAGATCTTGTCAAAGGCACCGAAGAAATAATCGAATCTAACGAAG
ATTTGAAAGACTCCGTTGCTTTATTTGATTTACCTGATGTCAAGTACG
GCGAAATCGAGCTTGAAAAAGGTGTCAAGTCAAACTACGTTGAGATC
AGGCCTAAGAACTTCGATGAAAGCAAAAAGTATCCGGTTTTATTTTTT
GTGTATGGGGGGCCAGGTTCCCAATTGGTAACAAAGACATTTTCTAA
GAGTTTCCAGCATGTTGTATCCTCTGAGCTTGACGTCATTGTTGTCAC
GGTGGATGGAAGAGGGACTGGATTTAAAGGTAGAAAATATAGATCCA
TAGTGCGGGACAACTTGGGTCATTATGAATCCCTGGACCAAATCACG
GCAGGAAAAATTTGGGCAGCAAAGCCTTACGTTGATGAGAATAGACT
GGCCATTTGGGGTTGGTCTTATGGAGGTTACATGACGCTAAAGGTTTT
AGAACAGGATAAAGGTGAAACATTCAAATATGGAATGTCTGTTGCCC
CTGTGACGAATTGGAAATTCTATGATTCTATCTACACAGAAAGATACA
TGCACACTCCTCAGGACAATCCAAACTATTATAATTCGTCAATCCATG
AGATTGATAATTTGAAGGGAGTGAAGAGGTTCTTGCTAATGCACGGA
ACTGGTGACGACAATGTTCACTTCCAAAATACACTCAAAGTTCTAGAT
TTATTTGATTTACATGGTCTTGAAAACTATGATATCCACGTGTTCCCT
GATAGTGATCACAGTATTAGATATCACAACGGTAATGTTATAGTGTAT
GATAAGCTATTCCATTGGATTAGGCGTGCATTCAAGGCTGGCAAATAA
ATAGGTGCAAAAATATTATTAGACTTTTTTTT CGTTCGCAAGTTATTACT
GTGTACCATACCGATCCAATCCGTATTGTAAT CATGTTCTAGATCCAAAA
TTTGGGACTCTAATTCATGAGGTCTAGGAAGA GATCATCTCTATAGTTTT
CAGCGGGGGGCTCGATTTGCGGTTGGTCAAAGCTAACATCAAAATGTTTG
TCAGGTTCAGTGAATGGTAACTGCTGCTCTTGAATTGGTCGTCTGACAAAT
```

FIG.8A-2

```
TCTCTAAGTGATAGCACTTCATCTACAATCATTTGCTTCATCGTTTCTATAT
CGTCCACGACCTCAAACGAGAAATCGAATTTGGAAGAACAGACGGGCTCA
TCGTTAGGATCATGCCAAACCTTGAGATATGGATGCTCTAAAGCCTCAGT
AACTGTAATTCTGTGAGTGGGATCTACCGTGAGCATTCGATCCAGTAAGTC
TATCGCTTCAGGGTTGGCACCGGGAAATAACTGGCTGAATGGGATCTTGG
GCATGAATGGCAGGGAGCGAACATAATCCTGGGCACGCTCTGATCTGATA
GACTGAAGTGTCTCTTCCGAAACAGTACCCAGCGTACTCAAAATCAAGTT
CAATTGATCCACATAGTCTCTTCCTCTAAAAATGGGTGGGCCACCTAAGAG
TTCGGCCAATATACATCCAACTGACCAGATATCAATTGCTTTGGTATATGT
CTGAAAACTAAGAATTATCTCCGGTGCCCGATACCACCTGGTAGCAACAT
ATTCCGTAAGAAAGCCAGCATTCTTCTCTGCATCACTACTATAACCTCTTG
CAAGTCCAAAGTCACAAATCTTAAGTTCGCAATCTGAGTTCACCAATAGA
TTGACGGGTTTAAGATCTCTATGCAGCACATCTGCTGAATGGATATACTTT
AAGCCCCCGAGAATTTGGTAGATAAAGCTCTGATAGTGGCTGTCAGTCAA
AGGTTGTTTTGATTTGATTATATGATGCAAGTCACATTCCATCAATTCTTC
```

FIG.8A-3

Pichia pastoris DAP2 Protein sequence (SEQ ID NO: 38):

Pichia pastoris STE13 DNA sequence (SEQ ID NO: 39):

GACATTGCTAGTTGCAGTATTCAACGAATCATCAGATATCAGGCTCAGGT
CATTATATGAGGCCTCTGTCTCTATTTTCAGTAGCTCTTTAGGGGATATTTG
ATTAAGAAAACCATCCAAAAGTAGGGATTGCATGGGCCTTGTGGGGTTCT
AGGTAAAGAATTAGAAATTACTCACCGCGATTCTAGGGCTCCTAGATAGT
GAATGAAGAGGCAGGACAGAACTTCAAGAAGAAGAGCAGAAAGATGTTC
GATAGGTTCCAAGGAGGTTTAATCTACTTTTACAGTTGCTGTTTAGCATTA
CTCAAAGTTCCGTGTCGGTGGAGGGTCAACTAATTGTATTATCTAGTACGT
TACCAAGCACTAACTGTTTTGCCAAACGTTACCAGTTTTCTCTCTAACGAC
GGATCAGTATATACAAGTTATCTTGCTTCAAAGAAGCAAGGGACTTGTAG
CCACCCTCAAGGCACATTAAAAGTCCGCCAAAGGAAACGTACACTTTTAT
TTTATCCTCATCTCCTTCCTCAAACTTATAAACAGTCCCAAACATAACGTA
ATCGTAGTCGTCAGCCAAAGATTTGTCAGTTGGCTTTGGGGGCCTCCAGG
ACTTGCTGAAATTTGCTGACTCATCTTCGCCATCCAAGGATAATGAGTTAG
CTAATGTGACAGTTAATGAGTCGTCTTGACTAACGGGGAACATTTCATTAT
TTATATCCAGAGTCAATTTGATAGCAGAGTTTGTGGTTGAAATACCTATGA
TTCGGGAGACTTTGTTGTAACGACCATTATCCACAGTTTGGACCGTGAAAA
TGTCATCGAAGAGAGCAGACGACATATTATCTATTGTGGTAAGTGATAGT
TGGAAGTCCGACTAAGGCATGAAAATGAGAAGACTGAAAATTTAAAGTTT
TTGAAAACACTAATCGGGTAATAACTTGGAAATTACGTTTACGTGCCTTTA
GCTCTTGTCCTTACCCCTGATAATCTATCCATTTCCGAGAGACAATGACA
TCTCGGACAGCTGAGAACCCGTTCGATATAGAGCTTCAAGAGAATCT
AAGTCCACGTTCTTCCAATTCGTCCATATTGGAAAACATTAATGAGTA
TGCTAGAAGACATCGCAATGATTCGCTTTCCCAAGAATGTGATAATGA
AGATGAGAACGAAAATCTCAATTATACTGATAACTTGGCCAAGTTTTC
AAAGTCTGGAGTATCAAGAAAGAGCTGTATGCTAATATTTGGTATTTG
CTTTGTTATCTGGCTGTTTCTCTTTGCCTTGTATGCGAGGGACAATCG
ATTTTCCAATTTGAACGAGTACGTTCCAGATTCAAACAGCCACGGAAC
TGCTTCTGCCACCACGTCTATCGTTGAACCAAAACAGACTGAATTACC
TGAAAGCAAAGATTCTAACACTGATTATCAAAAAGGAGCTAAATTGAG
CCTTAGCGGCTGGAGATCAGGTCTGTACAATGTCTATCCAAAACTGAT
CTCTCGTGGTGAAGATGACATATACTATGAACACAGTTTTCATCGTAT
AGATGAAAAGAGGATTACAGACTCTCAACACGGTCGAACTGTATTTAA
CTATGAGAAAATTGAAGTAAATGGAATCACGTATACAGTGTCATTTGT
CACCATTTCTCCTTACGATTCTGCCAAATTCTTAGTCGCATGCGACTA
TGAAAAACACTGGAGACATTCTACGTTTGCAAAATATTTCATATATGA
TAAGGAAAGCGACCAAGAGGATAGCTTTGTACCTGTCTACGATGACA
AGGCATTGAGCTTCGTTGAATGGTCGCCCTCAGGTGATCATGTAGTAT

FIG.9A-1

```
TCGTTTTTGAAAACAATGTATACCTCAAACAACTCTCAACTTTAGAGG
TTAAGCAGGTAACTTTTGATGGTGATGAGAGTATTTACAATGGTAAGC
CTGACTGGATCTATGAAGAGGAAGTTTTAAGTAGCGACAGAGCCATA
TGGTGGAATGACGATGGATCGTACTTTACGTTCTTGAGACTTGATGAC
AGCAATGTCCCAACCTTCAACTTGCAGCATTTTTTTGAAGAAACAGGC
TCTGTGTCGAAATATCCGGTCATTGATCGATTGAAATATCCAAAACCA
GGATTTGACAACCCCCTGGTTTCTTTGTTTAGTTACAACGTTGCCAAG
CAAAAGTTAGAAAAGCTAAATATTGGAGCAGCAGTTTCTTTGGGAGA
AGACTTCGTGCTTTACAGTTTAAAATGGATAGACAATTCTTTTTTCTT
GTCGAAGTTCACAGACCGCACTTCGAAAAAAATGGAAGTTACTCTAGT
GGACATTGAAGCCAATTCTGCTTCGGTGGTGAGAAAACATGATGCAA
CTGAGTATAACGGCTGGTTCACTGGAGAATTTTCTGTTTATCCTGTCG
TTGGAGATACCATTGGTTACATTGATGTAATCTATTATGAGGACTACG
ATCACTTGGCTTATTATCCAGACTGCACATCCGATAAGTATATTGTGC
TTACAGATGGTTCATGGAATGTTGTTGGACCTGGAGTTTTAGAAGTGC
TTGAAGATAGAGTCTACTTTATCGGCACCAAAGAATCATCAATGGAAC
ATCACTTGTATTATACATCATTAACGGGACCCAAGGTTAAGGCTGTTA
TGGATATCAAAGAACCTGGGTACTTTGATGTAAACATTAAGGGAAAAT
ATGCTTTACTATCTTACAGAGGCCCCAAACTCCCATACCAGAAATTTA
TTGATCTTTCTGACCCTAGTACAACAAGTCTTGATGACATTTTATCGT
CTAATAGAGGAATTGTCGAGGTTAGTTTAGCAACTCACAGCGTTCCTG
TTTCTACCTATACTAATGTAACACTTGAGGACGGCGTCACACTGAACA
TGATTGAAGTGTTGCCTGCCAATTTTAATCCTAGCAAGAAGTACCCAC
TGTTGGTCAACATTTATGGTGGACCGGGCTCCCAGAAGTTAGATGTG
CAGTTCAACATTGGGTTTGAGCATATTATTTCTTCGTCACTGGATGCA
ATAGTGCTTTACATAGATCCGAGAGGTACTGGAGGTAAAAGCTGGGC
TTTTAAATCTTACGCTACAGAGAAAATAGGCTACTGGGAACCACGAGA
CATCACTGCAGTAGTTTCCAAGTGGATTTCAGATCACTCATTTGTGAA
TCCTGACAAAACTGCGATATGGGGGTGGTCTTACGGTGGGTTCACTA
CGCTTAAGACATTGGAATATGATTCTGGAGAGGTTTTCAAATATGGTA
TGGCTGTTGCTCCAGTAACTAATTGGCTTTTGTATGACTCCATCTACA
CTGAAAGATACATGAACCTTCCAAAGGACAATGTTGAAGGCTACAGT
GAACACAGCGTCATTAAGAAGGTTTCCAATTTTAAGAATGTAAACCGA
TTCTTGGTTTGTCACGGGACTACTGATGATAACGTGCATTTTCAGAAC
ACACTAACCTTACTGGACCAGTTCAATATTAATGGTGTTGTGAATTAC
GATCTTCAGGTGTATCCCGACAGTGAACATAGCATTGCCCATCACAAC
GCAAATAAAGTGATCTACGAGAGGTTATTCAAGTGGTTAGAGCGGGC
ATTTAACGATAGATTTTTGTAACATTCCGTACTTCATGCCATACTATATA
```

FIG.9A-2

```
TCCTGCAAGGTTTCCCTTTCAGACACAATAATTGCTTTGCAATTTTACATA
CCACCAATTGGCAAAAATAATCTCTTCAGTAAGTTGAATGCTTTTCAAGCC
AGCACCGTGAGAAATTGCTACAGCGCGCATTCTAACATCACTTTAAAATT
CCCTCGCCGGTGCTCACTGGAGTTTCCAACCCTTAGCTTATCAAAATCGGG
TGATAACTCTGAGTTTTTTTTTTCACTTCTATTCCTAAACCTTCGCCCAATG
CTACCACCTCCAATCAACATCCCGAAATGGATAGAAGAGAATGGACATCT
CTTGCAACCTCCGGTTAATAATTACTGTCTCCACAGAGGAGGATTTACGGT
AATGATTGTAGGTGGGCCTAATGAGAGAACCGATTATCATGTTAATCAGA
CACCTGAATACTTCTATCAATACAAGGGCCACATGTGTCTTAAAGTCGTGG
ATGATGGTGAATTTAAGGACATTATTATCAATGAAGGAGAATCGTTTTTGC
TACCAGGTAATACGCCACATAGTCCAGTGAGGTTTGCTGATACTATTGGCT
TAGTGGTTGAACAGGATCGTCCTCAGGGACTGAATGACCGTATTAGATGG
TATTGTCTGAATTGCAAGGAAATAGTGCATGAAACTGAGTTTTACTGCTCT
GATTTGGGAACGCAAGTGAAGGACGCAATCGTTTCCTTTGAAACGGATTT
AGAGAAAAGGACATGCAAAAATTGTGGAACACTGAACTATTCCAGGCCA
AAATAAAACTTTTACGGTAATATTACGTTATGATTTATGCAATTAATGAGT
TAAGTAGCTTTATATTTCTTTCTTATTTGATTAGTTTCAGCTCAACAGCTGA
CTATTGAACCATTTTTCTAGGCCCTTCTCCCTAATCTCAATGTGGCTAAGA
CTATCCAACTTGATGATGACATTAAAGATCTTGAGGTACCGCAGACTGGG
GAATTTGAG
```

FIG.9A-3

Pichia pastoris STE13 Protein sequence (SEQ ID NO: 40):

5' DNA flanking region for PpSTE13 (SEQ ID NO:41)
amplified to generate pGLY4511:

GGAATTCGGCCTTGGGGGCCTCCAGGACTTGCTGAAATTTGCTGACTCATC
TTCGCCATCCAAGGATAATGAGTTAGCTAATGTGACAGTTAATGAGTCGT
CTTGACTAACGGGGAACATTTCATTATTTATATCCAGAGTCAATTTGATAG
CAGAGTTTGTGGTTGAAATACCTATGATTCGGGAGACTTTGTTGTAACGAC
CATTATCCACAGTTTGGACCGTGAAAATGTCATCGAAGAGAGCAGACGAC
ATATTATCTATTGTGGTAAGTGATAGTTGGAAGTCCGACTAAGGCATGAA
AATGAGAAGACTGAAAATTTAAAGTTTTTGAAAACACTAATCGGGTAATA
ACTTGGAAATTACGTTTACGTGCCTTTAGCTCTTGTCCTTACCCCTGATAAT
CTATCCATTTCCCGAGAGACAATGACATCTCGGACAGCTGAGAACCCGTT
CGATATAGAGCTTCAAGAGAATCTAAGTCCACGTTCTTCCAATTCGTCCAT
ATTGGAAAACATTAATGAGTATGCTAGAAGACATCGCAATGATTCGCTTT
CCCAAGAATGTGATAATGAAGATGAGAACGAAAATCTCAATTATACTGAT
AACTTGGCCAAGTTTTCAAAGTCTGGAGTATCAAGAAAGAGCTGTATGCT
AATATTTGGTATTTGCTTTGTTATCTGGCTGTTTCTCTTTGCCTTGTATGCG
AGGGACAATCGATTTTCCAATTTGAACGAGTACGTTCCAGATTCAAACAG
CTCGAGGAATTCC

FIG.10A

3'DNA flanking region for PpSTE13 (SEQ ID NO:42)
amplified to generate pGLY4512:

GAAGCTTCTCGAGCTACTGGGAACCACGAGACATCACTGCAGTAGTTTCC
AAGTGGATTTCAGATCACTCATTTGTGAATCCTGACAAAACTGCGATATG
GGGGTGGTCTTACGGTGGGTTCACTACGCTTAAGACATTGGAATATGATTC
TGGAGAGGTTTTCAAATATGGTATGGCTGTTGCTCCAGTAACTAATTGGCT
TTTGTATGACTCCATCTACACTGAAAGATACATGAACCTTCCAAAGGACA
ATGTTGAAGGCTACAGTGAACACAGCGTCATTAAGAAGGTTTCCAATTTT
AAGAATGTAAACCGATTCTTGGTTTGTCACGGGACTACTGATGATAACGT
GCATTTTCAGAACACACTAACCTTACTGGACCAGTTCAATATTAATGGTGT
TGTGAATTACGATCTTCAGGTGTATCCCGACAGTGAACATAGCATTGCCCA
TCACAACGCAAATAAAGTGATCTACGAGAGGTTATTCAAGTGGTTAGAGC
GGGCATTTAACGATAGATTTTTGTAACATTCCGTACTTCATGCCATACTAT
ATATCCTGCAAGGTTTCCCTTTCAGACACAATAATTGCTTTGCAATTTTAC
ATACCACCAATTGGCAAAAATAATCTCTTCAGTAAGTTGAATGCTTTTCAA
GCCAGCACCGTGAGAAATTGCTACAGCGCGCATTCTAACATCACTTTAAA
ATTCCCTCGCCGGTGCTCACTGGAGTTTCCAACCCTTAGCTTATCAAAATC
GGGTGATAACTCTGAGTTTTTTTTTTCACTTCTATTCCTAAACCTTCGCCCA
ATGCTACCACCTCCAATCAACATCCCGAAATGGATAGAAGAGAATGGACA
TCTCTTGCAACCTCCGGTTAATAATTACTGTCTCCACAGAGGAGGATTTAC
GGTAATGATTGTAGGTGGGCCTAATGGGCCAAGCTTGC

FIG.10B

5' DNA flanking region for PpDAP2 (SEQ ID NO:43)
amplified to generate pGLY4513:

GGAATTCGGCCACCTGGGCCTGTTGCTGCTGGTACTGCTGTTGGAACTGTT
GGTATTGTTGCTGATCTAAGGCCGCCTGTTCCACACCGTGTGTATCGAATG
CTTGGGCAAAATCATCGCCTGCCGGAGGCCCCACTACCGCTTGTTCCTCCT
GCTCTTGTTTGTTTTGCTCATTGATGATATCGGCGTCAATGAATTGATCCTC
AATCGTGTGGTGGTGGTGTCGTGATTCCTCTTCTTTCTTGAGTGCCTTATCC
ATATTCCTATCTTAGTGTACCAATAATTTTGTTAAACACACGCTGTTGTTTA
TGAAAAGTCGTCAAAAGGTTAAAAATTCTACTTGGTGTGTGTCAGAGAAA
GTAGTGCAGACCCCCAGTTTGTTGACTAGTTGAGAAGGCGGCTCACTATT
GCGCGAATAGCATGAGAAATTTGCAAACATCTGGCAAAGTGGTCAATACC
TGCCAACCTGCCAATCTTCGCGACGGAGGCTGTTAAGCGGGTTGGGTTCC
CAAAGTGAATGGATATTACGGGCAGGAAAAACAGCCCCTTCCACACTAGT
CTTTGCTACTGACATCTTCCCTCTCATGTATCCCGAACACAAGTATCGGGA
GTATCAACGGAGGGTGCCCTTATGGCAGTACTCCCTGTTGGTGATTGTACT
GCTATACGGGTCTCATTTGCTTATCAGCACCATCAACTTGATACACTATAA
CCACAAAAATTATCATGCACACCCAGTCAATAGTGGTATCGTTCTTAATGA
GTTTGCTGATGACGATTCATTCTCTTTGAATGGCACTCTGAACTTGGAGAA
CTGGAGAAATGGTACCTTTTCCCCTAAATTTCATTCCATTCAGTGGACCGA
AATAGGTCAGGAAGATGACCAGGGATATTACATTCTCTCTTCCAATTCCTC
TTACATAGTAAAGTCTTTATCCGACCCAGACTTTGAATCTGTTCTATTCAA
CGAGTCTACAATCACTTACAACGCTCGAGGAATTCG

FIG.11A

3' DNA flanking region for PpDAP2 (SEQ ID NO:44)
amplified to generate pGLY4514:

GAAGCTTCTCGAGGGCAGCAAAGCCTTACGTTGATGAGAATAGACTGGCC
ATTTGGGGTTGGTCTTATGGAGGTTACATGACGCTAAAGGTTTTAGAACA
GGATAAAGGTGAAACATTCAAATATGGAATGTCTGTTGCCCCTGTGACGA
ATTGGAAATTCTATGATTCTATCTACACAGAAAGATACATGCACACTCCTC
AGGACAATCCAAACTATTATAATTCGTCAATCCATGAGATTGATAATTTGA
AGGGAGTGAAGAGGTTCTTGCTAATGCACGGAACTGGTGACGACAATGTT
CACTTCCAAAATACACTCAAAGTTCTAGATTTATTTGATTTACATGGTCTT
GAAAACTATGATATCCACGTGTTCCCTGATAGTGATCACAGTATTAGATAT
CACAACGGTAATGTTATAGTGTATGATAAGCTATTCCATTGGATTAGGCGT
GCATTCAAGGCTGGCAAATAAATAGGTGCAAAAATATTATTAGACTTTTTT
TTTCGTTCGCAAGTTATTACTGTGTACCATACCGATCCAATCCGTATTGTA
ATTCATGTTCTAGATCCAAAATTTGGGACTCTAATTCATGAGGTCTAGGAA
GATGATCATCTCTATAGTTTTCAGCGGGGGGCTCGATTTGCGGTTGGTCAA
AGCTAACATCAAAATGTTTGTCAGGTTCAGTGAATGGTAACTGCTGCTCTT
GAATTGGTCGTCTGACAAATTCTCTAAGTGATAGCACTTCATCTACAATCA
TTTGCTTCATCGTTTCTATATCGTCCACGACCTCAAACGAGAAATCGAATT
TGGAAGAACAGACGGGCTCATCGTTAGGATCATGCCAAACCTTGAGATAT
GGATGCTCTAAAGCCTCAGTAACTGTAATTCTGTGAGTGGGATCTACCGTG
AGCATTCGATCCAGTAAGTCTATCGCTTCAGGGTTGGCACCGGGAAATAA
CTGGCTGAATGGGATCTTGGGCATGAATGGCAGGGAGCGAACATAATCCT
GGGCACGCTCTGATCTGATAGACTGAAGTGTCTCTTCCGAAACAGTACCC
AGCGTACTCAAAATCAAGTTCAATTGATCCACATAGTCTCTTCCTCTAAAA
ATGGGTCGGCCACCTAGGCCAAGCTTGC

FIG.11B

Nouresothricin marker cassette (SEQ ID NO:45)
amplified from pAG25:

TGTTTAGCTTGCCTCGTCCCCGCCGGGTCACCCGGCCAGCGACATGGAGG
CCCAGAATACCCTCCTTGACAGTCTTGACGTGCGCAGCTCAGGGGCATGA
TGTGACTGTCGCCCGTACATTTAGCCCATACATCCCCATGTATAATCATTT
GCATCCATACATTTTGATGGCCGCACGGCGCGAAGCAAAAATTACGGCTC
CTCGCTGCAGACCTGCGAGCAGGGAAACGCTCCCCTCACAGACGCGTTGA
ATTGTCCCCACGCCGCGCCCTGTAGAGAAATATAAAAGGTTAGGATTTG
CCACTGAGGTTCTTCTTTCATATACTTCCTTTTAAAATCTTGCTAGGATACA
GTTCTCACATCACATCCGAACATAAACAACCATGGGTACCACTCTTGAC
GACACGGCTTACCGGTACCGCACCAGTGTCCCGGGGGACGCCGAGGC
CATCGAGGCACTGGATGGGTCCTTCACCACCGACACCGTCTTCCGCG
TCACCGCCACCGGGGACGGCTTCACCCTGCGGGAGGTGCCGGTGGAC
CCGCCCCTGACCAAGGTGTTCCCCGACGACGAATCGGACGACGAATC
GGACGACGGGGAGGACGGCGACCCGGACTCCCGGACGTTCGTCGCG
TACGGGGACGACGGCGACCTGGCGGGCTTCGTGGTCGTCTCGTACTC
CGGCTGGAACCGCCGGCTGACCGTCGAGGACATCGAGGTCGCCCCG
GAGCACCGGGGGCACGGGGTCGGGCGCGCGTTGATGGGGCTCGCGA
CGGAGTTCGCCCGCGAGCGGGGCGCCGGGCACCTCTGGCTGGAGGT
CACCAACGTCAACGCACCGGCGATCCACGCGTACCGGCGGATGGGGT
TCACCCTCTGCGGCCTGGACACCGCCCTGTACGACGGCACCGCCTCG
GACGGCGAGCAGGCGCTCTACATGAGCATGCCCTGCCCCTAATCAGT
ACTGACAATAAAAAGATTCTTGTTTTCAAGAACTTGTCATTTGTATAGTTT
TTTTATATTGTAGTTGTTCTATTTTAATCAAATGTTAGCGTGATTTATATTT
TTTTTCGCCTCGACATCATCTGCCCAGATGCGAAGTTAAGTGCGCAGAAA
GTAATATCATGCGTCAATCGTATGTGAATGCTGGTCGCTATACTGCTGTCG
ATTCGATACTAACGCCGCCATCCAGTGTCGAAAACG

FIG.12

Pichia pastoris DPPIII DNA sequence (SEQ ID NO: 54):

TTTGTGCCAAATATAACAGTAAACCTGTCGTTCTGTGAACTACCAGACCAAACAAAGTCAAAAGAGGTG
TTGACACCAAAGATTGTTCAAGCAGTAAATCCGCAGTTATATCTAAGGGATGCTTCAGCAATGCAGCTG
AAAGAACAAGCGGTGACTCACTATAGTTAGTGATATCATAGCCTTTAGATTTAGGCGTCACCAATGCAT
CCCTTAAAGCGTATGCCATATGAATTGGGTAACCAATATTCTAATCACAAGGTAGTGCTGATAGGGTAC
CTTTTTTCACAGTAATCGCGTCTGATTATGTCATCACAAAATAATGTGTGGTTAAGTGAAGGACCAGTG
CCCAGTTCAACGAAAGCATTGCGTTGAGTTACGTCTCATGCCTAATGAAAAGCTAAAATGAGATTGAAT
TGTTTTGTGAATGTCCATTGGTCTGTTGGGAGTCGCTATTAGTGTCATTCAGACTTCTACAAGGACAAC
AAAACACTTGCTTATGTAAGTTCATGCTCCAACAATTTATGGTCTAACGGCTAGACAGTGCTGTGTAAT
GCCAGCCCAAATCTGAATTGGCTAACAATGAAAACCAGATTGCCTCATTTGGCCTTCTCGTGTCCTCTG
GCCCTTTTGTTCAAAGTTGAAACTCACCAAATTGATTTCGACTCAAGATTGCTTCCTTTTCGTTCCCCA
TACAAAATTCCAAAAATTATATAAAAGCTCTCCGCCGCTCCTATCCTATGCTCTCCCGTTTACAACACT
ACAGATCTGCAATTGGCTCAACGCTTATACGTAATCATATCAGAATGAGCTCCATCAAGATTGAGAATT
ACTACGCTGATGCCAAGGCCCCTATAGTATCTTTGTCGGCCAAATCCCATTTCAATGAATTGACCTCTC
AGGAAAGAAAGTACGCCCATTACATGTCCAGGGCTTCCCATTGGGGAACTAGGGTTGTTCTTAGATCAG
TTTCTCCAGAATCTGAAGTAATATATGACTTAATCATCAGTATTCATAAACATGTCAATAGTGACTACA
GCGACTTAACTAAGCATTTGGGGGAAGTGGCAGTACAGCAATATCTGGAATTTGCTTCGCAGTTTTTGT
CGAACTTAGGAAATTATAAATCTTTTGGCGATGTCAAGTTTATTCCAAGATTGCCCAGACCTGATTTTG
AGACCCTAGTCGAATGGACCAATAGTGAGACTGTTCTTCAATTGTTTGAACTTGTAAAGGATGACTTAT
ACTCATTAGATGAGAAGAACATACTTCTTGGATGGAATACTGATGGTCATGTCAGTTCTTACTACTTGA
ACAAAGTCTCAAAGGTAGAGGCTGAAGTTGTTAACGCAGCACTTGCTTCTAAGGGGATTATGCCTGAGA
ATACACGTGTTGAAAAGTTGTCTGACTCAGAATACAGGGTTCATGTTGCAAGTGCTGATATTTCTAACA
ACACAGGTTACTATCCAGATTCAATTGATTACAAAGATGCTGATGGAAAGTCATATACAATCACTTTCA
AATTTGGAGACCATGCTGCAGAATTCTCTCAAATTGTCAGCAACCTTGTCGAAGCTAAAAAGTATGCCG
CCAATGAAACTCAAGTGAAGTTGTTAGAGCACTATATCCAGTCTTTCACCACTGGTTCTATGAACGCTC
ACAAAGATTCTCAAATTGAATGGGTAAGAGACATTGGTCCATCTGTCGAGACCAACATTGGTTTCATTG
AAACGTACAGAGATCCAAGCGGTGTCAGAGGTGAATGGGAGGGTCTTGTTGCAATGGTGAATAAAGAAA
GAACCGAAAAATTTCAAAAGCTTGTCAGTAGTGCCAAACACTTCATCCAGCTGCTGCCTTGGCCCAAAG
CCTTTGAGAAAGATGTCTTTACTCCTCCTGACTTCACCTCCTTGGAGGTAC

FIG. 13-1

```
TCACTTTTGCCGGATCTGGAATTCCTGCAGGAATTAATATTCCCAATTATGATGACGTTAGGATTAACA
TTGGTTTTAAGAACGTTTCCTTGGGTAACATTTTGTCAGCTAGATCTGCCAGCGAACCAGTTA
CCTTCATTGATGAATCATTGGTTGATGTTTTCAACAAATATCGAAGTGAATCATTTGAAGTTCAAGTCG
GTATTCATGAGCTTCTAGGCCATGGGACAGGTAAACTTCTACAGGAAACTGGTGATAATTCGTACAACT
TTGATATCAATAGTCCTCCAATTGGCCTGGATGGAAAACCTGTTTCAACTTTTTACAAGAAGGGGGAGA
CTTGGGGATCAGTATTTGGATCTATTGCTGGTTCAGCTGAAGAATGTAGGGCCGAATCTGTAGCCATGT
TTTTGGTTACTAACCGTGAGCTTTTGGAGATTTTTGGCTATTCAACCAAAGAAGAACAGGATAATATCA
TCCACATCAGCTTCTTACAAATGGCTCGCGCCGGTCTGGTTGCTTTGGAGCAATGGGATCCCAAGACAA
GGAAATGGGGTCAACCTCATATGCAGGCAAGATATGCTATTCTGAGAACGTTCCTAGATGCTGGTGAGG
ACTTTGTCACTCTCAAGTACACCAAAGGAGGAGACTTTTCGGATTTGCGTATAGAGTTAGATGAGTCAA
AGATATCCACCGTTGGACAGAAAGCAATTGGAAACTTTTTACAACAGCTTCACATTCTGAAGTGTTCTG
CTGATGTCAATGGTTTGACTAAACTATACAACTCTATCACAACAGTGACCGAAGAAATCGCACAGTTTA
GGGACACTATCTTAGCCAAGCGTTTACCAAGAAAGCAGTATATCCAAGGTAACACGTTACTCGAAGATG
ACACTGCTGTTGTTAAGGAATACGCTGAGAATGAAATCGGCCTGATTCAAAGTTTTGTTGACAGGGACG
TCTAAACTATCTTGGATGGTGAGCCGCAGATGAGCCGCACACCTGTCCATCCTTTTGTGATGACGAGAT
TCACTACTGATTATCTAACCTCAAACTCATTTGTTCCGTAATCAAATACACCATCTTGCTAAATTTGGC
TTTACTTTAAAATGAACCCTTTTTTCTATCAAAGTTGCAATTTCAAACGCTCGTTCACCATCAGTACAG
CTTCCTGGAGTAAGCCGTTCAACTATATTTTCAGCAGAGTAAGTCCGAATTTTCTTTTCTTTTCTAACT
ATTTCTAACCGTCAACATCCAGGTCACACTAGATCTATTCTGGATTATCTCTCATTTGGTAACCCTTGG
CGGGGTTTCGCTTTTGCTGTTTGCCAACCTGACGACTGTTCTCGTTTTCATCCCTAACTATTTCTTATA
TAAAATGTGCCTGTTGGGATCGATGTTAACGTACTCTCTAGTTGTCTACCGCAGAATATTTCCCAGTGT
TAGTGACGAATCAAAGAACACAGAAGATCTAAGAAGCCAAGAAGGGATTTCTGCCGAACTTGACTCTAG
TCAAAAACAATCATCGATGACCCTGCCGGAACTTTTGAGGTCTGAGAATGGACTTTTATTATGTCTAGG
TGCACTTTACTTCTTTACAAATGAAAATGTACTAAAGCTGTTGCCGTTTGGTGTTTATTCATTATTAAA
CTTGTGCTACTTTTTCTGTACGGAGGTATTTTGCGACTATTCATTTGCAGCGGCCTTTATGCCCCTGGT
GGTATACATGGAAACACCTTTACTCGTATTTGCGGCTCATATGGATATGCTGTTATTTTGGGTACTTTT
GAAAGAGTCCAAAATCAAATCTCATTTGTACGCTGTTGCATTACACTTGTTCATCTTTGTATTAAGGTT
GGAAACTTCAGAAGCGAGTAGAAGAGCTTTATATGGCTGGATTCATTATATTGATTTGTTCTTCTCTCT
GGATGGAATACCAGTTTTATGCCGTCTTTACTGGAATAATGTC
```

FIG.13-2

SEQUENCE LISTING

```
<160> NUMBER OF SEQ ID NOS: 54

<210> SEQ ID NO 1
<211> LENGTH: 7
<212> TYPE: PRT
<213> ORGANISM: Artificial Sequence
<220> FEATURE:
<223> OTHER INFORMATION: synthetic

<400> SEQUENCE: 1

Leu Pro Ala Gln Val Ala Phe
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Ala Gln Val Ala Phe
1               5

<210> SEQ ID NO 3
<211> LENGTH: 466
<212> TYPE: PRT
<213> ORGANISM: Artificial Sequence
<220> FEATURE:
<223> OTHER INFORMATION: synthetic

<400> SEQUENCE: 3

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160
```

```
Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
        180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 4
<211> LENGTH: 7
<212> TYPE: PRT
<213> ORGANISM: Artificial Sequence
<220> FEATURE:
<223> OTHER INFORMATION: synthetic

<400> SEQUENCE: 4

Thr Pro Leu Gly Pro Ala Ser
 1               5

<210> SEQ ID NO 5
<211> LENGTH: 5
<212> TYPE: PRT
<213> ORGANISM: Artificial Sequence
<220> FEATURE:
```

-continued

```
<223> OTHER INFORMATION: synthetic

<400> SEQUENCE: 5

Leu Gly Pro Ala Ser
 1               5

<210> SEQ ID NO 6
<211> LENGTH: 173
<212> TYPE: PRT
<213> ORGANISM: Artificial Sequence
<220> FEATURE:
<223> OTHER INFORMATION: synthetic

<400> SEQUENCE: 6

Thr Pro Leu Gly Pro Ala Ser Ser Leu Pro Gln Ser Phe Leu Leu Cys
 1               5                  10                  15

Leu Glu Gln Val Arg Lys Ile Gln Gly Asp Gly Ala Ala Leu Gln Glu
             20                  25                  30

Lys Leu Cys Ala Thr Tyr Lys Leu Cys His Pro Glu Glu Leu Val Leu
         35                  40                  45

Leu Gly His Ser Leu Gly Ile Pro Trp Ala Pro Leu Ser Ser Cys Pro
     50                  55                  60

Ser Gln Ala Leu Gln Leu Ala Gly Cys Leu Ser Gln Leu His Ser Gly
 65                  70                  75                  80

Leu Phe Leu Tyr Gln Gly Leu Leu Gln Ala Leu Glu Gly Ile Ser Pro
                 85                  90                  95

Glu Leu Gly Pro Thr Leu Asp Thr Leu Gln Leu Asp Val Ala Asp Phe
            100                 105                 110

Ala Thr Thr Ile Trp Gln Gln Met Glu Glu Leu Gly Met Ala Pro Ala
        115                 120                 125

Leu Gln Pro Thr Gln Gly Ala Met Pro Ala Phe Ala Ser Ala Phe Gln
    130                 135                 140

Arg Arg Ala Gly Gly Val Leu Val Ala Ser His Leu Gln Ser Phe Leu
145                 150                 155                 160

Glu Val Ser Tyr Arg Val Leu Arg His Leu Ala Gln Pro
                165                 170

<210> SEQ ID NO 7
<211> LENGTH: 31
<212> TYPE: DNA
<213> ORGANISM: Artificial Sequence
<220> FEATURE:
<223> OTHER INFORMATION: synthetic

<400> SEQUENCE: 7
ggctcgagga tctgtttagc ttgcctcgtc c                                  31

<210> SEQ ID NO 8
<211> LENGTH: 33
<212> TYPE: DNA
<213> ORGANISM: Artificial Sequence
<220> FEATURE:
<223> OTHER INFORMATION: synthetic

<400> SEQUENCE: 8
ggctcgaggg agctcgtttt cgacactgga tgg                                33

<210> SEQ ID NO 9
<211> LENGTH: 26
<212> TYPE: DNA
<213> ORGANISM: Artificial Sequence
```

```
<220> FEATURE:
<223> OTHER INFORMATION: synthetic

<400> SEQUENCE: 9
catgcccctg agctgcgcac gtcaag                                          26

<210> SEQ ID NO 10
<211> LENGTH: 26
<212> TYPE: DNA
<213> ORGANISM: Artificial Sequence
<220> FEATURE:
<223> OTHER INFORMATION: synthetic

<400> SEQUENCE: 10
cagaaagtaa tatcatgcgt caatcg                                          26

<210> SEQ ID NO 11
<211> LENGTH: 30
<212> TYPE: DNA
<213> ORGANISM: Artificial Sequence
<220> FEATURE:
<223> OTHER INFORMATION: synthetic

<400> SEQUENCE: 11
ggcgattacc gttgatgttg aagtggcgag                                      30

<210> SEQ ID NO 12
<211> LENGTH: 30
<212> TYPE: DNA
<213> ORGANISM: Artificial Sequence
<220> FEATURE:
<223> OTHER INFORMATION: synthetic

<400> SEQUENCE: 12
catccagagg cacttcaccg cttgccagcg                                      30

<210> SEQ ID NO 13
<211> LENGTH: 34
<212> TYPE: DNA
<213> ORGANISM: Artificial Sequence
<220> FEATURE:
<223> OTHER INFORMATION: synthetic

<400> SEQUENCE: 13
ggaattcggc cttgggggcc tccaggactt gctg                                 34

<210> SEQ ID NO 14
<211> LENGTH: 37
<212> TYPE: DNA
<213> ORGANISM: Artificial Sequence
<220> FEATURE:
<223> OTHER INFORMATION: synthetic

<400> SEQUENCE: 14
ggaattcctc gagctgtttg aatctggaac gtactcg                              37

<210> SEQ ID NO 15
<211> LENGTH: 37
<212> TYPE: DNA
<213> ORGANISM: Artificial Sequence
<220> FEATURE:
<223> OTHER INFORMATION: synthetic

<400> SEQUENCE: 15
gaagcttctc gagctactgg gaaccacgag acatcac                              37
```

<210> SEQ ID NO 16
<211> LENGTH: 38
<212> TYPE: DNA
<213> ORGANISM: Artificial Sequence
<220> FEATURE:
<223> OTHER INFORMATION: synthetic

<400> SEQUENCE: 16
gcaagcttgg cccattaggc ccacctacaa tcattacc                    38

<210> SEQ ID NO 17
<211> LENGTH: 27
<212> TYPE: DNA
<213> ORGANISM: Artificial Sequence
<220> FEATURE:
<223> OTHER INFORMATION: synthetic

<400> SEQUENCE: 17
caaggcacat taaaagtccg ccaaagg                                27

<210> SEQ ID NO 18
<211> LENGTH: 29
<212> TYPE: DNA
<213> ORGANISM: Artificial Sequence
<220> FEATURE:
<223> OTHER INFORMATION: synthetic

<400> SEQUENCE: 18
gtggcccttg tattgataga agtattcag                              29

<210> SEQ ID NO 19
<211> LENGTH: 27
<212> TYPE: DNA
<213> ORGANISM: Artificial Sequence
<220> FEATURE:
<223> OTHER INFORMATION: synthetic

<400> SEQUENCE: 19
cacgtctatc gttgaaccaa aacagac                                27

<210> SEQ ID NO 20
<211> LENGTH: 26
<212> TYPE: DNA
<213> ORGANISM: Artificial Sequence
<220> FEATURE:
<223> OTHER INFORMATION: synthetic

<400> SEQUENCE: 20
gtaaccaatg gtatctccaa cgacag                                 26

<210> SEQ ID NO 21
<211> LENGTH: 37
<212> TYPE: DNA
<213> ORGANISM: Artificial Sequence
<220> FEATURE:
<223> OTHER INFORMATION: synthetic

<400> SEQUENCE: 21
ggaattcggc cacctgggcc tgttgctgct ggtactg                     37

<210> SEQ ID NO 22
<211> LENGTH: 36
<212> TYPE: DNA
<213> ORGANISM: Artificial Sequence
<220> FEATURE:
<223> OTHER INFORMATION: synthetic

<400> SEQUENCE: 22
cgaattcctc gagcgttgta agtgattgta gactcg                                    36

<210> SEQ ID NO 23
<211> LENGTH: 33
<212> TYPE: DNA
<213> ORGANISM: Artificial Sequence
<220> FEATURE:
<223> OTHER INFORMATION: synthetic

<400> SEQUENCE: 23
gaagcttctc gagggcagca aagccttacg ttg                                       33

<210> SEQ ID NO 24
<211> LENGTH: 37
<212> TYPE: DNA
<213> ORGANISM: Artificial Sequence
<220> FEATURE:
<223> OTHER INFORMATION: synthetic

<400> SEQUENCE: 24
gcaagcttgg cctaggtggc cgacccattt ttagagg                                   37

<210> SEQ ID NO 25
<211> LENGTH: 28
<212> TYPE: DNA
<213> ORGANISM: Artificial Sequence
<220> FEATURE:
<223> OTHER INFORMATION: synthetic

<400> SEQUENCE: 25
cactttcatc ctgaggatct tggtcctg                                             28

<210> SEQ ID NO 26
<211> LENGTH: 28
<212> TYPE: DNA
<213> ORGANISM: Artificial Sequence
<220> FEATURE:
<223> OTHER INFORMATION: synthetic

<400> SEQUENCE: 26
catataccaa agcaattgat atctggtc                                             28

<210> SEQ ID NO 27
<211> LENGTH: 28
<212> TYPE: DNA
<213> ORGANISM: Artificial Sequence
<220> FEATURE:
<223> OTHER INFORMATION: synthetic

<400> SEQUENCE: 27
cggataagag acataattgg cgccattc                                             28

<210> SEQ ID NO 28
<211> LENGTH: 28
<212> TYPE: DNA
<213> ORGANISM: Artificial Sequence
<220> FEATURE:
<223> OTHER INFORMATION: synthetic

<400> SEQUENCE: 28
ctttctattg aggatttctt ggttgctg                                             28

<210> SEQ ID NO 29

<210> SEQ ID NO 29
<211> LENGTH: 44
<212> TYPE: DNA
<213> ORGANISM: Artificial Sequence
<220> FEATURE:
<223> OTHER INFORMATION: synthetic

<400> SEQUENCE: 29
cgccatccag tgtcgaaaac gctgtttgaa tctggaacgt actc          44

<210> SEQ ID NO 30
<211> LENGTH: 44
<212> TYPE: DNA
<213> ORGANISM: Artificial Sequence
<220> FEATURE:
<223> OTHER INFORMATION: synthetic

<400> SEQUENCE: 30
gagtacgttc cagattcaaa cagcgttttc gacactggat ggcg          44

<210> SEQ ID NO 31
<211> LENGTH: 46
<212> TYPE: DNA
<213> ORGANISM: Artificial Sequence
<220> FEATURE:
<223> OTHER INFORMATION: synthetic

<400> SEQUENCE: 31
gtgatgtctc gtggttccca gtagtgttta gcttgcctcg tccccg          46

<210> SEQ ID NO 32
<211> LENGTH: 46
<212> TYPE: DNA
<213> ORGANISM: Artificial Sequence
<220> FEATURE:
<223> OTHER INFORMATION: synthetic

<400> SEQUENCE: 32
cggggacgag gcaagctaaa cactactggg aaccacgaga catcac          46

<210> SEQ ID NO 33
<211> LENGTH: 47
<212> TYPE: DNA
<213> ORGANISM: Artificial Sequence
<220> FEATURE:
<223> OTHER INFORMATION: synthetic

<400> SEQUENCE: 33
cgccatccag tgtcgaaaac gcgttgtaag tgattgtaga ctcgttg        47

<210> SEQ ID NO 34
<211> LENGTH: 47
<212> TYPE: DNA
<213> ORGANISM: Artificial Sequence
<220> FEATURE:
<223> OTHER INFORMATION: synthetic

<400> SEQUENCE: 34
caacgagtct acaatcactt acaacgcgtt ttcgacactg gatggcg        47

<210> SEQ ID NO 35
<211> LENGTH: 42
<212> TYPE: DNA
<213> ORGANISM: Artificial Sequence
<220> FEATURE:
<223> OTHER INFORMATION: synthetic

<400> SEQUENCE: 35

```
caacgtaagg ctttgctgcc tgtttagctt gcctcgtccc cg              42
```

<210> SEQ ID NO 36
<211> LENGTH: 42
<212> TYPE: DNA
<213> ORGANISM: Artificial Sequence
<220> FEATURE:
<223> OTHER INFORMATION: synthetic

<400> SEQUENCE: 36

```
cggggacgag gcaagctaaa caggcagcaa agccttacgt tg              42
```

<210> SEQ ID NO 37
<211> LENGTH: 4460
<212> TYPE: DNA
<213> ORGANISM: Artificial Sequence
<220> FEATURE:
<223> OTHER INFORMATION: synthetic

<400> SEQUENCE: 37

```
gtgaagtaga tagctttgtt gttggagtga gcgatggcaa taccaaactc gttacgttta      60
gcaaactctt tcacaaactg gcgcaattca gtaacgtcat cgaattcctt ctcttggatc     120
catggcgtca caaaaactgc ttcatcgtcc tcaggtagaa ttggaatatc cttaggtcct     180
cctggggtgg caggaataac atagtgttgc acgtgactgg gaactctcat agtgtttaca     240
tggctatgac cgtgaaggac atgctgatgg cttgccgcag tcggttgatg gtgatactcg     300
atgtttaagt gtgacaaatc gttactggca gctgctgtgt acttcggtat aagatgctgg     360
atctttgcct cggcactttc atcctgagga tcttggtcct gaccgggctg gtggtggtca     420
atgtgaacct gggcctgttg ctgctggtac tgctgttgga actgttggta ttgttgctga     480
tctaaggccg cctgttccac accgtgtgta tcgaatgctt gggcaaaatc atcgcctgcc     540
ggaggcccca ctaccgcttg ttcctcctgc tcttgtttgt tttgctcatt gatgatatcg     600
gcgtcaatga attgatcctc aatcgtgtgg tggtggtgtc gtgatcctct tctttcttga     660
gtgccttatc catattccta tcttagtgta ccaataattt tgttaaacac acgctgttgt     720
tatgaaaagt cgtcaaaagg ttaaaaattc tacttggtgt gtgtcagaga aagtagtgca     780
gaccccagt ttgttgacta gttgagaagg cggctcacta ttgcgcgaat agcatgagaa     840
atttgcaaac atctggcaaa gtggtcaata cctgccaacc tgccaatctt cgcgacggag     900
gctgttaagc gggttgggtt cccaaagtga atggatatta cgggcaggaa aaacagcccc     960
ttccacacta gtctttgcta ctgacatctt ccctctcatg tatcccgaac acaagtatcg    1020
ggagtatcaa cggagggtgc ccttatggca gtactccctg ttggtgattg tactgctata    1080
cgggtctcat ttgcttatca gcaccatcaa cttgatacac tataaccaca aaaattatca    1140
tgcacaccca gtcaatagtg gtatcgttct taatgagttt gctgatgacg attcattctc    1200
tttgaatggc actctgaact tggagaactg gagaaatggt accttttccc ctaaatttca    1260
ttccattcag tggaccgaaa taggtcagga agatgaccag ggatattaca ttctctcttc    1320
caattcctct tacatagtaa agtctttatc cgacccagac tttgaatctg ttctattcaa    1380
cgagtctaca atcacttaca acggtgaaga acatcatgtg gaagacgtca tagtgtccaa    1440
taatcttcaa tatgcattgg tagttacgga taagagacat aattggcgcc attcttttt    1500
tgcgaattac tggctgtata aagtcaacaa tcctgaacag gttcagcctt tgtttgatac    1560
agatctatcg ttgaatggtc ttattagcct tgtccattgg tctccggatt cttcccaagt    1620
```

```
tgcatttgtg ttggaaaata acatatattt gaagcatctt acaacttttt ctgattcaag    1680
gattgatcaa ctaacttatg atggaggcga aaacatattt tatggcaaac cagattgggt    1740
ttatgaagaa gaagtgtttg aaagcaactc tgctatgtgg tggtctccaa atggaaagtt    1800
tttatcaata ttgcgaacta atgacaccca agtgcctgtc tatcctattc catattttgt    1860
tcagtctgat gctgaaacag ctatcgatga ataccctctt ctgaaacaca taaaataccc    1920
aaaggcagga tttcccaatc cagttgttga tgtgattgta tacgatgttc aacgccagca    1980
catatctagg ttacctgctg gtgatccttt ctacaacgat gagaacatta ccaatgagga    2040
cagacttatc actgagatca tctgggttgg tgattcacgg ttcctgacca agattacgaa    2100
cagggaaagt gacttgttag cattttatct ggtagacgct gaggctaaca atagtaagct    2160
ggtaagattc caagatgcta agagcaccaa gtcttggttt gaaattgaac acaacacatt    2220
gtatattcct aaggatactt cagtgggaag ggcacaagat ggctacatcg acaccataga    2280
tgttaacggc tacaaccatt tagcctattt ctcaccacca gacaacccag accccaaggt    2340
cattcttacg cgtggtgatt gggaagtcgt tgacagtcca tctgcatttg acttcaaaag    2400
aaatttggtt tactttacag caaccaagaa atcctcaata gaaagacatg tttattgtgt    2460
tgggatagac gggaaacaat tcaacaatgt aactgatgtt tcatcagatg gatactacag    2520
tacaagcttt tcccctggag caagatatgt attgctatca caccaaggtc cccgtgtacc    2580
ttatcaaaag atgatagatc ttgtcaaagg caccgaagaa ataatcgaat ctaacgaaga    2640
tttgaaagac tccgttgctt tatttgattt acctgatgtc aagtacggcg aaatcgagct    2700
tgaaaaaggt gtcaagtcaa actacgttga gatcaggcct aagaacttcg atgaaagcaa    2760
aaagtatccg gttttatttt ttgtgtatgg ggggccaggt tcccaattgg taacaaagac    2820
attttctaag agtttccagc atgttgtatc ctctgagctt gacgtcattg ttgtcacggt    2880
ggatggaaga gggactggat ttaaaggtag aaaatataga tccatagtgc gggacaactt    2940
gggtcattat gaatccctgg accaaatcac ggcaggaaaa atttgggcag caaagcctta    3000
cgttgatgag aatagactgg ccatttgggg ttggtcttat ggaggttaca tgacgctaaa    3060
ggttttagaa caggataaag gtgaaacatt caaatatgga atgtctgttg ccctgtgac    3120 gaattggaaa ttctatgatt ctatctacac agaaagatac atgcacactc ctcaggacaa    3180
tccaaactat tataattcgt caatccatga gattgataat ttgaagggag tgaagaggtt    3240
cttgctaatg cacggaactg gtgacgacaa tgttcacttc caaaatacac tcaaagttct    3300
agatttattt gatttacatg gtcttgaaaa ctatgatatc cacgtgttcc ctgatagtga    3360
tcacagtatt agatatcaca acggtaatgt tatagtgtat gataagctat tccattggat    3420
taggcgtgca ttcaaggctg gcaaataaat aggtgcaaaa atattattag actttttttt    3480
tcgttcgcaa gttattactg tgtaccatac cgatccaatc cgtattgtaa ttcatgttct    3540
agatccaaaa tttgggactc taattcatga ggtctaggaa gatgatcatc tctatagttt    3600
tcagcggggg gctcgatttg cggttggtca agctaacat caaaatgttt gtcaggttca    3660
gtgaatggta actgctgctc ttgaattggt cgtctgacaa attctctaag tgatagcact    3720
tcatctacaa tcatttgctt catcgtttct atatcgtcca cgacctcaaa cgagaaatcg    3780
aatttggaag aacagacggg ctcatcgtta ggatcatgcc aaaccttgag atatggatgc    3840
tctaaagcct cagtaactgt aattctgtga gtgggatcta ccgtgagcat tcgatccagt    3900
aagtctatcg cttcagggtt ggcaccggga ataactggc tgaatgggat cttgggcatg    3960
aatggcaggg agcgaacata atcctgggca cgctctgatc tgatagactg aagtgtctct    4020
```

```
tccgaaacag tacccagcgt actcaaaatc aagttcaatt gatccacata gtctcttcct   4080
ctaaaaatgg gtgggccacc taagagttcg gccaatatac atccaactga ccagatatca   4140
attgctttgg tatatgtctg aaaactaaga attatctccg gtgcccgata ccacctggta   4200
gcaacatatt ccgtaagaaa gccagcattc ttctctgcat cactactata acctcttgca   4260
agtccaaagt cacaaatctt aagttcgcaa tctgagttca ccaatagatt gacgggttta   4320
agatctctat gcagcacatc tgctgaatgg atatacttta agcccccgag aatttggtag   4380
ataaagctct gatagtggct gtcagtcaaa ggttgttttg atttgattat atgatgcaag   4440
tcacattcca tcaattcttc                                               4460
```

<210> SEQ ID NO 38
<211> LENGTH: 816
<212> TYPE: PRT
<213> ORGANISM: Artificial Sequence
<220> FEATURE:
<223> OTHER INFORMATION: synthetic

<400> SEQUENCE: 38

```
Met Tyr Pro Glu His Lys Tyr Arg Glu Tyr Gln Arg Arg Val Pro Leu
1               5                   10                  15

Trp Gln Tyr Ser Leu Leu Val Ile Val Leu Leu Tyr Gly Ser His Leu
            20                  25                  30

Leu Ile Ser Thr Ile Asn Leu Ile His Tyr Asn His Lys Asn Tyr His
        35                  40                  45

Ala His Pro Val Asn Ser Gly Ile Val Leu Asn Glu Phe Ala Asp Asp
    50                  55                  60

Asp Ser Phe Ser Leu Asn Gly Thr Leu Asn Leu Glu Asn Trp Arg Asn
65                  70                  75                  80

Gly Thr Phe Ser Pro Lys Phe His Ser Ile Gln Trp Thr Glu Ile Gly
                85                  90                  95

Gln Glu Asp Asp Gln Gly Tyr Tyr Ile Leu Ser Ser Asn Ser Ser Tyr
            100                 105                 110

Ile Val Lys Ser Leu Ser Asp Pro Asp Phe Glu Ser Val Leu Phe Asn
        115                 120                 125

Glu Ser Thr Ile Thr Tyr Asn Gly Glu Glu His Val Glu Asp Val
    130                 135                 140

Ile Val Ser Asn Asn Leu Gln Tyr Ala Leu Val Val Thr Asp Lys Arg
145                 150                 155                 160

His Asn Trp Arg His Ser Phe Phe Ala Asn Tyr Trp Leu Tyr Lys Val
                165                 170                 175

Asn Asn Pro Glu Gln Val Gln Pro Leu Phe Asp Thr Asp Leu Ser Leu
            180                 185                 190

Asn Gly Leu Ile Ser Leu Val His Trp Ser Pro Asp Ser Ser Gln Val
        195                 200                 205

Ala Phe Val Leu Glu Asn Asn Ile Tyr Leu Lys His Leu Asn Asn Phe
    210                 215                 220

Ser Asp Ser Arg Ile Asp Gln Leu Thr Tyr Asp Gly Gly Glu Asn Ile
225                 230                 235                 240

Phe Tyr Gly Lys Pro Asp Trp Val Tyr Glu Glu Val Phe Glu Ser
                245                 250                 255

Asn Ser Ala Met Trp Trp Ser Pro Asn Gly Lys Phe Leu Ser Ile Leu
            260                 265                 270

Arg Thr Asn Asp Thr Gln Val Pro Val Tyr Pro Ile Pro Tyr Phe Val
```

-continued

```
            275                 280                 285
Gln Ser Asp Ala Glu Thr Ala Ile Asp Glu Tyr Pro Leu Leu Lys His
290                 295                 300
Ile Lys Tyr Pro Lys Ala Gly Phe Pro Asn Pro Val Asp Val Ile
305                 310                 315                 320
Val Tyr Asp Val Gln Arg Gln His Ile Ser Arg Leu Pro Ala Gly Asp
                    325                 330                 335
Pro Phe Tyr Asn Asp Glu Asn Ile Thr Asn Glu Asp Arg Leu Ile Thr
                340                 345                 350
Glu Ile Ile Trp Val Gly Asp Ser Arg Phe Leu Thr Lys Ile Thr Asn
            355                 360                 365
Arg Glu Ser Asp Leu Leu Ala Phe Tyr Leu Val Asp Ala Glu Ala Asn
370                 375                 380
Asn Ser Lys Leu Val Arg Phe Gln Asp Ala Lys Ser Thr Lys Ser Trp
385                 390                 395                 400
Phe Glu Ile Glu His Asn Thr Leu Tyr Ile Pro Lys Asp Thr Ser Val
                    405                 410                 415
Gly Arg Ala Gln Asp Gly Tyr Ile Asp Thr Ile Asp Val Asn Gly Tyr
                420                 425                 430
Asn His Leu Ala Tyr Phe Ser Pro Asp Asn Pro Asp Pro Lys Val
            435                 440                 445
Ile Leu Thr Arg Gly Asp Trp Glu Val Val Asp Ser Pro Ser Ala Phe
450                 455                 460
Asp Phe Lys Arg Asn Leu Val Tyr Phe Thr Ala Thr Lys Lys Ser Ser
465                 470                 475                 480
Ile Glu Arg His Val Tyr Cys Val Gly Ile Asp Gly Lys Gln Phe Asn
                    485                 490                 495
Asn Val Thr Asp Val Ser Ser Asp Gly Tyr Tyr Ser Thr Ser Phe Ser
                500                 505                 510
Pro Gly Ala Arg Tyr Val Leu Leu Ser His Gln Gly Pro Arg Val Pro
            515                 520                 525
Tyr Gln Lys Met Ile Asp Leu Val Lys Gly Thr Glu Glu Ile Ile Glu
530                 535                 540
Ser Asn Glu Asp Leu Lys Asp Ser Val Ala Leu Phe Asp Leu Pro Asp
545                 550                 555                 560
Val Lys Tyr Gly Glu Ile Glu Leu Glu Lys Gly Val Lys Ser Asn Tyr
                    565                 570                 575
Val Glu Ile Arg Pro Lys Asn Phe Asp Glu Ser Lys Lys Tyr Pro Val
                580                 585                 590
Leu Phe Phe Val Tyr Gly Gly Pro Gly Ser Gln Leu Val Thr Lys Thr
            595                 600                 605
Phe Ser Lys Ser Phe Gln His Val Ser Ser Glu Leu Asp Val Ile
610                 615                 620
Val Val Thr Val Asp Gly Arg Gly Thr Gly Phe Lys Gly Arg Lys Tyr
625                 630                 635                 640
Arg Ser Ile Val Arg Asp Asn Leu Gly His Tyr Glu Ser Leu Asp Gln
                    645                 650                 655
Ile Thr Ala Gly Lys Ile Trp Ala Ala Lys Pro Tyr Val Asp Glu Asn
                660                 665                 670
Arg Leu Ala Ile Trp Gly Trp Ser Tyr Gly Gly Tyr Met Thr Leu Lys
            675                 680                 685
Val Leu Glu Gln Asp Lys Gly Glu Thr Phe Lys Tyr Gly Met Ser Val
690                 695                 700
```

```
Ala Pro Val Thr Asn Trp Lys Phe Tyr Asp Ser Ile Tyr Thr Glu Arg
705                 710                 715                 720

Tyr Met His Thr Pro Gln Asp Asn Pro Asn Tyr Tyr Asn Ser Ser Ile
                725                 730                 735

His Glu Ile Asp Asn Leu Lys Gly Val Lys Arg Phe Leu Leu Met His
            740                 745                 750

Gly Thr Gly Asp Asp Asn Val His Phe Gln Asn Thr Leu Lys Val Leu
        755                 760                 765

Asp Leu Phe Asp Leu His Gly Leu Glu Asn Tyr Asp Ile His Val Phe
    770                 775                 780

Pro Asp Ser Asp His Ser Ile Arg Tyr His Asn Gly Asn Val Ile Val
785                 790                 795                 800

Tyr Asp Lys Leu Phe His Trp Ile Arg Arg Ala Phe Lys Ala Gly Lys
                805                 810                 815

<210> SEQ ID NO 39
<211> LENGTH: 4615
<212> TYPE: DNA
<213> ORGANISM: Artificial Sequence
<220> FEATURE:
<223> OTHER INFORMATION: synthetic

<400> SEQUENCE: 39
gacattgcta gttgcagtat tcaacgaatc atcagatatc aggctcaggt cattatatga      60
ggcctctgtc tctattttca gtagctcttt aggggatatt tgattaagaa aaccatccaa     120
aagtagggat tgcatgggcc ttgtggggtt ctaggtaaag aattagaaat tactcaccgc     180
gattctaggg ctcctagata gtgaatgaag aggcaggaca gaacttcaag aagaagagca     240
gaaagatgtt cgataggttc caaggaggtt taatctactt ttacagttgc tgtttagcat     300
tactcaaagt tccgtgtcgg tggagggtca actaattgta ttatctagta cgttaccaag     360
cactaactgt tttgccaaac gttaccagtt ttctctctaa cgacggatca gtatatacaa     420
gttatcttgc ttcaaagaag caagggactt gtagccaccc tcaaggcaca ttaaaagtcc     480
gccaaaggaa acgtacactt ttattttatc ctcatctcct tcctcaaact tataaacagt     540
cccaaacata acgtaatcgt agtcgtcagc caaagatttg tcagttggct ttgggggcct     600
ccaggacttg ctgaaatttg ctgactcatc ttcgccatcc aaggataatg agttagctaa     660
tgtgacagtt aatgagtcgt cttgactaac ggggaacatt tcattattta tatccagagt     720
caatttgata gcagagtttg tggttgaaat acctatgatt cgggagactt tgttgtaacg     780
accattatcc acagtttgga ccgtgaaaat gtcatcgaag agagcagacg acatattatc     840
tattgtggta agtgatagtt ggaagtccga ctaaggcatg aaaatgagaa gactgaaaat     900
ttaaagtttt tgaaaacact aatcgggtaa aacttggaa attacgttta cgtgccttta     960
gctcttgtcc ttaccoctga taatctatcc atttcccgag agacaatgac atctcggaca    1020
gctgagaacc cgttcgatat agagcttcaa gagaatctaa gtccacgttc ttccaattcg    1080
tccatattgg aaaacattaa tgagtatgct agaagacatc gcaatgattc gctttcccaa    1140
gaatgtgata atgaagatga aacgaaaat ctcaattata ctgataactt ggccaagttt    1200
tcaaagtctg gagtatcaag aaagagctgt atgctaatat ttggtatttg ctttgttatc    1260
tggctgtttc tctttgcctt gtatgcgagg gacaatcgat tttccaattt gaacgagtac    1320
gttccagatt caaacagcca cggaactgct tctgccacca cgtctatcgt tgaaccaaaa    1380
cagactgaat tacctgaaag caaagattct aacactgatt atcaaaaagg agctaaattg    1440
```

```
agccttagcg gctggagatc aggtctgtac aatgtctatc caaaactgat ctctcgtggt   1500
gaagatgaca tatactatga acacagtttt catcgtatag atgaaaagag gattacagac   1560
tctcaacacg gtcgaactgt atttaactat gagaaaattg aagtaaatgg aatcacgtat   1620
acagtgtcat ttgtcaccat ttctccttac gattctgcca aattcttagt cgcatgcgac   1680
tatgaaaaac actggagaca ttctacgttt gcaaaatatt tcatatatga taaggaaagc   1740
gaccaagagg atagctttgt acctgtctac gatgacaagg cattgagctt cgttgaatgg   1800
tcgccctcag gtgatcatgt agtattcgtt tttgaaaaca atgtatacct caaacaactc   1860
tcaactttag aggttaagca ggtaactttt gatggtgatg agagtatttta caatggtaag   1920 cctgactgga tctatgaaga ggaagtttta agtagcgaca gagccatatg gtggaatgac   1980
gatggatcgt actttacgtt cttgagactt gatgacagca atgtcccaac cttcaacttg   2040
cagcattttt ttgaagaaac aggctctgtg tcgaaatatc cggtcattga tcgattgaaa   2100
tatccaaaac caggatttga caaccccctg gtttctttgt ttagttacaa cgttgccaag   2160
caaaagttag aaaagctaaa tattggagca gcagtttctt tgggagaaga cttcgtgctt   2220
tacagtttaa aatggataga caattctttt ttccttgtcga agttcacaga ccgcacttcg   2280
aaaaaaatgg aagttactct agtggacatt gaagccaatt ctgcttcggt ggtgagaaaa   2340
catgatgcaa ctgagtataa cggctggttc actggagaat tttctgttta tcctgtcgtt   2400
ggagatacca ttggttacat tgatgtaatc tattatgagg actacgatca cttggcttat   2460
tatccagact gcacatccga taagtatatt gtgcttacag atggttcatg gaatgttgtt   2520
ggacctggag ttttagaagt gcttgaagat agagtctact ttatcggcac caaagaatca   2580
tcaatggaac atcacttgta ttatacatca ttaacgggac ccaaggttaa ggctgttatg   2640
gatatcaaag aacctgggta ctttgatgta aacattaagg gaaaatatgc tttactatct   2700
tacagaggcc ccaaactccc ataccagaaa tttattgatc tttctgaccc tagtacaaca   2760
agtcttgatg acatttttatc gtctaataga ggaattgtcg aggttagttt agcaactcac   2820
agcgttcctg tttctaccta tactaatgta acacttgagg acggcgtcac actgaacatg   2880
attgaagtgt tgcctgccaa ttttaatcct agcaagaagt acccactgtt ggtcaacatt   2940
tatggtggac cgggctccca gaagttagat gtgcagttca acattgggtt tgagcatatt   3000
atttcttcgt cactggatgc aatagtgctt tacatagatc cgagaggtac tggaggtaaa   3060
agctgggctt ttaaatctta cgctacagag aaaataggct actgggaacc acgagacatc   3120
actgcagtag tttccaagtg gatttcagat cactcatttg tgaatcctga caaaactgcg   3180 atatggggt ggtcttacgg tgggttcact acgcttaaga cattggaata tgattctgga   3240
gaggttttca aatatggtat ggctgttgct ccagtaacta attggctttt gtatgactcc   3300
atctacactg aaagatacat gaaccttcca aaggacaatg ttgaaggcta cagtgaacac   3360
agcgtcatta agaaggtttc caattttaag aatgtaaacc gattcttggt ttgtcacggg   3420
actactgatg ataacgtgca ttttcagaac acactaacct tactggacca gttcaatatt   3480
aatggtgttg tgaattacga tcttcaggtg tatcccgaca gtgaacatag cattgcccat   3540
cacaacgcaa ataaagtgat ctacgagagg ttattcaagt ggttagagcg ggcatttaac   3600
gatagatttt tgtaacattc cgtacttcat gccatactat atatcctgca aggtttccct   3660
ttcagacaca ataattgctt tgcaatttta cataccacca attggcaaaa ataatctctt   3720
cagtaagttg aatgcttttc aagccagcac cgtgagaaat tgctacagcg cgcattctaa   3780
```

```
catcactta aaattccctc gccggtgctc actggagttt ccaaccctta gcttatcaaa    3840
atcgggtgat aactctgagt ttttttttc acttctattc ctaaacctc gcccaatgct     3900 accacctcca atcaacatcc cgaaatggat agaagagaat ggacatctct tgcaacctcc   3960
ggttaataat tactgtctcc acagaggagg atttacggta atgattgtag gtgggcctaa   4020
tgagagaacc gattatcatg ttaatcagac acctgaatac ttctatcaat acaagggcca   4080
catgtgtctt aaagtcgtgg atgatggtga atttaaggac attattatca atgaaggaga   4140
atcgtttttg ctaccaggta atacgccaca tagtccagtg aggtttgctg atactattgg   4200
cttagtggtt gaacaggatc gtcctcaggg actgaatgac cgtattagat ggtattgtct   4260
gaattgcaag gaaatagtgc atgaaactga gttttactgc tctgatttgg gaacgcaagt   4320
gaaggacgca atcgtttcct ttgaaacgga tttagagaaa aggacatgca aaaattgtgg   4380
aacactgaac tattccaggc caaaataaaa cttttacggt aatattacgt tatgatttat   4440
gcaattaatg agttaagtag ctttatattt ctttcttatt tgattagttt cagctcaaca   4500
gctgactatt gaaccatttt tctaggcccct tctccctaat ctcaatgtgg ctaagactat   4560
ccaacttgat gatgacatta aagatcttga ggtaccgcag actggggaat ttgag         4615
```

<210> SEQ ID NO 40
<211> LENGTH: 869
<212> TYPE: PRT
<213> ORGANISM: Artificial Sequence
<220> FEATURE:
<223> OTHER INFORMATION: synthetic

<400> SEQUENCE: 40

```
Met Thr Ser Arg Thr Ala Glu Asn Pro Phe Asp Ile Glu Leu Gln Glu
 1               5                  10                  15

Asn Leu Ser Pro Arg Ser Ser Asn Ser Ser Ile Leu Glu Asn Ile Asn
            20                  25                  30

Glu Tyr Ala Arg Arg His Arg Asn Asp Ser Leu Ser Gln Glu Cys Asp
        35                  40                  45

Asn Glu Asp Glu Asn Glu Asn Leu Asn Tyr Thr Asp Asn Leu Ala Lys
    50                  55                  60

Phe Ser Lys Ser Gly Val Ser Arg Lys Ser Cys Met Leu Ile Phe Gly
65                  70                  75                  80

Ile Cys Phe Val Ile Trp Leu Phe Leu Phe Ala Leu Tyr Ala Arg Asp
                85                  90                  95

Asn Arg Phe Ser Asn Leu Asn Glu Tyr Val Pro Asp Ser Asn Ser His
            100                 105                 110

Gly Thr Ala Ser Ala Thr Thr Ser Ile Val Glu Pro Lys Gln Thr Glu
        115                 120                 125

Leu Pro Glu Ser Lys Asp Ser Asn Thr Asp Tyr Gln Lys Gly Ala Lys
    130                 135                 140

Leu Ser Leu Ser Gly Trp Arg Ser Gly Leu Tyr Asn Val Tyr Pro Lys
145                 150                 155                 160

Leu Ile Ser Arg Gly Glu Asp Asp Ile Tyr Tyr Glu His Ser Phe His
                165                 170                 175

Arg Ile Asp Glu Lys Arg Ile Thr Asp Ser Gln His Gly Arg Thr Val
            180                 185                 190

Phe Asn Tyr Glu Lys Ile Glu Val Asn Gly Ile Thr Tyr Thr Val Ser
        195                 200                 205

Phe Val Thr Ile Ser Pro Tyr Asp Ser Ala Lys Phe Leu Val Ala Cys
    210                 215                 220
```

```
Asp Tyr Glu Lys His Trp Arg His Ser Thr Phe Ala Lys Tyr Phe Ile
225                 230                 235                 240

Tyr Asp Lys Glu Ser Asp Gln Glu Asp Ser Phe Val Pro Val Tyr Asp
            245                 250                 255

Asp Lys Ala Leu Ser Phe Val Glu Trp Ser Pro Ser Gly Asp His Val
        260                 265                 270

Val Phe Val Phe Glu Asn Asn Val Tyr Leu Lys Gln Leu Ser Thr Leu
    275                 280                 285

Glu Val Lys Gln Val Thr Phe Asp Gly Asp Glu Ser Ile Tyr Asn Gly
290                 295                 300

Lys Pro Asp Trp Ile Tyr Glu Glu Val Leu Ser Asp Arg Ala
305                 310                 315                 320

Ile Trp Trp Asn Asp Asp Gly Ser Tyr Phe Thr Phe Leu Arg Leu Asp
                325                 330                 335

Asp Ser Asn Val Pro Thr Phe Asn Leu Gln His Phe Glu Glu Thr
            340                 345                 350

Gly Ser Val Ser Lys Tyr Pro Val Ile Asp Arg Leu Lys Tyr Pro Lys
        355                 360                 365

Pro Gly Phe Asp Asn Pro Leu Val Ser Leu Phe Ser Tyr Asn Val Ala
370                 375                 380

Lys Gln Lys Leu Glu Lys Leu Asn Ile Gly Ala Ala Val Ser Leu Gly
385                 390                 395                 400

Glu Asp Phe Val Leu Tyr Ser Leu Lys Trp Ile Asp Asn Ser Phe Phe
                405                 410                 415

Leu Ser Lys Phe Thr Asp Arg Thr Ser Lys Lys Met Glu Val Thr Leu
            420                 425                 430

Val Asp Ile Glu Ala Asn Ser Ala Ser Val Val Arg Lys His Asp Ala
        435                 440                 445

Thr Glu Tyr Asn Gly Trp Phe Thr Gly Glu Phe Ser Val Tyr Pro Val
            450                 455                 460

Val Gly Asp Thr Ile Gly Tyr Ile Asp Val Ile Tyr Tyr Glu Asp Tyr
465                 470                 475                 480

Asp His Leu Ala Tyr Tyr Pro Asp Cys Thr Ser Asp Lys Tyr Ile Val
                485                 490                 495

Leu Thr Asp Gly Ser Trp Asn Val Val Gly Pro Gly Val Leu Glu Val
            500                 505                 510

Leu Glu Asp Arg Val Tyr Phe Ile Gly Thr Lys Glu Ser Ser Met Glu
        515                 520                 525

His His Leu Tyr Tyr Thr Ser Leu Thr Gly Pro Lys Val Lys Ala Val
            530                 535                 540

Met Asp Ile Lys Glu Pro Gly Tyr Phe Asp Val Asn Ile Lys Gly Lys
545                 550                 555                 560

Tyr Ala Leu Leu Ser Tyr Arg Gly Pro Lys Leu Pro Tyr Gln Lys Phe
                565                 570                 575

Ile Asp Leu Ser Asp Pro Ser Thr Thr Ser Leu Asp Asp Ile Leu Ser
            580                 585                 590

Ser Asn Arg Gly Ile Val Glu Val Ser Leu Ala Thr His Ser Val Pro
        595                 600                 605

Val Ser Thr Tyr Thr Asn Val Thr Leu Glu Asp Gly Val Thr Leu Asn
    610                 615                 620

Met Ile Glu Val Leu Pro Ala Asn Phe Asn Pro Ser Lys Lys Tyr Pro
625                 630                 635                 640
```

Leu Leu Val Asn Ile Tyr Gly Gly Pro Gly Ser Gln Lys Leu Asp Val
            645                 650                 655

Gln Phe Asn Ile Gly Phe Glu His Ile Ile Ser Ser Leu Asp Ala
        660                 665                 670

Ile Val Leu Tyr Ile Asp Pro Arg Gly Thr Gly Gly Lys Ser Trp Ala
    675                 680                 685

Phe Lys Ser Tyr Ala Thr Glu Lys Ile Gly Tyr Trp Glu Pro Arg Asp
    690                 695                 700

Ile Thr Ala Val Val Ser Lys Trp Ile Ser Asp His Ser Phe Val Asn
705                 710                 715                 720

Pro Asp Lys Thr Ala Ile Trp Gly Trp Ser Tyr Gly Gly Phe Thr Thr
                725                 730                 735

Leu Lys Thr Leu Glu Tyr Asp Ser Gly Glu Val Phe Lys Tyr Gly Met
            740                 745                 750

Ala Val Ala Pro Val Thr Asn Trp Leu Leu Tyr Asp Ser Ile Tyr Thr
        755                 760                 765

Glu Arg Tyr Met Asn Leu Pro Lys Asp Asn Val Glu Gly Tyr Ser Glu
    770                 775                 780

His Ser Val Ile Lys Lys Val Ser Asn Phe Lys Asn Val Asn Arg Phe
785                 790                 795                 800

Leu Val Cys His Gly Thr Thr Asp Asp Asn Val His Phe Gln Asn Thr
                805                 810                 815

Leu Thr Leu Leu Asp Gln Phe Asn Ile Asn Gly Val Val Asn Tyr Asp
            820                 825                 830

Leu Gln Val Tyr Pro Asp Ser Glu His Ser Ile Ala His His Asn Ala
        835                 840                 845

Asn Lys Val Ile Tyr Glu Arg Leu Phe Lys Trp Leu Glu Arg Ala Phe
    850                 855                 860

Asn Asp Arg Phe Leu
865

<210> SEQ ID NO 41
<211> LENGTH: 771
<212> TYPE: DNA
<213> ORGANISM: Artificial Sequence
<220> FEATURE:
<223> OTHER INFORMATION: synthetic

<400> SEQUENCE: 41
ggaattcggc cttgggggcc tccaggactt gctgaaattt gctgactcat cttcgccatc      60
caaggataat gagttagcta atgtgacagt taatgagtcg tcttgactaa cggggaacat     120
ttcattattt atatccagag tcaatttgat agcagagttt gtggttgaaa tacctatgat     180
tcgggagact tgttgtaac gaccattatc cacagtttgg accgtgaaaa tgtcatcgaa      240
gagagcagac gacatattat ctattgtggt aagtgatagt tggaagtccg actaaggcat     300
gaaaatgaga agactgaaaa tttaaagttt ttgaaaacac taatcgggta ataacttgga     360
aattacgttt acgtgccttt agctcttgtc cttacccctg ataatctatc catttcccga     420
gagacaatga catctcggac agctgagaac ccgttcgata tagagcttca agagaatcta     480
agtccacgtt cttccaattc gtccatattg gaaaacatta tgagtatgc tagaagacat      540 cgcaatgatt cgctttccca agaatgtgat aatgaagatg agaacgaaaa tctcaattat     600
actgataact tggccaagtt ttcaaagtct ggagtatcaa gaaagagctg tatgctaata     660
tttggtattt gctttgttat ctggctgttt ctctttgcct tgtatgcgag ggacaatcga     720

```
tttttccaatt tgaacgagta cgttccagat tcaaacagct cgaggaattc c          771
```

<210> SEQ ID NO 42
<211> LENGTH: 949
<212> TYPE: DNA
<213> ORGANISM: Artificial Sequence
<220> FEATURE:
<223> OTHER INFORMATION: synthetic

<400> SEQUENCE: 42

```
gaagcttctc gagctactgg gaaccacgag acatcactgc agtagtttcc aagtggattt   60
cagatcactc atttgtgaat cctgacaaaa ctgcgatatg ggggtggtct tacggtgggt  120
tcactacgct taagacattg aatatgatt ctggagaggt tttcaaatat ggtatggctg   180
ttgctccagt aactaattgg cttttgtatg actccatcta cactgaaaga tacatgaacc  240
ttccaaagga caatgttgaa ggctacagtg aacacagcgt cattaagaag gtttccaatt  300
ttaagaatgt aaaccgattc ttggtttgtc acgggactac tgatgataac gtgcattttc  360
agaacacact aaccttactg gaccagttca atattaatgg tgttgtgaat tacgatcttc  420
aggtgtatcc cgacagtgaa catagcattg cccatcacaa cgcaaataaa gtgatctacg  480
agaggttatt caagtggtta gagcgggcat ttaacgatag attttttgtaa cattccgtac  540
ttcatgccat actatatatc ctgcaaggtt tcccttttcag acacaataat tgctttgcaa  600
ttttacatac caccaattgg caaaaataat ctcttcagta agttgaatgc ttttcaagcc  660
agcaccgtga gaaattgcta cagcgcgcat tctaacatca ctttaaaatt ccctcgccgg  720
tgctcactgg agtttccaac ccttagctta tcaaaatcgg gtgataactc tgagtttttt  780
ttttcacttc tattcctaaa ccttcgccca atgctaccac ctccaatcaa catcccgaaa  840
tggatagaag agaatggaca tctcttgcaa cctccggtta ataattactg tctccacaga  900
ggaggattta cggtaatgat tgtaggtggg cctaatgggc caagcttgc            949
```

<210> SEQ ID NO 43
<211> LENGTH: 1003
<212> TYPE: DNA
<213> ORGANISM: Artificial Sequence
<220> FEATURE:
<223> OTHER INFORMATION: synthetic

<400> SEQUENCE: 43

```
ggaattcggc cacctgggcc tgttgctgct ggtactgctg ttggaactgt tggtattgtt   60
gctgatctaa ggccgcctgt tccacaccgt gtgtatcgaa tgcttgggca aaatcatcgc  120
ctgccggagg ccccactacc gcttgttcct cctgctcttg tttgttttgc tcattgatga  180
tatcggcgtc aatgaattga tcctcaatcg tgtggtggtg gtgtcgtgat tcctcttctt  240
tcttgagtgc cttatccata ttcctatctt agtgtaccaa taattttgtt aaacacacgc  300
tgttgtttat gaaaagtcgt caaaaggtta aaaattctac ttggtgtgtg tcagagaaag  360
tagtgcagac ccccagtttg ttgactagtt gagaaggcgg ctcactattg cgcgaatagc  420
atgagaaatt tgcaaacatc tggcaaagtg gtcaatacct gccaacctgc caatcttcgc  480
gacggaggct gttaagcggg ttgggttccc aaagtgaatg gatattacgg gcaggaaaaa  540
cagccccttc cacactagtc tttgctactg acatcttccc tctcatgtat cccgaacaca  600
agtatcggga gtatcaacgg agggtgccct tatggcagta ctccctgttg gtgattgtac  660
tgctatacgg gtctcatttg cttatcagca ccatcaactt gatacactat aaccacaaaa  720
attatcatgc acacccagtc aatagtggta tcgttcttaa tgagtttgct gatgacgatt  780
```

| cattctcttt gaatggcact ctgaacttgg agaactggag aaatggtacc ttttccccta | 840 |
| aatttcattc cattcagtgg accgaaatag gtcaggaaga tgaccaggga tattacattc | 900 |
| tctcttccaa ttcctcttac atagtaaagt ctttatccga cccagacttt gaatctgttc | 960 |
| tattcaacga gtctacaatc acttacaacg ctcgaggaat tcg | 1003 |

<210> SEQ ID NO 44
<211> LENGTH: 1142
<212> TYPE: DNA
<213> ORGANISM: Artificial Sequence
<220> FEATURE:
<223> OTHER INFORMATION: synthetic

<400> SEQUENCE: 44

| gaagcttctc gagggcagca aagccttacg ttgatgagaa tagactggcc atttggggtt | 60 |
| ggtcttatgg aggttacatg acgctaaagg ttttagaaca ggataaaggt gaaacattca | 120 |
| aatatggaat gtctgttgcc cctgtgacga attggaaatt ctatgattct atctacacag | 180 |
| aaagatacat gcacactcct caggacaatc caaactatta taattcgtca atccatgaga | 240 |
| ttgataattt gaagggagtg aagaggttct tgctaatgca cggaactggt gacgacaatg | 300 |
| ttcacttcca aaatacactc aaagttctag atttatttga tttacatggt cttgaaaact | 360 |
| atgatatcca cgtgttccct gatagtgatc acagtattag atatcacaac ggtaatgtta | 420 |
| tagtgtatga taagctattc cattggatta ggcgtgcatt caaggctggc aaataaatag | 480 |
| gtgcaaaaat attattagac tttttttttc gttcgcaagt tattactgtg taccataccg | 540 |
| atccaatccg tattgtaatt catgttctag atccaaaatt tgggactcta attcatgagg | 600 |
| tctaggaaga tgatcatctc tatagttttc agcggggggc tcgatttgcg gttggtcaaa | 660 |
| gctaacatca aaatgtttgt caggttcagt gaatggtaac tgctgctctt gaattggtcg | 720 |
| tctgacaaat tctctaagtg atagcacttc atctacaatc atttgcttca tcgtttctat | 780 |
| atcgtccacg acctcaaacg agaaatcgaa tttggaagaa cagacgggct catcgttagg | 840 |
| atcatgccaa accttgagat atggatgctc taaagcctca gtaactgtaa ttctgtgagt | 900 |
| gggatctacc gtgagcattc gatccagtaa gtctatcgct tcagggttgg caccgggaaa | 960 |
| taactggctg aatgggatct tgggcatgaa tggcagggag cgaacataat cctgggcacg | 1020 |
| ctctgatctg atagactgaa gtgtctcttc cgaaacagta cccagcgtac tcaaaatcaa | 1080 |
| gttcaattga tccacatagt ctcttcctct aaaaatgggt cggccaccta ggccaagctt | 1140 |
| gc | 1142 |

<210> SEQ ID NO 45
<211> LENGTH: 1202
<212> TYPE: DNA
<213> ORGANISM: Artificial Sequence
<220> FEATURE:
<223> OTHER INFORMATION: synthetic

<400> SEQUENCE: 45

| tgtttagctt gcctcgtccc cgccgggtca cccggccagc gacatggagg cccagaatac | 60 |
| cctccttgac agtcttgacg tgcgcagctc aggggcatga tgtgactgtc gcccgtacat | 120 |
| ttagcccata catccccatg tataatcatt tgcatccata cattttgatg gccgcacggc | 180 |
| gcgaagcaaa aattacggct cctcgctgca gacctgcgag cagggaaacg ctcccctcac | 240 |
| agacgcgttg aattgtcccc acgccgcgcc cctgtagaga aatataaaag gttaggattt | 300 |

```
gccactgagg ttcttctttc atatacttcc ttttaaaatc ttgctaggat acagttctca    360
catcacatcc gaacataaac aaccatgggt accactcttg acgacacggc ttaccggtac    420
cgcaccagtg tcccggggga cgccgaggcc atcgaggcac tggatgggtc cttcaccacc    480
gacaccgtct tccgcgtcac cgccaccggg acggcttca ccctgcggga ggtgccggtg     540
gacccgcccc tgaccaaggt gttccccgac gacgaatcgg acgacgaatc ggacgacggg    600
gaggacggcg acccggactc ccggacgttc gtcgcgtacg gggacgacgg cgacctggcg    660
ggcttcgtgg tcgtctcgta ctccggctgg aaccgccggc tgaccgtcga ggacatcgag    720
gtcgccccgg agcaccgggg gcacggggtc gggcgcgcgt tgatggggct cgcgacggag    780
ttcgcccgcg agcggggcgc cgggcacctc tggctggagg tcaccaacgt caacgcaccg    840
gcgatccacg cgtaccggcg gatggggttc accctctgcg gcctggacac cgccctgtac    900
gacggcaccg cctcggacgg cgagcaggcg ctctacatga gcatgccctg ccctaatca    960
gtactgacaa taaaaagatt cttgttttca agaacttgtc atttgtatag tttttttata   1020
ttgtagttgt tctattttaa tcaaatgtta gcgtgattta tattttttt cgcctcgaca    1080
tcatctgccc agatgcgaag ttaagtgcgc agaaagtaat atcatgcgtc aatcgtatgt   1140
gaatgctggt cgctatactg ctgtcgattc gatactaacg ccgccatcca gtgtcgaaaa   1200
cg                                                                  1202
```

<210> SEQ ID NO 46
<211> LENGTH: 42
<212> TYPE: PRT
<213> ORGANISM: Artificial Sequence
<220> FEATURE:
<223> OTHER INFORMATION: synthetic

<400> SEQUENCE: 46

Gly Leu Glu Asn Tyr Asp Ile His Val Phe Pro Asp Ser Asp His Ser
 1               5                  10                  15

Ile Arg Tyr His Asn Gly Asn Val Ile Val Tyr Asp Lys Leu Phe His
            20                  25                  30

Trp Ile Arg Arg Ala Phe Lys Ala Gly Lys
        35                  40

<210> SEQ ID NO 47
<211> LENGTH: 17
<212> TYPE: PRT
<213> ORGANISM: Artificial Sequence
<220> FEATURE:
<223> OTHER INFORMATION: synthetic

<400> SEQUENCE: 47

Gly Leu Glu Asn Tyr Asp Ile His Val Phe Pro Asp Thr Ile Pro Leu
 1               5                  10                  15

Asp

<210> SEQ ID NO 48
<211> LENGTH: 21
<212> TYPE: DNA
<213> ORGANISM: Artificial Sequence
<220> FEATURE:
<223> OTHER INFORMATION: synthetic

<400> SEQUENCE: 48
cgttttcgac actggatggc g                                              21

<210> SEQ ID NO 49
<211> LENGTH: 21
<212> TYPE: DNA
<213> ORGANISM: Artificial Sequence
<220> FEATURE:
<223> OTHER INFORMATION: synthetic

<400> SEQUENCE: 49
cgttttcgac actggatggc g                                         21

<210> SEQ ID NO 50
<211> LENGTH: 763
<212> TYPE: DNA
<213> ORGANISM: Artificial Sequence
<220> FEATURE:
<223> OTHER INFORMATION: synthetic

<400> SEQUENCE: 50
aattcggcct tggggcctc caggacttgc tgaaatttgc tgactcatct tcgccatcca     60
aggataatga gttagctaat gtgacagtta atgagtcgtc ttgactaacg ggaacattt    120 cattatttat atccagagtc aatttgatag cagagtttgt ggttgaaata cctatgattc   180
gggagacttt gttgtaacga ccattatcca cagtttggac cgtgaaaatg tcatcgaaga   240
gagcagacga catattatct attgtggtaa gtgatagttg gaagtccgac taaggcatga   300
aaatgagaag actgaaaatt taagttttt gaaaacacta atcgggtaat aacttggaaa    360
ttacgtttac gtgcctttag ctcttgtcct taccctgat aatctatcca tttcccgaga    420
gacaatgaca tctcggacag ctgagaaccc gttcgatata gagcttcaag agaatctaag   480
tccacgttct tccaattcgt ccatattgga aacattaat gagtatgcta aagacatcg     540 caatgattcg ctttcccaag aatgtgataa tgaagatgag aacgaaaatc tcaattatac   600
tgataacttg gccaagtttt caaagtctgg agtatcaaga aagagctgta tgctaatatt   660
tggtatttgc tttgttatct ggctgtttct ctttgccttg tatgcgaggg acaatcgatt   720
ttccaatttg aacgagtacg ttccagattc aaacagctcg agg                    763

<210> SEQ ID NO 51
<211> LENGTH: 940
<212> TYPE: DNA
<213> ORGANISM: Artificial Sequence
<220> FEATURE:
<223> OTHER INFORMATION: synthetic

<400> SEQUENCE: 51
agcttctcga gctactggga accacgagac atcactgcag tagtttccaa gtggatttca     60
gatcactcat ttgtgaatcc tgacaaaact gcgatatggg ggtggtctta cggtgggttc   120
actacgctta agacattgga atatgattct ggagaggttt tcaaatatgg tatggctgtt   180
gctccagtaa ctaattggct tttgtatgac tccatctaca ctgaaagata catgaacctt   240
ccaaaggaca tgttgaagg ctacagtgaa cacagcgtca ttaagaaggt ttccaatttt    300
aagaatgtaa accgattctt ggtttgtcac gggactactg atgataacgt gcattttcag   360
aacacactaa ccttactgga ccagttcaat attaatggtg ttgtgaatta cgatcttcag   420
gtgtatcccg acagtgaaca tagcattgcc catcacaacg caaataaagt gatctacgag   480
aggttattca gtggttaga gcgggcattt aacgatagat ttttgtaaca ttccgtactt    540
catgccatac tatatatcct gcaaggtttc cctttcagac acaataattg ctttgcaatt   600
ttacatacca ccaattggca aaaataatct cttcagtaag ttgaatgctt ttcaagccag   660

```
caccgtgaga aattgctaca gcgcgcattc taacatcact ttaaaattcc ctcgccggtg    720
ctcactggag tttccaaccc ttagcttatc aaaatcgggt gataactctg agttttttt     780 ttcacttcta ttcctaaacc ttcgcccaat gctaccacct ccaatcaaca tcccgaaatg    840
gatagaagag aatggacatc tcttgcaacc tccggttaat aattactgtc tccacagagg    900
aggatttacg gtaatgattg taggtgggcc taatgggcca                         940
```

<210> SEQ ID NO 52
<211> LENGTH: 995
<212> TYPE: DNA
<213> ORGANISM: Artificial Sequence
<220> FEATURE:
<223> OTHER INFORMATION: synthetic

<400> SEQUENCE: 52

```
aattcggcca cctgggcctg ttgctgctgg tactgctgtt ggaactgttg gtattgttgc     60
tgatctaagg ccgcctgttc cacaccgtgt gtatcgaatg cttgggcaaa atcatcgcct    120
gccggaggcc ccactaccgc ttgttcctcc tgctcttgtt tgttttgctc attgatgata    180
tcggcgtcaa tgaattgatc ctcaatcgtg tggtggtggt gtcgtgattc ctcttctttc    240
ttgagtgcct tatccatatt cctatcttag tgtaccaata attttgttaa acacacgctg    300
ttgtttatga aaagtcgtca aaaggttaaa aattctactt ggtgtgtgtc agagaaagta    360
gtgcagaccc ccagtttgtt gactagttga aaggcggct cactattgcg cgaatagcat    420
gagaaatttg caaacatctg gcaaagtggt caatacctgc caacctgcca atcttcgcga    480
cggaggctgt taagcgggtt gggttcccaa agtgaatgga tattacgggc aggaaaaaca    540
gccccttcca cactagtctt tgctactgac atcttccctc tcatgtatcc gaacacaag     600 tatcgggagt atcaacggag ggtgccctta tggcagtact ccctgttggt gattgtactg    660
ctatacgggt ctcatttgct tatcagcacc atcaacttga tacactataa ccacaaaaat    720
tatcatgcac acccagtcaa tagtggtatc gttcttaatg agtttgctga tgacgattca    780
ttctctttga atggcactct gaacttggag aactggagaa atggtaccct tcccctaaa     840 tttcattcca ttcagtggac cgaaataggt caggaagatg accagggata ttacattctc    900
tcttccaatt cctcttacat agtaaagtct ttatccgacc cagactttga atctgttcta    960
ttcaacgagt ctacaatcac ttacaacgct cgagg                              995
```

<210> SEQ ID NO 53
<211> LENGTH: 1133
<212> TYPE: DNA
<213> ORGANISM: Artificial Sequence
<220> FEATURE:
<223> OTHER INFORMATION: synthetic

<400> SEQUENCE: 53

```
agcttctcga gggcagcaaa gccttacgtt gatgagaata gactggccat ttggggttgg     60
tcttatggag gttacatgac gctaaaggtt ttagaacagg ataaaggtga acattcaaa    120 tatggaatgt ctgttgcccc tgtgacgaat tggaaattct atgattctat ctacacagaa    180
agatacatgc acactcctca ggacaatcca aactattata attcgtcaat ccatgagatt    240
gataatttga agggagtgaa gaggttcttg ctaatgcacg gaactggtga cgacaatgtt    300
cacttccaaa atacactcaa agttctagat ttatttgatt tacatggtct tgaaaactat    360
gatatccacg tgttccctga tagtgatcac agtattagat atcacaacgg taatgttata    420
gtgtatgata agctattcca ttggattagg cgtgcattca aggctggcaa ataaataggt    480
```

```
gcaaaaatat tattagactt ttttttttcgt tcgcaagtta ttactgtgta ccataccgat      540
ccaatccgta ttgtaattca tgttctagat ccaaaatttg ggactctaat tcatgaggtc      600
taggaagatg atcatctcta tagttttcag cgggggggctc gatttgcggt tggtcaaagc     660
taacatcaaa atgtttgtca ggttcagtga atggtaactg ctgctcttga attggtcgtc     720
tgacaaattc tctaagtgat agcacttcat ctacaatcat ttgcttcatc gtttctatat     780
cgtccacgac ctcaaacgag aaatcgaatt tggaagaaca gacgggctca tcgttaggat     840
catgccaaac cttgagatat ggatgctcta aagcctcagt aactgtaatt ctgtgagtgg     900
gatctaccgt gagcattcga tccagtaagt ctatcgcttc agggttggca ccgggaaata     960
actggctgaa tgggatcttg gcatgaatg gcagggagcg aacataatcc tgggcacgct     1020
ctgatctgat agactgaagt gtctcttccg aaacagtacc cagcgtactc aaaatcaagt    1080
tcaattgatc cacatagtct cttcctctaa aaatgggtcg gccacctagg cca            1133

<210> SEQ ID NO 54
<211> LENGTH: 1202
<212> TYPE: DNA
<213> ORGANISM: Artificial Sequence
<220> FEATURE:
<223> OTHER INFORMATION: synthetic

<400> SEQUENCE: 54
tgtttagctt gcctcgtccc cgccgggtca cccggccagc gacatggagg cccagaatac      60
cctccttgac agtcttgacg tgcgcagctc aggggcatga tgtgactgtc gcccgtacat     120
ttagcccata catccccatg tataatcatt tgcatccata cattttgatg gccgcacggc     180
gcgaagcaaa aattacggct cctcgctgca gacctgcgag cagggaaacg ctcccctcac     240
agacgcgttg aattgtcccc acgccgcgcc cctgtagaga aatataaaag gttaggattt     300
gccactgagg ttcttctttc atatacttcc ttttaaaatc ttgctaggat acagttctca     360
catcacatcc gaacataaac aaccatgggt accactcttg acgacacggc ttaccggtac     420
cgcaccagtg tcccggggga cgccgaggcc atcgaggcac tggatgggtc cttcaccacc     480
gacaccgtct tccgcgtcac cgccaccggg gacggcttca ccctgcggga ggtgccggtg     540
gacccgcccc tgaccaaggt gttccccgac gacgaatcgg acgacgaatc ggacgacggg     600
gaggacggcg acccggactc ccggacgttc gtcgcgtacg gggacgacgg cgacctggcg     660
ggcttcgtgg tcgtctcgta ctccggctgg aaccgccggc tgaccgtcga ggacatcgag     720
gtcgccccgg agcaccgggg gcacggggtc gggcgcgcgt tgatggggct cgcgacggag     780
ttcgcccgcg agcggggcgc cgggcacctc tggctggagg tcaccaacgt caacgcaccg     840
gcgatccacg cgtaccggcg gatgggggttc accctctgcg gcctggacac cgccctgtac    900
gacggcaccg cctcggacgg cgagcaggcg ctctacatga gcatgccctg cccctaatca     960
gtactgacaa taaaaagatt cttgtttca agaacttgtc atttgtatag tttttttata     1020
ttgtagttgt tctattttaa tcaaatgtta gcgtgattta tatttttttt cgcctcgaca    1080
tcatctgccc agatgcgaag ttaagtgcgc agaaagtaat atcatgcgtc aatcgtatgt     1140
gaatgctggt cgctatactg ctgtcgattc gatactaacg ccgccatcca gtgtcgaaaa    1200
cg                                                                   1202
```

METHOD FOR PRODUCING THERAPEUTIC PROTEINS IN *PICHIA PASTORIS* LACKING DIPEPTIDYL AMINOPEPTIDASE ACTIVITY

CROSS REFERENCE TO RELATED APPLICATIONS

This application is the U.S. National stage filing under 35 U.S.C. §371 of International Patent Application No. PCT/US2010/054183 filed Oct. 27, 2010, which claims benefit of U.S. Provisional Application No. 61/256,369 filed Oct. 30, 2009, the disclosures of which are hereby incorporated by reference in their entireties.

FIELD OF THE INVENTION

The present invention is directed to methods and compositions for the production of glycoproteins in yeast cell lines having no dipeptidyl aminopeptidase (DAP) activity, which are useful as human or animal therapeutic agents.

BACKGROUND OF THE INVENTION

Yeast are important production platforms for the generation of recombinant proteins. In that yeasts are eukaryotes, they share common evolutionary processes with those of higher eukaryotes, including many of the post-translational modifications that occur in the secretory pathway. Recent advances in glycoengineering have resulted in cell lines of the yeast strain *Pichia pastoris* with genetically modified glycosylation pathways that allow them to carry out a sequence of enzymatic reactions, which mimic the process of glycoproteins in humans. See, for example, U.S. Pat. Nos. 7,029,872 and 7,326,681 that describe methods for producing a recombinant glycoprotein in a lower eukaryote host cell that are substantially identical to their human counterparts. Human-like sialylated bi-antennary complex N-linked glycans like those produced in *Pichia pastoris* from the aforesaid methods have demonstrated utility for the production of therapeutic glycoproteins.

Similar to higher eukaryotes, yeast also express numerous proteases, many of which are either localized to the secretory pathway or pass through it on route to their final destination. As a consequence, non-desirable proteolysis of some recombinant proteins may occur with the specific cleavage being dependent on the class of protease involved. Dipeptidyl aminopeptidases (DAPs) are a class of proteolytic enzymes which remove a two amino acid peptide from the N-terminus of a protein. In *Saccharomyces cerevisiae* genes for the enzymes STE13 and DAP2 have been identified as having DAP activity, see, Julius et al., *Cell*, 32: 839-852, 1983; Rendueles et al., *J. Bacteriology*, 169: 4041-4048, 1987. Applicants herein have developed methods for the elimination of DAP activity in *Pichia pastoris*, which will allow for the production of full length therapeutic proteins.

SUMMARY OF THE INVENTION

In one embodiment the invention herein is a method for producing therapeutic proteins in yeast cell lines lacking dipeptidyl aminopeptidase (DAP) activity. This embodiment comprises transforming a genetically modified *Pichia pastoris* cell line in which the DAP activity has been eliminated with a polynucleotide vector encoding the therapeutic protein and culturing the transformed host cell to produce the therapeutic protein. DAP activity can be eliminated by modifying a *Pichia pastoris* cell line such that STE13, DAP2, and DPPIII have been deleted or disrupted. In another embodiment DAP activity is eliminated by modifying a *Pichia pastoris* cell line such that STE13 and DAP2 have been deleted or disrupted.

In one embodiment, the invention is a genetically modified yeast cell line lacking DAP activity that can be used for the production of therapeutic proteins comprising a *Pichia pastoris* cell line that has been recombinantly modified through the deletion of STE13 and DAP2.

In still other embodiments, the invention is a method for the production of therapeutic proteins from *Pichia pastoris*, such as TNFRII-Fc, a recombinant fusion protein comprising the ectodomain of tumor necrosis factor receptor 2 (TNFRII) fused to an IgG1 Fc domain (TNFRII-Fc), or a recombinant granulocyte colony-stimulating factor (GCSF) polypeptide, comprising the secreted plasma form of GCSF.

BRIEF DESCRIPTION OF THE DRAWINGS

FIG. 2 is a graphic depiction of the N-terminal cleavage of TNFRII-Fc associated with DAP activity in yeast. FIG. 2A shows the seven N-terminal amino acids (SEQ ID NO: 1) of intact secreted TNFRII-Fc (SEQ ID NO: 3) and FIG. 2B shows the five N-terminal amino acids (SEQ ID NO: 2) of the truncated product. The arrow illustrates the cleavage site recognized by both of the dipeptidyl aminopeptidases, Dap2p and Ste13p.

FIG. 3 is the amino acid sequence for the fusion protein, TNFRII-Fc, comprising tumor necrosis factor receptor 2 (TNFRII) and an IgG1 Fc region (Fc) (SEQ ID NO: 3).

FIG. 4 is a graphic depiction of the N-terminal cleavage of GCSF associated with DAP activity in yeast. FIG. 4A shows the seven N-terminal amino acids (SEQ ID NO: 4) of intact secreted GCSF (SEQ ID NO: 6) and FIG. 4B shows the five N-terminal amino acids (SEQ ID NO: 5) of the truncated product. The arrow illustrates the cleavage site recognized by both of the dipeptidyl aminopeptidases, Dap2p and Ste13p.

FIG. 5 is the amino acid sequence for a recombinant granulocyte colony-stimulating factor (GCSF) protein (SEQ ID NO: 6).

FIG. 7C represents a flow diagram for the single knockout glycoengineered strains, ste13 (YGLY8084) and dap2 (YGLY8090), as well as the subsequent double knock-out strain (YGLY8096).

FIGS. 8A and 8B are the cDNA (SEQ ID NO: 37) and amino acid (SEQ ID NO: 38) sequences for *Pichia pastoris* DAP2. ORF is shown in boldface type, +/−approximately 1 kb flanking sequence.

FIGS. 9A and 9B are the cDNA (SEQ ID NO: 39) and amino acid (SEQ ID NO: 40) sequences for *Pichia pastoris* STE13. ORF is shown in boldface type, +/−approximately 1 kb flanking sequence.

FIGS. 10A and 10B are the 5' (SEQ ID NO: 41) and 3' (SEQ ID NO: 42) DNA flanking regions for PpSTE13 amplified to generate pGLY4511 and pGLY4512, respectively. The flanking regions (underlined) are themselves flanked by nucleotides constituting EcoRI restriction sites for the PpSTE13 5' flanking region or nucleotides constituting HindIII restriction sites for the PpSTE13 3' flanking region.

FIGS. 11A and 11B are the 5' (SEQ ID NO: 43) and 3' (SEQ ID NO: 44) DNA flanking regions for PpDAP2 amplified to generate pGLY4513 and pGLY4514, respectively. The flanking regions (underlined) are themselves flanked by nucleotides constituting EcoRI restriction sites for the PpDAP2 5' flanking region or nucleotides constituting HindIII restriction sites for the PpDAP2 3' flanking region.

FIG. 12 is the cDNA sequence for a nourseothricin marker cassette (SEQ ID NO: 45) amplified from pAG25, with the ORF shown in boldface type.

FIG. 13 is the cDNA (SEQ ID NO: 54) sequence for the *Pichia pastoris* DPPIII. ORF is shown in boldface type, +/−approximately 1 kb flanking sequence.

DETAILED DESCRIPTION OF THE INVENTION

Definitions

Figure 1A:
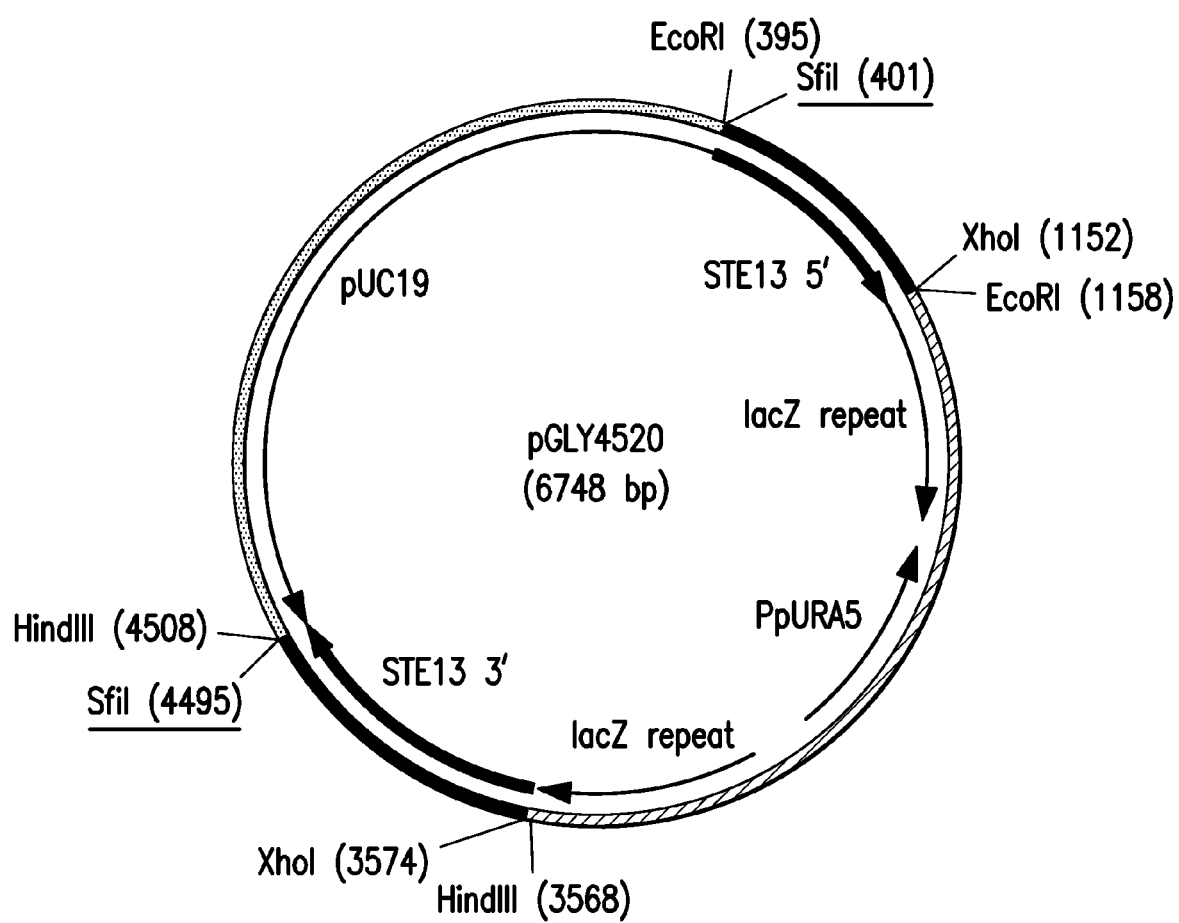
FIG. 1 is a graphic representation of the vectors used in the methods herein. The Ura5 marked PpSTE13 and PpDAP2 knockout vectors are shown as pGLY4520 and pGLY4521 in FIGS. 1A and 1B, respectively. The PpSTE13 and PpDAP2 nourseothricin marked vectors are shown as pGLY5018 and pGLY5019 in FIGS. 1C and 1D, respectively. The SfiI restriction sites used to excise the knockout fragments used in the transformations are underlined. PpSTE13 and PpDAP2 flanking regions are highlighted in black.

As used herein the term "dipeptidyl aminopeptidase activity" or "DAP activity" refers to the enzymatic cleavage of a polypeptide produced by the genes designated STE13, DAP2, or DPPIII.

As used herein the phrase "elimination of dipeptidyl aminopeptidase activity" or "elimination of DAP activity" refers to the absence of the enzymatic activity produced by the genes designated STE13, DAP2, and DPPIII.

The term "therapeutic protein" as used herein refers to a full length, i.e. non-truncated form, biologically active polypeptide than can be utilized as a therapeutic to treat a disease or condition in an animal or human. Examples of this term as used herein are the fusion protein TNFRII-Fc, which comprises the tumor necrosis factor receptor 2 (TNFRII) and the Fc region of IgG1 (Fc), and a recombinant granulocyte colony-stimulating factor (GCSF) protein.

The term "N-terminal recognition site" as used herein refers to a polypeptide having an N-terminal sequence of the motif X-Pro or X-Ala, where X is any amino acid and the second position relative to the N-terminal is either a proline or an alanine.

The term "glycoengineered *Pichia pastoris* strain" as used herein refers to a *Pichia pastoris* strain that has been engineered to express human glycoproteins. Representative strains include YJN201 (Choi et al., *PNAS*, 100 (9): 5022-5027, 2003); YSH44 (Hamilton et al., *Science*, 301 (5637): 1244-1246, 2003); RDP36-1 (Davidson et al., *Glycobiology*, 14 (4): 1-9, 2004); PBP6-5 (Bobrowicz et al., *Glycobiology*, 14 (9): 757-766, 2004); YSH597 (Hamilton et al., *Science*, 313 (5792): 1441-1443, 2006).

The term "wild type strain" as used herein refers to a glycoengineered *Pichia pastoris* strain in which the genes, STE13, DAP2, or DPPIII have not been altered, disrupted or deleted from the genome.

The term "deletion strain" as used herein refers to a glycoengineered *Pichia pastoris* strain in which the *Pichia pastoris* homologue of one, two or all DAP genes, i.e. STE13, and DAP2, and DPPIII, have been modified at the genomic level to eliminate functional DAP activity. This includes, but is not limited to, complete or partial deletion of the gene (comprising the promoter, open reading frame and terminator); introduction of one or more mutations that alter transcription or translation of the gene or encoded mRNA, respectively; and introduction of one or more mutations that inactivate the protein activities. An example of such a deletion strain is YGLY8084.

The term "deleted or disrupted" and "deletion or disruption" as used herein refers to the inhibition of the activity of an enzyme, said enzyme produced from a yeast cell genome, in which the inhibition of the enzyme activity is to the extent that a substrate protein has an intact N-terminus. Examples of which are yeast host cells in which enzyme activity can be abrogated or disrupted including, but not limited to, 1) deletion or disruption of the upstream or downstream regulatory sequences controlling expression of the gene; 2) mutation of the gene encoding the enzyme activity to render the gene non-functional, where "mutation" includes deletion, substitution, insertion, or addition into the gene to render it incapable of enzymatic activity; 3) abrogation or disruption of the enzymatic activity by means of a chemical, peptide, or protein inhibitor; 4) abrogation or disruption of the enzymatic activity by means of nucleic acid-based expression inhibitors, such as antisense DNA and siRNA; 5) abrogation or disruption of the enzymatic activity by means of transcription inhibitors or inhibitors of the expression or activity of regulatory factors that control or regulate expression of the gene encoding the enzyme activity; and 6) by any means in which the product obtained, even if expressed, is not identical to the secreted protein and the function is attenuated.

ABBREVIATIONS

The following abbreviations are used throughout this description:
URA5 Orotate phosphoribosyltransferase (OPRTase) isozyme
ScSUC2 *S. cerevisiae* Invertase
OCH1 Alpha-1,6-mannosyltransferase
K1GlcNAcTr *K lactis* UDP-GlcNAc transporter
BMT2: Beta-mannose-transfer (beta-mannose elimination)
MNN4B: MNN4A-like gene (charge elimination)
MmGlcNAcTr Mouse homologue of UDP-GlcNAc transporter
PNO1: Phosphomannosylation of N-glycans (charge elimination)
MNN4A: Mannosyltransferase (charge elimination)
ADE1 N-succinyl-5-aminoimidazole-4-carboxamide ribotide synthetase
MNS1 Mouse mannosidase IA catalytic domain fused to ScSEC12 leader
GnTI Human GlcNAc transferase I catalytic domain fused to PpSEC12 leader
HIS1 ATP phosphoribosyltransferase
GalTI Truncated human galactosyltransferase I catalytic domain fused to ScKRE2 leader
GalE *S. cerevisiae* UDP-glucose 4-epimerase UDP-GalTr UDP-Galactose transporter
ARG1 Arginosuccinate synthetase
MNSII *Drosophila* mannosidase II catalytic domain fused to ScMNN2 leader
GnTII Rat GlcNAc transferase II catalytic domain fused to ScMNN2 leader
PRO1 Gamma-glutamyl kinase
TrMNS1 Secreted *T. reesei* mannosidase I catalytic domain fused to ScaMAT
AOX1 Alcohol oxidase I
TNFRII-Fc Human Tumour Necrosis Factor Receptor II fused to Fc domain of IgG1
Zeo Zeocin resistance marker
STE13 Dipeptidyl aminopeptidase
DAP2 Dipeptidyl aminopeptidase
DPPIII Dipeptidyl aminopeptidase
Nat Nourseothricin resistance marker Production of Therapeutic Proteins in Yeast A significant fraction of proteins isolated from humans or other animals are glycosylated. Among proteins used therapeutically about 70% are glycosylated. If a therapeutic protein is produced in a microorganism host such as yeast and is glycosylated utilizing an endogenous pathway, typically its therapeutic efficiency is greatly reduced. Notwithstanding, such glycoproteins can be immunogenic in humans, and demonstrate reduced half-lives in vivo after administration, Takeuchi, *Trends in Glycoscience and Glycotechnology*, 9: S29-S35, 1997.

Specific receptors in humans and animals can recognize terminal mannose residues and promote the rapid clearance of the protein from the bloodstream. Additional adverse effects may include changes in protein folding, solubility, susceptibility to proteases, trafficking, transport, compartmentalization, secretion, recognition by other proteins or factors, antigenicity, or allergenicity. Accordingly, it has been necessary to produce therapeutic glycoproteins in animal host systems, so that the pattern of glycosylation is identical or at least similar to that occurring in humans or in the intended recipient species. In most cases a mammalian host system, such as mammalian cell culture, is used. Systems used have included Chinese hamster ovary cells (CHO), transgenic animals, plants, or insect cells. Recombinant human proteins expressed in such systems may still include non-human glycoforms, Raju et al., *Annals Biochem.*, 283(2): 123-132, 2000. All of these systems have significant drawbacks, including but not limited to, that only certain therapeutic proteins are suitable for expression in animal or plant systems, that the cell culture systems are typically very slow, that protein yields are low relative to microbial fermentation processes and may require complex and expensive nutrients or additives, or that such systems may be susceptible to contamination.

The lack of a suitable expression is thus an obstacle to the production of any therapeutic glycoprotein. Production of glycoproteins via the fermentation of microorganisms would offer advantages over the existing systems including, but not limited to, rapid production of high concentrations of protein, the ability to use sterile, well-controlled production conditions or chemically defined growth media, the ability to express a wide variety of proteins and easy recovery of the therapeutic protein. However, as noted above, bacterial systems do not produce glycosylated therapeutic proteins like eukaryotes. To that end, yeast cell lines and in particular, *Pichia pastoris*, with genetically modified glycosylation pathways that produce human glycoproteins have been developed. See, for example, U.S. Pat. Nos. 7,029,872 and 7,326,681 and US 2006-0286637 that describe methods for producing recombinant glycoproteins in a lower eukaryote host cell that are substantially identical to their human counterparts. Human-like sialylated bi-antennary complex N-linked glycans like those produced in *Pichia pastoris* from the aforesaid methods have demonstrated utility for the production of therapeutic glycoproteins.

While the aforesaid *Pichia pastoris* cell lines can produce proteins having a human-like glycosylation pattern making them appropriate for use as therapeutics, expression of therapeutic proteins in *Pichia pastoris* does not necessarily result in the production of the full length polypeptide. Non-desirable enzymatic activity, such as proteolysis that truncates the therapeutic protein, needs to be eliminated in order to use the yeast expression system efficiently.

Methods for Producing Therapeutic Proteins in *Pichia* Lacking Dipeptidyl Aminopeptidase Activity Analysis of the peptide sequence of a recombinant fusion protein INFRII-Fc, the sequence of which is shown in FIG. 3 (SEQ ID NO: 3), secreted from the yeast cell line, *Pichia pastoris*, indicated that all of the peptide produced had been truncated at the N-terminus by two amino acids. Applicants herein identified that the deletion of two genes, STE13 and DAP2, in a *Pichia pastoris* cell line eliminated all DAP activity and resulted in the production full length TNFRII-Fc. Applicants have also identified that *Pichia pastoris* has a third dipeptidyl aminopeptidase, DPPIII. Thus, in one embodiment the invention herein is a method for producing therapeutic proteins in yeast cell lines lacking DAP activity. This embodiment comprises transforming a genetically modified *Pichia pastoris* cell line, in which the DAP activity has been eliminated, with a polynucleotide vector encoding a therapeutic protein and culturing the transformed host cell to produce the therapeutic protein. DAP activity is eliminated by modifying the *Pichia pastoris* cell line such that STE13 and DAP2 and/or DPPIII have been deleted or disrupted. In a specific embodiment of the invention herein, DAP activity was eliminated by modifying the *Pichia pastoris* cell line such that STE13 and DAP2 have been deleted or disrupted.

In another embodiment, the invention is a yeast cell line used for the production of therapeutic proteins which comprises a *Pichia pastoris* cell line that has been recombinantly modified such that the STE13 and DAP2 genes were deleted or disrupted and all resultant DAP activity was eliminated.

In still other embodiments, the invention is a method for the production from *Pichia pastoris* of a therapeutic protein having the amino acid proline or alanine in the second position relative to the N-terminus of the polypeptide, such as the TNFRII-Fc fusion protein or the GCSF protein described herein.

Dipeptidyl Aminopeptidase Activity

Genes that are associated with dipeptidyl aminopeptidase (DAP) activity, a subclass of proteases known to truncate two amino acids from the amino terminus of a polypeptide, have been identified in yeast. Non-mating alpha-cell mutants of *S. cerevisiae* have been characterized and mutations in the dipeptidyl aminopeptidase gene STE13, have been attributed to incomplete processing of the alpha mating factor pheromone, Julius et al., *Cell*, 32(3), 839-52, 1983. Furthermore, a second dipeptidyl peptidase, Dap2p, was identified by screening *S. cerevisiae* mutant strains deficient in Step 13p activity, Suarez Rendueles and Wolf, *Journal of Bacteriology*, 169 (9), 4041-48, 1987. It has also been reported that knockout of the *Pichia* homolog of *S. cerevisiae* STE13 prevents in vivo proteolytic cleavage of proteins having the amino acids HG (His-Gly) at the N-terminus and allowed production of a full length insulinotropic peptide, Melarkode et al., WO 2007/148345; Prabha et al., *Protein Expression and Purification*, 64, 155-161, 2009. Conversely, disruption of the DAP2 *Pichia* homolog of *Saccharomyces cerevisiae* did not prevent N-terminal proteolytic cleavage, Melarkode et al., WO 2007/148345; Prabha et al., *Protein Expression and Purification*, 64, 155-161, 2009.

Ste13p and Dap2p individually have been shown to cleave N-terminal peptides having the motif X-P/A, where X is any amino acid and the second position is either praline (P) or alanine (A), Misumi and Ikehara, *Handbook of Proteolytic Enzymes*, 2nd edition, pp. 1910-1911, Elsevier, London, 2004. The TNFRII-Fc and GCSF proteins used herein to illustrate the present invention conform to the conserved X-Pro Ste13p and Dap2p motif, suggesting that for production of therapeutic proteins in *Pichia pastoris*, the DAP activity of Ste13p or Dap2p must be eliminated. In contrast, the insulinotropic peptide of Melarkode et al, WO 2007/148345, possesses a novel non-conserved N-terminus with a His-Gly motif that is only recognized by Step 13p.

As demonstrated herein by Applicants, elimination of *Pichia pastoris* Step activity resulted in only a partial reduction in DAP activity for the TNFRII-Fc protein, with somewhat greater than half of the TNFRII-Fc protein produced having the full length sequence. Applicants surprisingly found that for complete elimination of DAP activity, i.e. for 100% occurrence of full length TNFRII-Fc protein, the activity of both Step 13p and Dap2p must be eliminated from the *Pichia pastoris* cell line. Similarly, only when both DAP genes are eliminated from *Pichia pastoris* did the Applicants observe intact production of a recombinant GCSF protein. Thus, one skilled in the art would recognize and appreciate that the present invention differs from the prior art by requiring the elimination of both Step 13p and Dap2p activity in *Pichia pastoris* for production of full length proteins having the N-terminal X-P/A motif.

Based on homologies amongst known DAP genes, one skilled in the art may design PCR primers, examples of which are shown in Table 1, or use genes or gene fragments as probes to identify homologues in DNA libraries of the target organism. Applicants' analysis of the *Pichia pastoris* genome to identify homologues having DAP activity has resulted in the identification of a homologue for STE13 and DAP2, designated PpSTE13 and PpDAP2, (FIGS. 8A and 8B, SEQ ID NOS: 37 and 38, and FIGS. 9A and 9B, SEQ ID NOS: 39 and 40), respectively. Melarkode et al., WO 2007/148345, describes the DNA sequence for a *Pichia pastoris* STE13 homologue, while Prabha et al., *Protein Expression and Purification*, 64: 155-161, 2009, describes the protein sequences for *Pichia pastoris* Ste13p and Dap2p homologues. The Ste13p homologue generated herein by Applicants appears to be in agreement with that reported previously in Melarkode et al. While major portions of the Dap2p protein sequence generated herein by Applicants agrees with that reported by Prabha et al., the Dap2p homologue identified herein differs at the C-terminus. Applicants' homologue contains the following C-terminus sequence:

```
                                              (SEQ ID NO: 46)
GLENYDIHVFPDSDHSIRYHNGNVIVYDKLFHWIRRAFKAGK.
```

Whereas the Prabha et al. homologue has the following C-terminus sequence:

```
GLENYDIHVFPDTIPLD.         (SEQ ID NO: 47)
```

The N-terminal sequences up to and including the underlined portion of the C-terminal sequences above are conserved in both homologues.

Table 1 lists sequences for representative primers used for the generation of knockout vectors in *Pichia pastoris*. Regions underlined in the primer sequence represent restriction enzyme recognition sites that have been introduced to facilitate gene knockout fragment generation. The specific restriction enzyme recognition sites introduced are named in the adjacent primer description column. Table 2 lists primers used to confirm knockout of the *Pichia* STE13 and DAP2 from the genome following transformation with the knockout vectors generated using the primers in Table 1. Successful deletion is confirmed when the 5' and 3' primer sets give PCR products of the desired size and the knockout primer set gives no product.

TABLE 1

| Primer | Sequence (5' to 3') | Description |
| --- | --- | --- |
| SH85 | GGCTCGAGGATCTGTTTAGCTTGCCTCGTCC (SEQ ID NO: 7) | NAT$^R$ cass XhoI for |
| SH86 | GGCTCGAGGGAGCTCGTTTTCGACACTGGATGG (SEQ ID NO: 8) | NAT$^R$ cass XhoI rev |
| SH379 | CATGCCCCTGAGCTGCGCACGTCAAG (SEQ ID NO: 9) | pTEF (NAT$^R$) outwards |
| SH380 | CAGAAAGTAATATCATGCGTCAATCG (SEQ ID NO: 10) | TEF tt (NAT$^R$) outwards |
| SH491 | GGCGATTACCGTTGATGTTGAAGTGGCGAG (SEQ ID NO: 11) | LacZ 5'-3' screen out |
| SH558 | CATCCAGAGGCACTTCACCGCTTGCCAGCG (SEQ ID NO: 12) | LacZ 3'-5' screen out |
| SH774 | GGAATTCGGCCTTGGGGGCCTCCAGGACTTGCTG (SEQ ID NO: 13) | PpSTE13 5' EcoRI for |
| SH775 | GGAATTCCTCGAGCTGTTTGAATCTGGAACGTACTCG (SEQ ID NO: 14) | PpSTE13 5' EcoRI rev |
| SH776 | GAAGCTTCTCGAGCTACTGGGAACCACGAGACATCAC (SEQ ID NO: 15) | PpSTE13 3' HindIII for |

TABLE 1-continued

| Primer | Sequence (5' to 3') | Description |
|---|---|---|
| SH777 | GCAAGCTTGGCCCATTAGGCCCACCTACAATCATTACC (SEQ ID NO: 16) | PpSTE13 3' HindIII rev |
| SH778 | CAAGGCACATTAAAAGTCCGCCAAGG (SEQ ID NO: 17) | PpSTE13 pre 5' |
| SH779 | GTGGCCCTTGTATTGATAGAAGTATTCAG (SEQ ID NO: 18) | PpSTE13 post 3' |
| SH780 | CACGTCTATCGTTGAACCAAAACAGAC (SEQ ID NO: 19) | PpSTE13 KO for |
| SH781 | GTAACCAATGGTATCTCCAACGACAG (SEQ ID NO: 20) | PpSTE13 KO rev |
| SH782 | GGAATTCGGCCACCTGGGCCTGTTGCTGCTGGTACTG (SEQ ID NO: 21) | PpDAP2 5' EcoRI for |
| SH783 | CGAATTCCTCGAGCGTTGTAAGTGATTGTAGACTCG (SEQ ID NO: 22) | PpDAP2 5' EcoRI rev |
| SH784 | GAAGCTTCTCGAGGGCAGCAAAGCCTTACGTTG (SEQ ID NO: 23) | PpDAP2 3' HindIII for |
| SH785 | GCAAGCTTGGCCTAGGTGGCCGACCCATTTTTAGAGG (SEQ ID NO: 24) | PpDAP2 3' HindIII rev |
| SH786 | CACTTTCATCCTGAGGATCTTGGTCCTG (SEQ ID NO: 25) | PpDAP2 pre 5' |
| SH787 | CATATACCAAAGCAATTGATATCTGGTC (SEQ ID NO: 26) | PpDAP2 post 3' |
| SH788 | CGGATAAGAGACATAATTGGCGCCATTC (SEQ ID NO: 27) | PpDAP2 KO for |
| SH789 | CTTTCTATTGAGGATTTCTTGGTTGCTG (SEQ ID NO: 28) | PpDAP2 KO rev |
| SH801 | CGCCATCCAGTGTCGAAAACGCTGTTTGAATCTGGAACGTACTC (SEQ ID NO: 29) | STE13 5' (NAT$^R$) rev |
| SH802 | GAGTACGTTCCAGATTCAAACAGCGTTTTCGACACTGGATGGCG (SEQ ID NO: 30) | NAT$^R$ (STE13 5') for |
| SH803 | GTGATGTCTCGTGGTTCCCAGTAGTGTTTAGCTTGCCTCGTCCCCG (SEQ ID NO: 31) | NAT$^R$ (STE13 3') rev |
| SH804 | CGGGGACGAGGCAAGCTAAACACTACTGGGAACCACGAGACATCAC (SEQ ID NO: 32) | STE13 3' (NAT$^R$) for |
| SH805 | CGCCATCCAGTGTCGAAAACGCGTTGTAAGTGATTGTAGACTCGTTG (SEQ ID NO: 33) | DAP2 5' (NAT$^R$) rev |
| SH806 | CAACGAGTCTACAATCACTTACAACGCGTTTTCGACACTGGATGGCG (SEQ ID NO: 34) | NAT$^R$ (DAP2 5') for |
| SH807 | CAACGTAAGGCTTTGCTGCCTGTTTAGCTTGCCTCGTCCCCG (SEQ ID NO: 35) | NAT$^R$ (DAP2 3') rev |
| SH808 | CGGGGACGAGGCAAGCTAAACAGGCAGCAAAGCCTTACGTTG (SEQ ID NO: 36) | DAP2 3' (NAT$^R$) for |

TABLE 2

| Knock-out | Vector | Region | Primer pair | Product size (kb) |
|---|---|---|---|---|
| ste13::URA5 | pGLY4520 | 5' cross-over | SH778 (SEQ ID NO: 17) + SH558 (SEQ ID NO: 12) | 1.0 |
| | | 3' cross-over | SH779 (SEQ ID NO: 18) + SH491 (SEQ ID NO: 11) | 1.1 |
| | | Knock-out* | SH780 (SEQ ID NO: 19) + SH781 (SEQ ID NO: 20) | no product |
| dap2::URA5 | pGLY4521 | 5' cross-over | SH786 (SEQ ID NO: 25) + SH558 (SEQ ID NO: 12) | 1.2 |
| | | 3' cross-over | SH787 (SEQ ID NO: 26) + SH491 (SEQ ID NO: 11) | 1.4 |
| | | Knock-out* | SH788 (SEQ ID NO: 27) + SH789 (SEQ ID NO: 28) | no product |
| ste13::NAT$^R$ | pGLY5018 | 5' cross-over | SH778 (SEQ ID NO: 17) + SH380 (SEQ ID NO: 10) | 1.0 |
| | | 3' cross-over | SH779 (SEQ ID NO: 18) + SH379 (SEQ ID NO: 9) | 1.1 |
| | | Knock-out* | SH780 (SEQ ID NO: 19) + SH781 (SEQ ID NO: 20) | no product |
| dap2::NAT$^R$ | pGLY5019 | 5' cross-over | SH786 (SEQ ID NO: 25) + SH380 (SEQ ID NO: 10) | 1.2 |
| | | 3' cross-over | SH787 (SEQ ID NO: 26) + SH379 (SEQ ID NO: 9) | 1.4 |
| | | Knock-out* | SH788 (SEQ ID NO: 27) + SH789 (SEQ ID NO: 28) | no product |

*1 Kb product obtained with presence of wild-type loci

Figure 1B:
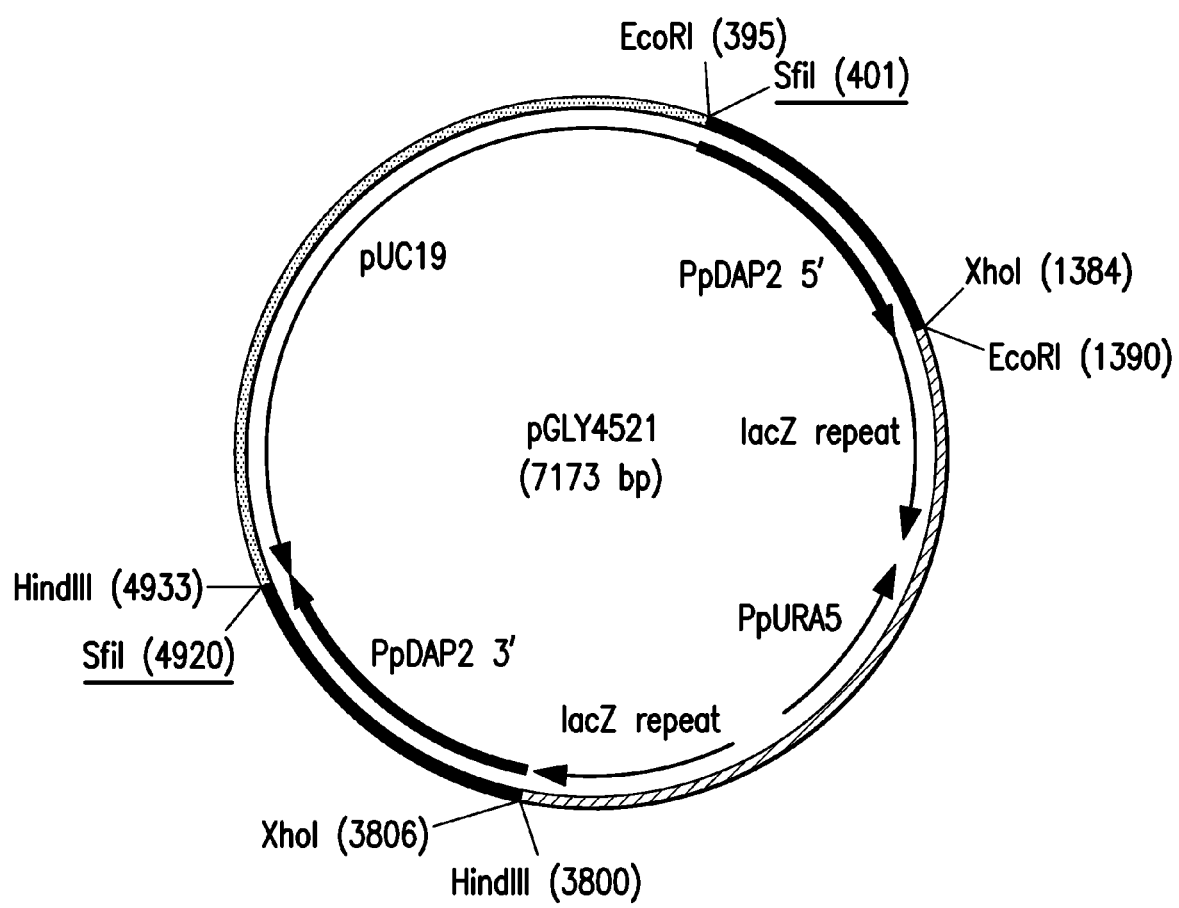
Figure 1C:
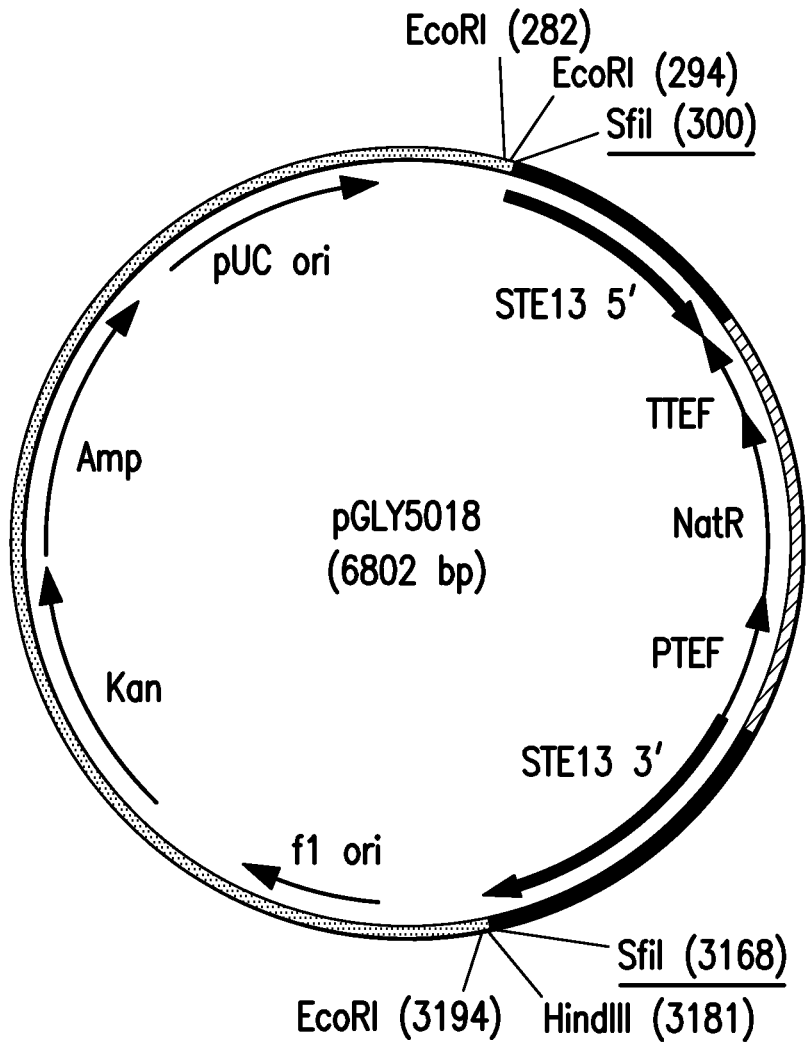
Figure 1D:
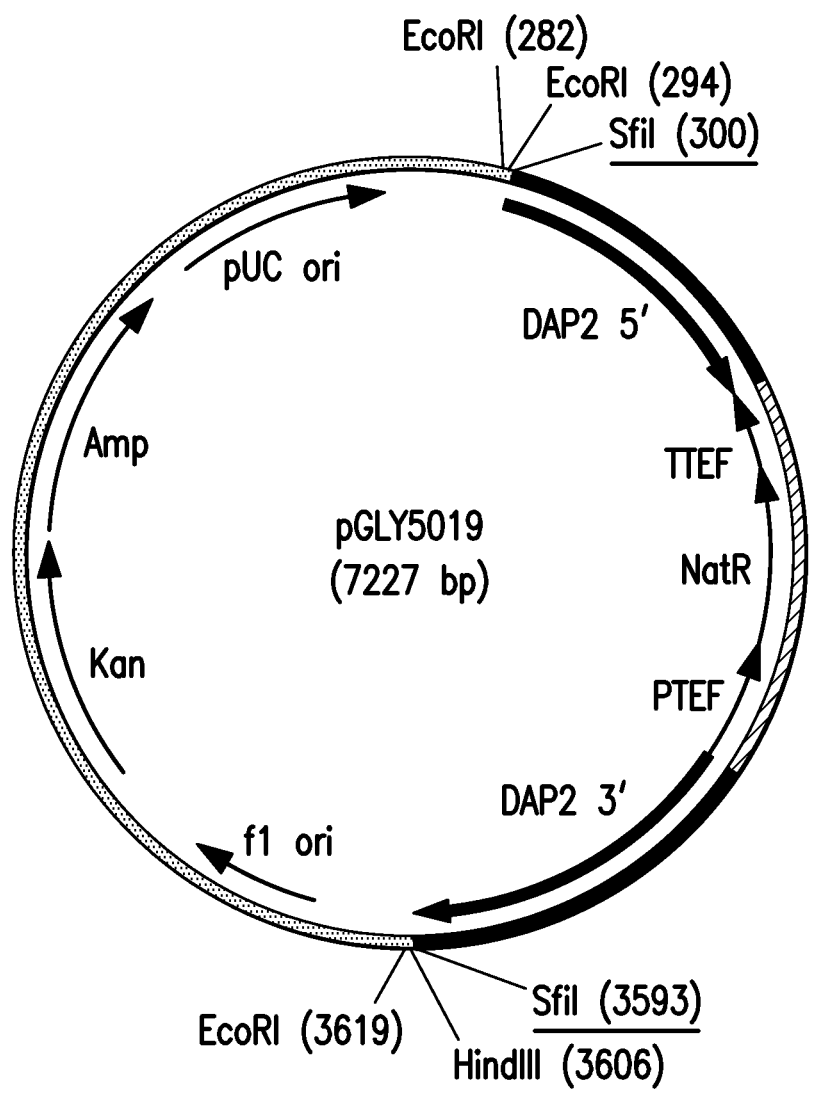

To assess the role of each of these genes with respect to the N-terminal truncation observed for TNFRII-Fc, knock-out vectors containing the URA5 gene were designed with the 5' and 3' regions of either the *Pichia pastoris* DAP2 or STE13 genes to target the vector for disruption of the DAP2 or STE13 locus of the genome (FIGS. 1A and 1B). These knockout vectors were transformed into the same ura minus parent strain (YGLY7406) expressing the recombinant fusion protein, TNFRII-Fc. Following PCR screening of the transformants, a Ppste13 and a Ppdap2 knockout strain were identified, YGLY8084 and YGLY8090, respectively. To generate a double knockout strain, i.e. knockout of both PpSTE13 and PpDAP2 in the same strain, the Ppste13 deletion strain, YGLY8084, was transformed with the PpDAP2 nourseothricin dominant marker knockout vector, pGLY5019 (FIG. 1D). Following PCR screening of the transformants, several Ppdap2 knockouts were obtained in the Ppste13::URA5 background parent strain. A representative Ppste13/Ppdap2 double knockout strain was designated YGLY8096.

Peptide analysis of the TNFRII-Fc secreted from each of these strains shows that while Ste13p plays a major role in the proteolysis of this polypeptide, deletion of both DAP genes is necessary to eliminate DAP activity. For the wild-type strain, 100% of the protein produced was truncated by two amino acids at the N-terminus. The single deletion of STE13 resulted in 59% of the peptide population having an intact N-terminus, while deletion of DAP2 resulted in the production of intact TNFRII-Fc, but to a much lesser degree, with only 15% of the secreted polypeptides having the full length sequence. Analysis of TNFRII-Fc secreted from the double knock-out strain, YGLY8096, indicated that 100% of the peptide population had an intact N-terminus. Table 3 is a summary of the data generated from this analysis showing the molar percentages of truncated versus full length peptides isolated. Data is representative of three replicate samples for each strain. Due to ura minus strains being poor secretors of recombinant protein, the prototrophic parent strain of YGLY7406, YGLY6646, was used to produce the material from a strain with both PpSTE13 and PpDAP2 genes un-interrupted. The genotype of this strain is described in Table 3 as wild-type, referring to both intact PpSTE13 and PpDAP2 loci.

TABLE 3

| Strain | Relevant Genotype | N-Terminal Sequence of Truncated/ Full Length Peptides Isolated | Truncated/ Full Length Peptide Occurence (Molar %) |
|---|---|---|---|
| YGLY6646 | Wild-type | AQVAF (SEQ ID NO: 2) and LPAQV (SEQ ID NO: 1) | 100/0 |
| YGLY8084 | ste13::URA5 | AQVAF (SEQ ID NO: 2) and LPAQV (SEQ ID NO: 1) | 41/59 |
| YGLY8090 | dap2::URA5 | AQVAF (SEQ ID NO: 2) and LPAQV (SEQ ID NO: 1) | 85/15 |
| YGLY8096 | ste13::URA5, dap2::NAT$^R$ | AQVAF (SEQ ID NO: 2) and LPAQV (SEQ ID NO: 1) | 0/100 |

Figure 6:
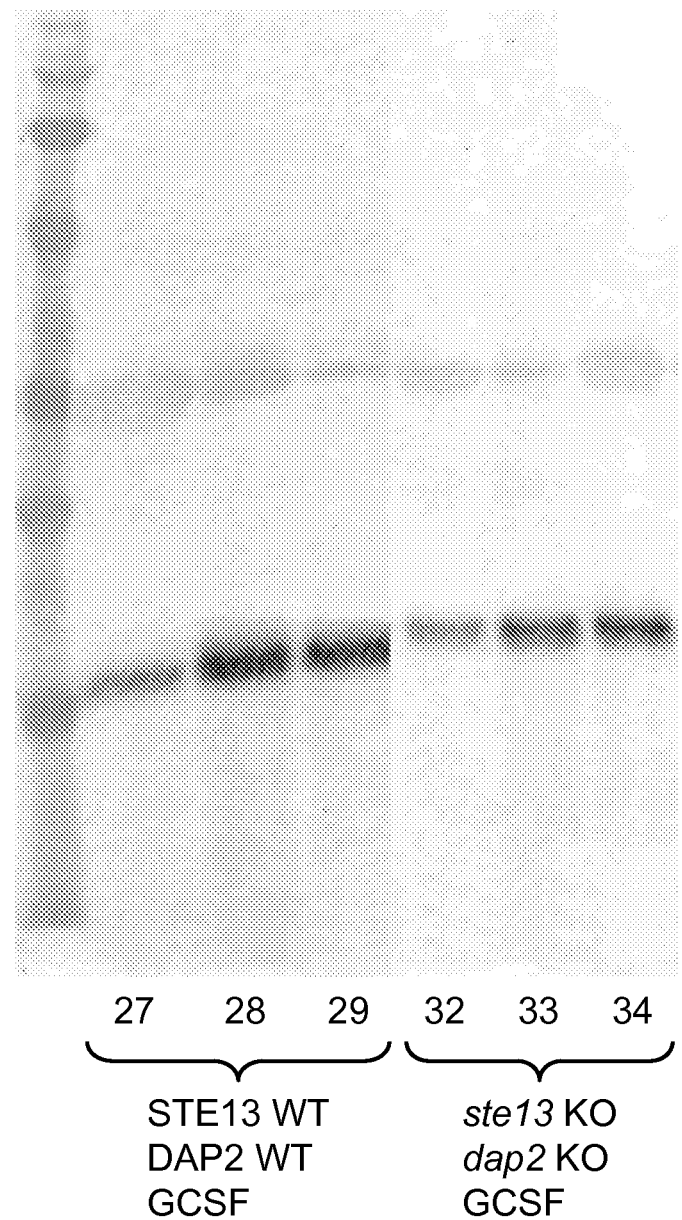
FIG. 6 is a representation of a western blot of GCSF produced in a *Pichia pastoris* strain where neither the STE13 nor the DAP2 genes have been deleted or disrupted, i.e. lower molecular weight GCSF due to DAP cleavage (lanes 27-29), as compared to intact higher molecular GCSF produced in a *Pichia pastoris* strain when Ste13p and Dap2p activity has been eliminated (lanes 32-34).

Based on this analysis Applicants determined that PpSte13p and PpDap2p are the sole proteases involved in the N-terminal proteolysis of recombinant TNFRII-Fc expressed in *Pichia pastoris* and that deletion of both are required to eliminate DAP activity. Similarly, when a wild-type granulocyte colony-stimulating factor (GCSF) polypeptide (protein sequence in FIG. 5; SEQ ID NO: 6) was expressed in *Pichia pastoris* the N-terminus was truncated. N-terminal sequencing of this material indicated that it lacked two amino acids at the N-terminus (FIGS. 4A and 4B, SEQ ID NOS: 4 and 5, respectively). Production of this truncated form of GCSF was also completely eliminated by producing the GCSF in a double APpstel3/Ppdap2 knockout background (FIG. 6). In both instances, cleavage of these recombinant proteins (TNFRII-Fc and CSF) occurs C-teiininal to a proline residue in the second position (relative to the N-terminal) of the polypeptide. As shown herein, deletion of both DAP associated genes in *Pichia pastoris* prevented truncation of a therapeutic protein having a praline in the second position from the N-terminus of the polypeptide and that deletion of both PpSTE13 and PpDAP2 was required for elimination of DAP activity.

Both therapeutic protein examples described above have the N-terminal motif Xaa-Pro, where X can be any amino acid. As described above, Ste13p and Dap2p individually have been shown to cleave N-terminal peptides also having the motif Xaa-Ala, where Xaa is any amino acid and alanine (Ala) is the second amino acid, Misumi and Ikehara, *Handbook of Proteolytic Enzymes,* 2nd edition, pp. 1910-1911, Elsevier, London, 2004. To demonstrate that knockouts of both PpSTE13 and PpDAP2 are required to prevent truncation of proteins with the Xaa-Ala motif, one skilled in the art can mutate the second amino acid in the secreted form of TNFR-Fc from a proline to an alanine. Based on the results herein it appears that deletion of either PpSTE13 or PpDAP2 would reduce the percentage of N-terminal cleavage observed. Complete elimination of DAP activity and the resulting 100% intact protein would only be observed from a double dPpste13/Ppdap2 knockout host strain, i.e. mutation to knockout both STE13 and DAP2.

Although the combined elimination of PpSte13p and PpDap2p has demonstrated the production of therapeutic proteins with intact N-termini, Applicants have found that *Pichia pastoris* has a third dipeptidyl aminopeptidase, herein referred to as PpDPPIII. This enzyme was identified by annotation of the *Pichia pastoris* genome and has 43% sequence identity to the human enzyme, dipeptidyl peptidase III (DppIIIp). The *Pichia pastoris* DppIIIp homologue has yet to be characterized, but is distinct from PpSte13p and PpDap2p at the sequence level, having only 10% and 12% sequence identity, respectively. While this DAP gene has not been fully characterized, Applicants believe that PpDppIIIp, when expressed under the proper conditions, will result in truncated proteins, notwithstanding that no activity was observed under the conditions evaluated herein. Those of skill in the art would recognize and appreciate that, under other growth conditions or through expression with other reporter proteins, PpDppIIIp activity may be evidenced. As such, under other appropriate conditions or reporters, to completely eliminate DAP activity in a *Pichia pastoris*, PpDppIII may need to be deleted or disrupted, either alone or in conjunction with PpSte13p and/or PpDap2p activity. Those skilled in the art would be able to delete or disrupt PpDPPIII according to the methods set forth in the examples herein, specifically those of Example 5.

*Pichia* Strains for Elimination of DAP Activity

While any commercially available *Pichia pastoris* strain can be utilized for the present invention, such as NRRL-Y11430 (American Type Culture Collection (ATCC), Manassas, Va., Catalog No. 76273), in a preferred embodiment the strain employed for the invention herein would be a glycoengineered *Pichia pastoris* strain, for example, the GS5.0 strain described in Example 3 or the glycoengineered strains described infra, which incorporates modifications to generate a human-like glycosylation profile upon expression. For example, in the case of the GS5.0 strain of Example 3, such modifications include those directed to the deletion of Δoch1, Δpno1, Δmnn4B, Δbmt2, and Δura5, or the insertion of *K. lactis* and *M. musculus* UDP-GlcNAc transporters, *M. musculus* α-1,2-MnsI, *H. sapiens* β-1,2,-GlcNAc transferase 1 activity, *R. norvegicus* β-1,2-GlcNAc transferase II activity, *D. melanogaster* MnsII activity, *S. pombe* Gal epimerase, *D. melanogaster* UDP-Gal transporter and *H sapiens* β-1,4-galactosyltransferase activity. A GS5.0 strain is capable of producing glycoproteins that have galactose-terminated N-glycans, e.g., $GalGlcNAc_2Man_3GlcNAc_2$, $Gal_2GlcNAc_2Man_3GlcNAc_2$, or mixtures thereof. Other representative glycoengineered strains include YJN201 (Choi et al., *PNAS*, 100 (9): 5022-5027, 2003); YSH44 (Hamilton et al., *Science*, 301 (5637): 1244-1246, 2003); RDP36-1 (Davidson et al., *Glycobiology*, 14 (4): 1-9, 2004); PBP6-5 (Bobrowicz et al., *Glycobiology*, 14 (9): 757-766, 2004); YSH597 (Hamilton et al., *Science*, 313 (5792): 1441-1443, 2006).

In addition to *Pichia pastoris*, host cells useful in the present invention include yeast that express homologues to the *Pichia pastoris* DAP2 and STE13 genes. Such yeast may be selected from among *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pfjperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*. Various yeasts, such as *K. lactis*, *Pichia pastoris*, *Pichia methanolica*, and *Hansenula polymorpha* are particularly suitable for cell culture because they are able to grow to high cell densities and secrete large quantities of recombinant protein.

Yeast can be genetically modified so that they express glycoproteins in which the glycosylation pattern is human-like or humanized. In this manner, glycoprotein compositions can be produced in which a specific desired glycoform is predominant in the composition. Such can be achieved by eliminating selected endogenous glycosylation enzymes and/or genetically engineering the host cells and/or supplying exogenous enzymes to mimic all or part of the mammalian glycosylation pathway as described in US 2004/0018590. If desired, additional genetic engineering of the glycosylation can be performed, such that the glycoprotein can be produced with or without core fucosylation. Use of lower eukaryotic host cells is further advantageous in that these cells are able to produce highly homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition.

Yeast, can be genetically modified so that they express glycoproteins in which the glycosylation pattern is human-like or humanized. Human-like or humanized N-glycans include both hybrid and complex N-glycans. Such can be achieved by eliminating selected endogenous glycosylation enzymes and/or supplying exogenous enzymes as described by Gerngross et al., US 20040018590. For example, a host cell can be selected or engineered to be depleted in 1,6-mannosyl transferase activities, which would otherwise add mannose residues onto the N-glycan on a glycoprotein.

In one embodiment, the host cell further includes an α-1,2-mannosidase catalytic domain fused to a cellular targeting signal peptide not normally associated with the catalytic domain and selected to target the α-1,2-marmosidase activity to the ER or Golgi apparatus of the host cell. Passage of a recombinant glycoprotein through the ER or Golgi apparatus of the host cell produces a recombinant glycoprotein comprising a $Man_5GlcNAc_2$ glycoform, for example, a recombinant glycoprotein composition comprising predominantly a $Man_5GlcNAc_2$ glycoform. For example, U.S. Pat. No. 7,029,872 and U.S. Published Patent Application Nos. 2004/0018590 and 2005/0170452 disclose lower eukaryote host cells capable of producing a glycoprotein comprising a $Man_5GlcNAc_2$ glycoform.

In a further embodiment, the immediately preceding host cell further includes a GlcNAc transferase I (GnT I) catalytic domain fused to a cellular targeting signal peptide not normally associated with the catalytic domain and selected to target GlcNAc transferase 1 activity to the ER or Golgi apparatus of the host cell. Passage of the recombinant glycoprotein through the ER or Golgi apparatus of the host cell produces a recombinant glycoprotein comprising a $GlcNAcMan_5GlcNAc_2$ glycoform, for example a recombinant glycoprotein composition comprising predominantly a hybrid GlcNAcMan$_5$GlcNAc$_2$ glycoform. U.S. Pat. No. 7,029,872 and U.S. Published Patent Application Nos. 2004/0018590 and 2005/0170452 disclose lower eukaryote host cells capable of producing a glycoprotein comprising a GlcNAcMan$_5$GlcNAc$_2$ glycoform. The glycoprotein produced in the above cells can be treated in vitro with a hexosaminidase to produce a recombinant glycoprotein comprising a Man$_5$GlcNAc$_2$ glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant glycoprotein through the ER or Golgi apparatus of the host cell produces a recombinant glycoprotein comprising a GlcNAcMan$_3$GlcNAc$_2$ glycoform, for example a recombinant glycoprotein composition comprising predominantly a complex GloNAcMan$_3$GlcNAc$_2$ glycoform. U.S. Pat. No. 7,029,872 and U.S. Published Patent Application No. 2004/0230042 discloses lower eukaryote host cells that express mannosidase II enzymes and are capable of producing glycoproteins having predominantly a GlcNAc$_2$Man$_3$GlcNAc$_2$ glycoform. The glycoprotein produced in the above cells can be treated in vitro with a hexosaminidase to produce a recombinant glycoprotein comprising a Man$_3$GlcNAc$_2$ glycoform.

In a further embodiment, the immediately preceding host cell further includes GlcNAc transferase II (GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a GlcNAc$_2$Man$_3$GlcNAc$_2$ glycoform, for example a recombinant glycoprotein composition comprising predominantly a complex GlcNAc$_2$Man$_3$GlcNAc$_2$ glycoform. U.S. Pat. No. 7,029,872 and U.S. Published Patent Application Nos. 2004/0018590 and 2005/0170452 disclose lower eukaryote host cells capable of producing a glycoprotein comprising a GICNAc$_2$Man$_3$GlcNAc$_2$ glycoform. The glycoprotein produced in the above cells can be treated in vitro with a hexosaminidase to produce a recombinant glycoprotein comprising a Man$_3$GlcNAc$_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a complex GalGlcNAc$_2$Man$_3$GlcNAc$_2$ (G1) or complex Gal$_2$GlcNAc$_2$Man$_3$GlcNAc$_2$ (G2) glycoform, or mixture thereof for example a recombinant glycoprotein composition comprising predominantly a GalGlcNAc$_2$Man$_3$GlcNAc$_2$ glycoform or Gal$_2$GlcNAc$_2$Man$_3$GlcNAc$_2$ glycofoini or mixture thereof. U.S. Pat. No. 7,029,872 and U.S. Published Patent Application No. 2006/0040353 discloses lower eukaryote host cells capable of producing a glycoprotein comprising a Gal$_2$GlcNAc$_2$Man$_3$GlcNAc$_2$ glycoform. The glycoprotein produced in the above cells can be treated in vitro with a galactosidase to produce a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform.

In a further embodiment, the immediately preceding host cell further includes a sialyltransferase catalytic domain fused to a cellular targeting signal peptide not normally associated with the catalytic domain and selected to target sialytransferase activity to the ER or Golgi apparatus of the host cell. Passage of the recombinant glycoprotein through the ER or Golgi apparatus of the host cell produces a recombinant glycoprotein comprising predominantly a complex NANA$_2$Gal$_2$GlcNAc$_2$Man$_3$GlcNAc$_2$ glycoform or complex NANAGal$_2$GlcNAc$_2$Man$_3$GlcNAc$_2$ glycoform or mixture thereof. It is useful that the host cell further include a means for providing CMP-sialic acid for transfer to the N-glycan, U.S. Published Patent Application No. 2005/0260729 discloses a method for genetically engineering lower eukaryotes to have a CMP-sialic acid synthesis pathway and U.S. Published Patent Application No. 2006/0286637 discloses a method for genetically engineering lower eukaryotes to produce sialylated glycoproteins. The glycoprotein produced in the above cells can be treated in vitro with a neuraminidase to produce a recombinant glycoprotein comprising predominantly a Gal$_2$GlcNAc$_2$Man$_3$GlcNAc$_2$ glycoform.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX) N-glycan structures such as disclosed in U.S. Published Patent Application Nos. 2004/074458 and 2007/0037248.

In further embodiments, the host cell that produces glycoproteins that have predominantly hybrid GlcNAcMan$_5$GlcNAc$_2$ N-glycans further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising predominantly the hybrid GalGlcNAcMan$_5$GlcNAc$_2$ glycoform.

In a further embodiment, the immediately preceding host cell that produced glycoproteins that have predominantly the GalGlcNAcMan$_5$GlcNAc$_2$ N-glycans further includes a sialyltransferase catalytic domain fused to a cellular targeting signal peptide not normally associated with the catalytic domain and selected to target sialytransferase activity to the ER or Golgi apparatus of the host cell. Passage of the recombinant glycoprotein through the ER or Golgi apparatus of the host cell produces a recombinant glycoprotein comprising a hybrid NANAGalGlcNAcMan$_5$GlcNAc$_2$ glycoform.

Various of the preceding host cells further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Host cells further include lower eukaryote cells (e.g., yeast such as *Pichia pastoris*) that are genetically engineered to eliminate glycoproteins having α-mannosidase-resistant N-glycans by deleting or disrupting one or more of the β-mannosyltransferase genes (e.g., BMT1, BMT2, BMT3, and BMT4)(See, U.S. Published Patent Application No. 2006/0211085) and glycoproteins having phosphomannose residues by deleting or disrupting one or both of the phosphomannosyl transferase genes PNO1 and MNN4B (See for example, U.S. Pat. Nos. 7,198,921 and 7,259,007), which in further aspects can also include deleting or disrupting the MNN4A gene. Disruption includes disrupting the open reading frame encoding the particular enzymes or disrupting expression of the open reading frame or abrogating translation of RNAs encoding one or more of the β-marmosyltransferases and/or phosphomanno-syltransferases using interfering RNA, antisense RNA, or the like. The host cells can further include any one of the aforementioned host cells modified to produce particular N-glycan structures.

Host cells further include lower eukaryote cells (e.g., yeast such as *Pichia pastoris*) that are genetically modified to control O-glycosylation of the glycoprotein by deleting or disrupting one or more of the protein O-mannosyltransferase (Dol-P-Man:Protein (Ser/Thr) Mannosyl Transferase genes) (PMTs) (See U.S. Pat. No. 5,714,377) or grown in the presence of Pmtp inhibitors and/or an alpha-mannosidase as disclosed in Published International Application No, WO 2007061631, or both. Disruption includes disrupting the open reading frame encoding the Pmtp or disrupting expression of the open reading frame or abrogating translation of RNAs encoding one or more of the Pmtps using interfering RNA, antisense RNA, or the like. The host cells can further include any one of the aforementioned host cells modified to produce particular N-glycan structures.

Pmtp inhibitors include but are not limited to a benzylidene thiazolidinediones. Examples of benzylidene thiazolidinediones that can be used are 5-[[3,4-bis(phenylmethoxy)phenyl]methylene]-4-oxo-2-thioxo-3-thiazolidineacetic acid; 5-[[3-(1-phenylethoxy)-4-(2-phenylethoxy)]phenyl]methylene]-4-oxo-2-thioxo-3-thiazolidineacetic acid; and 5-[[3-(1-phenyl-2-hydroxy)ethoxy)-4-(2-phenylethoxy)]phenyl]methylene]-4-oxo-2-thioxo-3-thiazolidineacetic acid.

In particular embodiments, the function or expression of at least one endogenous PMT gene is reduced, disrupted, or deleted. For example, in particular embodiments the function or expression of at least one endogenous PMT gene selected from the group consisting of the PMT1, PMT2, PMT3, and PMT4 genes is reduced, disrupted, or deleted; or the host cells are cultivated in the presence of one or more PMT inhibitors. In further embodiments, the host cells include one or more PMT gene deletions or disruptions and the host cells are cultivated in the presence of one or more Pmtp inhibitors. In particular aspects of these embodiments, the host cells also express a secreted alpha-1,2-mannosidase.

PMT deletions or disruptions and/or Pmtp inhibitors control O-glycosylation by reducing O-glycosylation occupancy, that is, by reducing the total number of O-glycosylation sites on the glycoprotein that are glycosylated. The further addition of an alpha-1,2-mannosidase that is secreted by the cell controls O-glycosylation by reducing the mannose chain length of the O-glycans that are on the glycoprotein. Thus, combining PMT deletions or disruptions and/or Pmtp inhibitors with expression of a secreted alpha-1,2-mannosidase controls O-glycosylation by reducing occupancy and chain length. In particular circumstances, the particular combination of PMT deletions or disruptions, Pmtp inhibitors, and alpha-1,2-mannosidase is determined empirically as particular heterologous glycoproteins (antibodies, for example) may be expressed and transported through the Golgi apparatus with different degrees of efficiency and thus may require a particular combination of PMT deletions or disruptions, Pmtp inhibitors, and alpha-1,2-mannosidase. In another aspect, genes encoding one or more endogenous mannosyltransferase enzymes are deleted. This deletion(s) can be in combination with providing the secreted alpha-1,2-mannosidase and/or PMT inhibitors or can be in lieu of providing the secreted alpha-1,2-mannosidase and/or PMT inhibitors.

Therefore, the host cell can be any host cell that has been genetically modified to produce glycoproteins wherein the predominant N-glycan is selected from the group consisting of complex N-glyeans, hybrid N-glycans, and high mannose N-glycans wherein complex N-glycans are selected from the group consisting of $Man_3GlcNAc_2$, $GlcNAc_{(1-4)}Man_3GlcNAc_2$, $Gal_{(1-4)}GlcNAc_{(1-4)}Man_3GlcNAc_2$, and $NANA_{(1-4)}Gal_{(1-4)}Man_3GlcNAc_2$; hybrid N-glycans are selected from the group consisting of $Man_5GlcNAc_2$, $GlcNAcMan_5GlcNAc_2$, $GalGlcNAcMan_5GlcNAc_2$, and $NANAGalGlcNAcMan_5GlcNAc_2$; and high mannose N-glycans are selected from the group consisting of $Man_6GlcNAc_2$, $Man_7GlcNAc_2$, $Man_8GlcNAc_2$, and $Man_9GlcNAc_2$. Examples of N-glycan structures include but are not limited to $Man_5GlcNAc_2$, $GlcNAcMan_5GlcNAc_2$, $GlcNAcMan_3GlcNAc_2$, $GlcNAc_2Man_3GlcNAc_2$, $GlcNAc_3Man_3GlcNAc_2$, $GlcNAc_4Man_3GlcNAc_2$, $GalGlcNAc_2Man_3GleNAc_2$, $Gal_2GlcNAc_2Man_3GlcNAc_2$, $Gal_2GlcNAc_3Man_3GlcNAc_2$, $Gal_2GlcNAc_4Man_3GlcNAc_2$, $Gal_3GlcNAc_3Man_3GlcNAc_2$, $Gal_3GlcNAc_4Man_3GlcNAc_2$, $Gal_4GlcNAc_4Man_3GlcNAc_2$, $NANAGal_2GlcNAc_2Man_3GlcNAc_2$, $NANA_2Gal_2GlcNAc_2Man_3GlcNAc_2$, $NANA_3Gal_3GlcNAc_3Man_3GlcNAc_2$, and $NANA_4Gal_4GlcNAc_4Man_3GlcNAc_2$.

In the examples that follow, the glycoengineered *Pichia pastoris* strain has been modified to eliminate Ste13p and Dap2p dipeptidyl aminopeptidase activity. In general, Ste13p and/or Dap2p activity can be eliminated from any *Pichia pastoris* strain using the methods described herein provided that the markers used for selection can be utilized with the strain. Alternatively another auxotropic or dominant marker, through which selection is available, may be substituted. For example, STE13 can be deleted from the commercially available strain, NRRL-Y11430, using the vector pGLY5018 (Example 2C) and nourseothricin as a selection marker. In that the markers for neither of the DAP2 knockout vectors described below (Example 2B) are compatible with NRRL-Y11430, a hygromycin marked vector can be generated from pAG32 (Goldstein, et al., *Yeast*, 15(6): 507-511, 1999; Erratum: *Yeast*, 15(12): 1297, 1999), using primers corresponding to the italicized fragments of primers SH806 and SH807 (Table 1) (SEQ ID NO: 48 and SEQ ID NO: 49, respectively) to amplify the 1654 bp Hyg marker from pAG32. This latter fragment can then be fused to the DAP2 5' and DAP2 3' flanking regions as described in Example 2C for the generation of pGLY5019. Following digestion with SfiI (New England BioLabs, Ipswich, Mass.), the vector can be transformed into either NRRL-Y11430 or the stela knockout derivative thereof and selected on hygromycin containing plates to produce either the single dap2Δ or double Δste13/dap2 knockout strains, respectively. An example is also provided as to how one skilled in the art would be able to use a glycoengineered *Pichic pastoris* strain that has been modified to eliminate DppIIIp dipeptidyl aminopeptidase activity using the methods described herein.

Example 1

Strains, Culture Conditions, and Reagents

*Escherichia coli* strains TOP10 (Invitrogen, Carlsbad, Calif.) or XL10-Gold (Stratagene, Santa Clara, Calif.) were used for recombinant DNA work. Restriction and modification enzymes were obtained from New England BioLabs, Ipswich, Mass., and used as directed by the manufacturer. Oligonucleotides were obtained from Integrated DNA Technologies, Coralville, Iowa. Salts and buffering agents were from Sigma, St. Louis, Mo. Minimal medium used herein comprised 1.4% yeast nitrogen base, 2% dextrose, 1.5% agar and $4 \times 10^{-5}$% biotin and amino acids supplemented as appropriate. YMD rich media is 1% yeast extract, 2% martone, 2% dextrose, and 1.5% agar for plates. Nourseothricin is obtained from US Biologicals, Swampscott, Mass. (Catalogue number N5375-74) and is added to the YMD rich media to a final concentration of 100 µg/ml.

Example 2

Generation of Knock-Out Vectors

A. Generation of step13::URA5 Knock-Out Vector

DNA fragments corresponding to 5' and 3' flanking regions of the STE13 open reading frame (SEQ ID NO: 41 and 42) were amplified using PfuUltra™ DNA polymerase (Stratagene, Santa Clara, Calif.) and genomic DNA from the *Pichia pastoris* strain NRRL-Y11430 as template. The primer pairs SH774 (SEQ ID NO: 13) and SH775 (SEQ ID NO: 14) and SH776 (SEQ ID NO: 15) and SH1777 (SEQ ID NO: 16), shown in Table 1, were used to amplify the 771 bp and 949 bp fragments for STE13 5' and 3', respectively. Following incubation with ExTaq™ (TaKaRa, Bio. Inc., Japan) for ten minutes at 72° C., the amplified fragments were cloned into pCR2.1 (Invitrogen, Carlsbad, Calif.) and transformed into TOP10 competent cells. DNA sequencing confirmed the STE13 5' and STE13 3' flanking regions were correct and the resultant vectors were designated pGLY4511 and pGLY4512, respectively.

A 763 bp STE13 5' flanking region fragment (represented by the underlined region of FIG. 10A, SEQ ID NO: 50) was digested from pGLY4511 using EcoRI and subcloned into a *P. pastoris* URA5-blaster vector pGLY13b, similar to pJN396 (Nett and Gerngross, Yeast, 20, 1279-1290, 2003), which was previously digested with the same restriction enzyme and treated with calf intestinal alkaline phosphatase (CTAP). The URA5-blaster vector possesses a pUC19 vector backbone containing a functional gene fragment of the *Pichia* URA5 gene flanked by LacZ direct repeats to facilitate recovery of the URA5 marker through counter selection on 5-fluoroorotic acid. Following transformation of the newly ligated vector into XL10 Gold competent cells and confirmation by restriction analysis, the resultant vector was designated pGLY4518. The vector pGLY4512 was digested with HindIII to release a 940 bp (represented by the underlined region of FIG. 10B, SEQ ID NO: 51) fragment encoding the STE13 3' flanking region and subcloned into pGLY4518, which was previously digested with the same enzyme and CIAP treated. The ligation product was transformed into XL10 Gold competent cells and designated pGLY4520 following restriction analysis. This final step13:: Ura5 knockout vector is shown graphically in FIG. 1A.

B. Generation of dap2:: URA5 Knock-Out Vector

The DAP2 5' and 3' flanking regions (SEQ ID NO: 43 and 44) were amplified from *Pichia pastoris* genomic DNA as described above using the primer sets SH782 (SEQ ID NO: 21) and SH783 (SEQ ID NO: 22) and SH784 (SEQ ID NO: 23) and SH785 (SEQ ID NO: 24), shown in Table 1, to generate 1003 bp and 1142 bp fragments, respectively. Following cloning into pCR2.1 and sequencing, the vectors were designated pGLY4513 and pGLY4514, encoding the DAP2 5' and DAP2 3' regions, respectively. Following a similar approach to that described above in Example 2A, the 995 bp DAP2 5' region (represented by the underlined region of FIG. 11A, SEQ ID NO: 52) was subcloned into the EcoRI site in the Ura5-blaster vector pGLY13b, resulting in the intermediate construct pGLY4519. Subsequently the 1133 bp DAP2 3' region (represented by the underlined region of FIG. 11B, SEQ ID NO: 53) was subcloned into the HindIII site of pGLY4519, resulting in the dap2::URA5 knockout vector pGLY4521, shown graphically in FIG. 1B.

C. Generation of Dominant Marker STE13 and DAP2 Knockout Vectors

PCR fusion was used to generate both STE13 and DAP2 knockout vectors. The STE13 5' and STE13 3' fragments were amplified from pGLY4520 with the primer pairs SH774 (SEQ ID NO: 13) and SH801 (SEQ ID NO: 29) and SH804 (SEQ ID NO: 32) and SH777 (SEQ ID NO: 16), shown in Table 1, using PfuUltra™ DNA polymerase. The nourseothricin ($NAZ^R$) marker cassette (SEQ ID NO: 45), which contains the open reading frame for the nourseothricin acetyltransferase (represented by the bold text of FIG. 12, SEQ ID NO: 54) from *Streptomyces noursei* under the expressional control of the *Ashbya gossypii* Transcription Elongation Factor (TEF) promoter and terminator (represented by the regular text of FIG. 12), which are 5' and 3' to the highlighted open reading frame, respectively), was amplified from pAG25 (Goldstein and McCusker, Yeast, 15, 1541-1553, 1999) using the primers SH802 (SEQ ID NO: 30) and SH803 (SEQ ID NO: 31). The PCR reactions were run on a DNA agarose gel and the 779 bp, 958 bp, and 1249 bp fragments, corresponding to STE13 5', STE13 3' and the Nat marker, respectively, were isolated. Subsequently 20 ng of each were combined and fused together using PfuUltra™ DNA polymerase and the primer pair SH774 (SEQ ID NO: 13) and SH777 (SEQ ID NO: 16). Following incubation for ten minutes at 72° C. with ExTaq™ DNA polymerase (TaKaRa, Bio. Inc., Japan), the amplified (2896 bp) fragment was cloned into pCR2.1 and transformed into TOP10 competent cells. DNA sequencing confirmed that the step13:: $NAT^R$ fusion was correct and the resultant vector was designated pGLY5018. This vector is shown graphically in FIG. 1C.

In a similar manner, the primer sets SH782 (SEQ ID NO: 21) and SH805 (SEQ ID NO: 33), SH808 (SEQ ID NO: 36) and SH785 (SEQ ID NO: 24), and SH806 (SEQ ID NO: 34) and SH807 (SEQ ID NO: 35), shown in Table 1, were used to amplify 1011 bp, 1151 bp, and 1248 bp fragments corresponding to DAP2 5', DAP2 3', and the $NAT^R$ marker from pGLY4521 and pAG25. Following isolation 20 ng of each fragment was used with the primer pair SH782 (SEQ ID NO: 21) and SH785 (SEQ ID NO: 24) to generate the 3321 bp fragment that was cloned into pCR2.1, sequenced and designated pGLY5019. This vector is shown graphically in FIG. 1D.

Example 3

Generation of STEI3 and DAP2 Knockout Strains

*Pichia pastoris* auxotrophic glycoengineered cell line YGLY7406 [Δoch1, Δmnn4B, Δbmt2, Δura5, *K. lactis* and

Figure 7A:
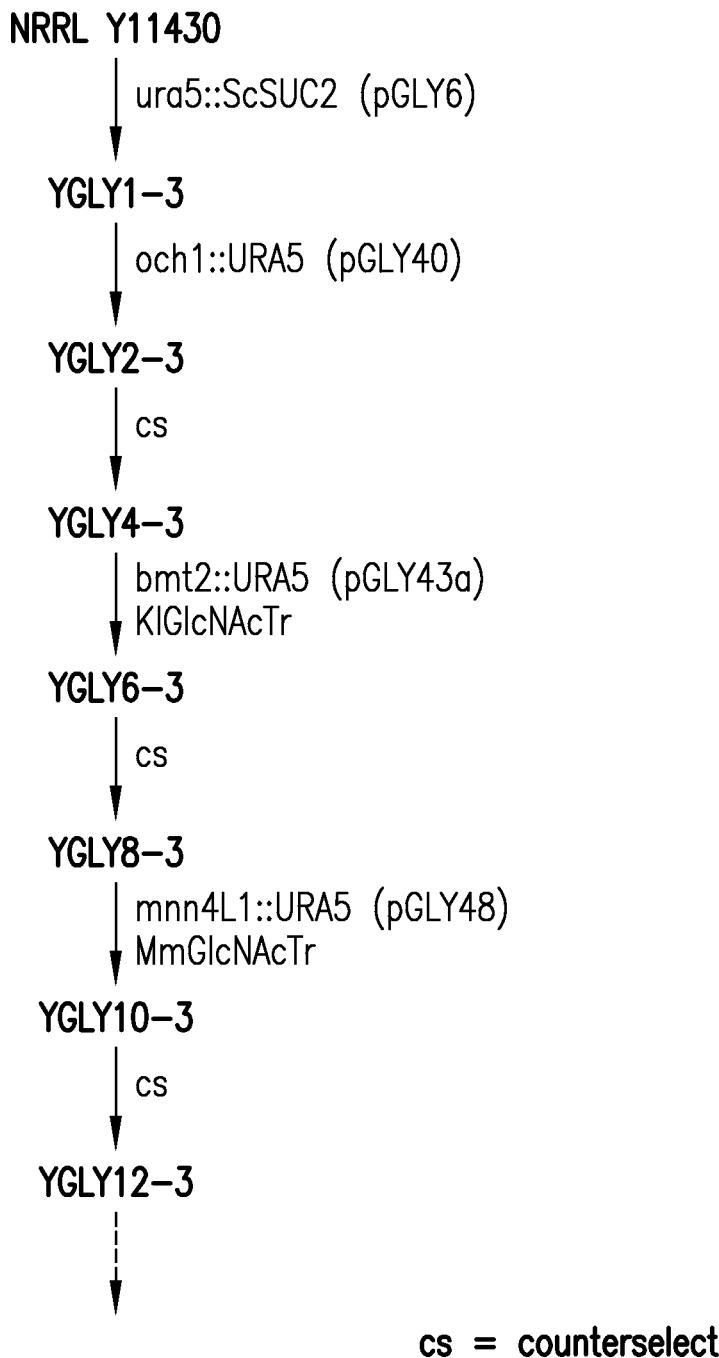
FIGS. 7A-7C represents a flow diagram for the glycoengineered strain, YGLY7406, used for generation of the knockout of STE13 and DAP2 (Example 3).
Figure 7B:
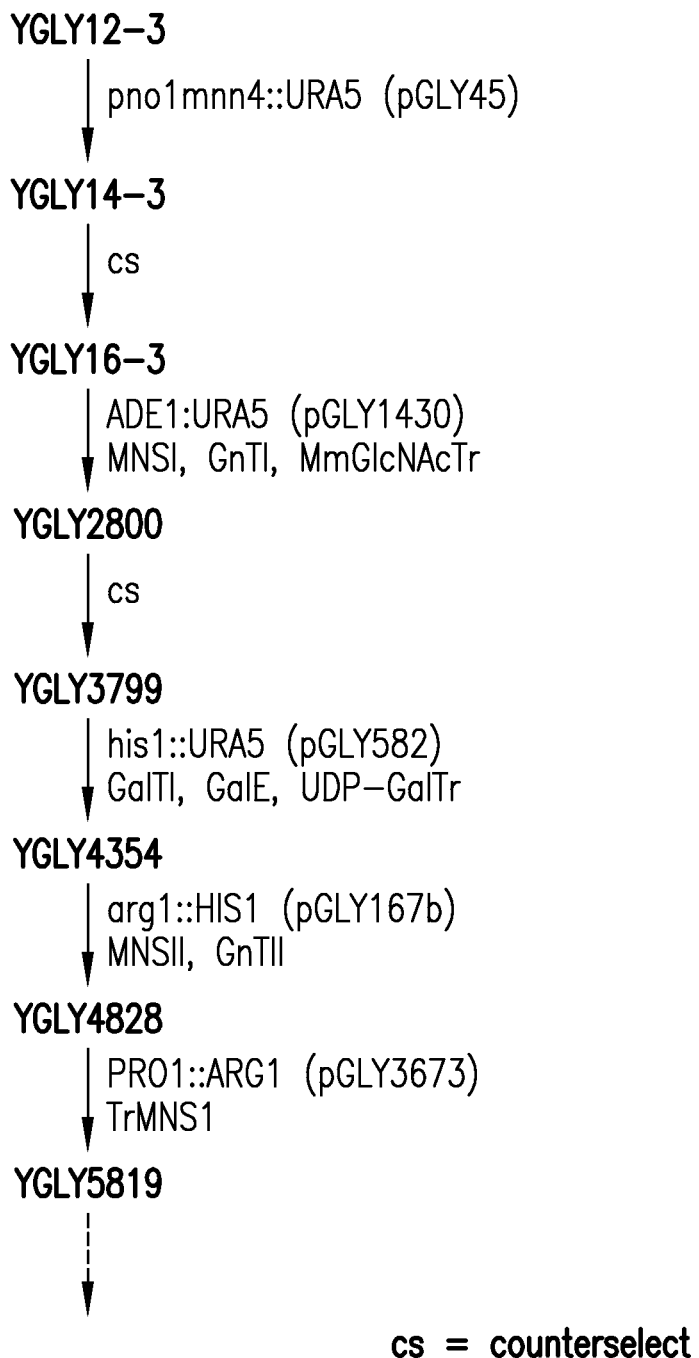
Figure 7C:
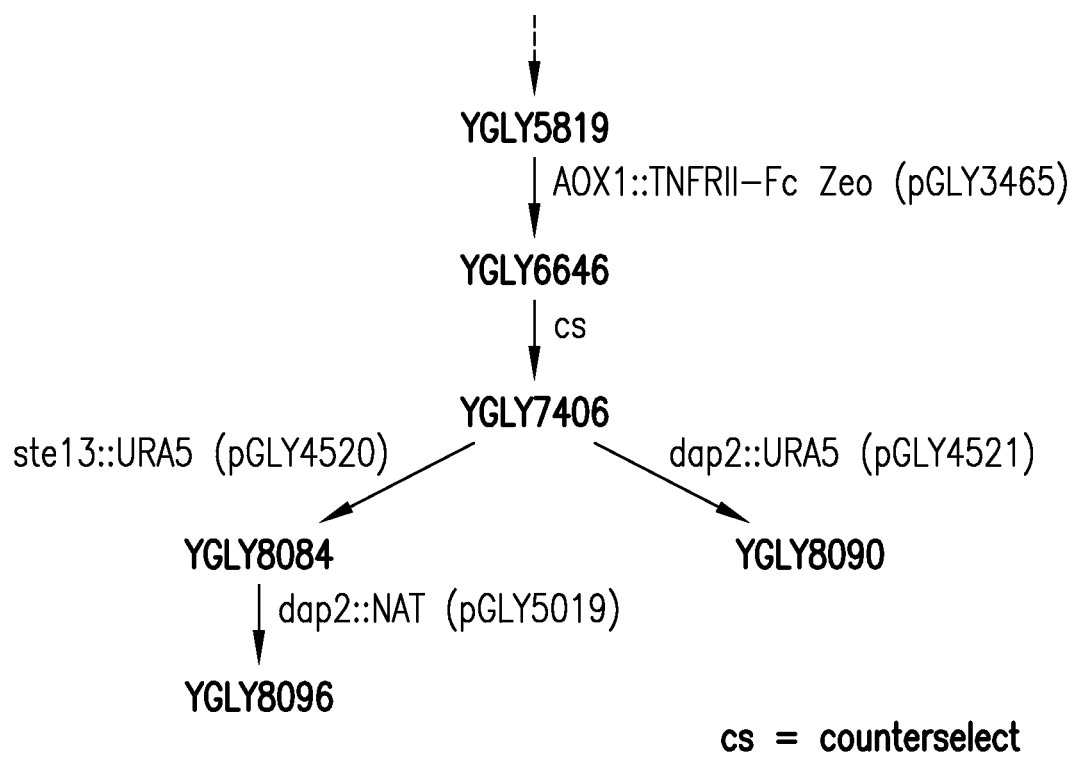

*M. musculus* UDP-GlcNAc transporters, *M. musculus* α-1, 2-MnsI, *H. sapiens* β-1,2-GlcNAc transferase 1, *R. norvegieus* β-1,2-GlcNAc transferase II, *D. melanogaster* MnsII, *S. pombe* Gal epimerase, *D. melanogaster* UDP-Gal transporter and *H sapiens* β-1,4-galactosyltransferase] expressing GS5.0 glycans (See for example, Bobrowicz et al., *Glycobiology*, 14(9): 757-766, 2004; Hamilton et al., *Science*, 313 (5792): 14411-1443, 2006); U.S. Published Application No. 20060040353, was used as the starting strain for all manipulations. See FIG. 7 (A-C) for a flow diagram of how this and the subsequent strains were generated. GS5.0 strains can produce glycoproteins having bi-antennary afucosylated N-linked glycans terminating in β-1,4 galactose residues on the non-reducing ends of one or both termini (Bobrowicz et al., *Glycobiology*, 14(9): 757-766, 2004; Hamilton et al., *Science*, 313 (5792): 14411-1443, 2006). The strain YGLY7406 expresses full length human tumor-necrosis factor receptor II fused to the Fc domain of IgG1 (TNFRII-Fc), which will be used as a reporter protein for dipeptidyl peptidase activity.

For transformation 20 μg of the vectors pGLY4520 and pGLY4521 were digested with the restriction enzyme SfiI (New England Biolabs, Ipswich, Mass.) to release a 4091 bp STE13::Ura5 knock-out fragment or a 4516 bp DAP2:: URA5 knock-out fragment which were transformed into YGLY7406 by electroporation to delete STE13 or DAP2, respectively, and selected on ura minus minimal plates. Successful knockouts of each gene were confirmed using the 5', 3' and knock-out primer sets shown in Table 2. The ste13Δ and dap2Δ knockout strains were named YGLY8084 and YGLY8090, respectively. Subsequently, the double Δste13/dap2 knockout strain was generated by transforming the ste13Δ knockout strain, YGLY8084, with pGLY5019, which was previously digested with SfiI to release the 3290 bp DAP2::Nat knock-out fragment. Transformants were plated on 100 μg/ml Nat YMD plates and successful double knockouts were confirmed using the 5', 3' and knockout primer sets shown in Table 2. A representative double knockout strain was designated YGLY8096. Although this strain was generated by knocking-out the STE13 first followed by knocking-out the DAP2, we have experimentally demonstrated that a strain with the same desired phenotype can be obtained if the DAP2 gene is knocked-out first followed knock-out of the STE13 gene. To obtain such a strain, pGLY5018 is digested with SfiI and the 2865 bp step13:: NAT$^R$ knock-out fragment generated can be transformed into a strain such as YGLY8090, where the DAP2 gene has already been knocked-out.

Example 4

Generation, Isolation and Analysis of Reporter Protein

Protein expression was carried out for 72 hours at 26° C. in 200 ml buffered glycerol-complex medium (BMGY) consisting of 1% yeast extract, 2% peptone, 100 mM potassium phosphate buffer, pH 6.0, 1.34% yeast nitrogen base, 0.00004% biotin, and 1% glycerol as a growth medium. Induction was performed for 48 hours in 20 ml of buffered methanol-complex medium (BMMY), consisting of 1.5% methanol instead of glycerol in BMGY.

Following expression, the cells were removed by centrifugation at 2000 rpm for fifteen minutes. The TNFRII-Fc fusion protein was captured by affinity chromatography from the supernatant using Streamliner Protein A resin from GE Healthcare (Chalfont St. Giles, UK, Cat. #17-1281-01).

The cell free supernatant medium was loaded on to Streamliner Protein A column (XK 16/20 1.6 cm×10.0 cm) and pre-equilibrated with 3 column volumes of 20 mM Tris-HCl pH 7.0 at a flow rate of 5.0 ml/min. The column was washed with 3 column volumes of the same buffer and the TNFRII-Fc fusion protein was eluted with 7 column volumes of 40 mM sodium citrate pH 3.5. The eluted fusion protein was neutralized immediately with 1M Tris-HCl pH 8.0.

CHT® Hydroxyapatite type 140 μm resin (Bio-Rad Laboratories, Hercules, Calif., Cat #157-0040) was used as a second purification step. The Hydroxyapatite column was equilibrated with 3 column volumes of 5 mM sodium phosphate pH 6.5 and the Streamliner Protein A purified TNFRII-Fc fusion protein was buffer exchanged into the equilibration buffer and applied to the column. After loading, the column was washed with 3 column volumes of the equilibration buffer and elution was performed by developing a gradient over 20 column volumes ranging from 0 to 1000 mM sodium chloride. TNFRII-Fc fusion protein elutes around 550-650 mM sodium chloride. The pooled TNFRII-Fc fusion protein was sterile filtered using 0.2 μm Polyethersulfone (PES) membrane filter and stored at 4° C.

SDS-PAGE (4-20% Tris-HCl gels, Bio-Rad Laboratories, Hercules, Calif., Cat. #161-1123) was run for the two column purified TNFRII-Fc fusion protein fractions, transferred onto a polyvinylidene difluoride (PVDF) membrane (ProBlott™ Membranes, Applied Biosystems, Foster City, Calif., Cat #400994) at 55 volts for thirty minutes and stained with ProBlott stain (Applied Biosystems, Foster City, Calif.). Bands corresponding to TNFRII-Fc fusion protein were cut from the PVDF membrane and sent to Tufts Core Facility, Boston, Mass., for N-terminal sequencing.

Expression of a full length recombinant granulocyte colony-stimulating factor (GCSF) protein was carried out in a similar manner. However, instead of the GS5.0 host cell above that was used to express the TNFRII-Fc, the host cell used for expressing the GCSF was a *Pichia pastoris* GS2.0 host cell in which the STE13 and DAP2 genes had been disrupted following the process described in Example 3. GS2.0 host cells are host cells that have been genetically engineered to produce glycoproteins comprising Man$_5$GlcNAc$_2$ N-glycans. These strains are not capable of producing glycoproteins that have galactose-terminated N-glycans. Examples of such strains have been disclosed in Nett and Gerngross, Yeast 20:1279 (2003); Choi et al., Proc. Natl. Acad. Sci. USA 100:5022 (2003); and Hamilton et al., Science 301:1244 (2003). FIG. 6 shows that these host cells are capable of producing an intact GCSF when the STE13 and DAP2 genes were disrupted as described above for the GS5.0 strain expressing TNFRII-Fc (compare lanes 27-29 showing GCSF produced in STEI31/DAP2 strain to lanes 32-34 showing GCSF produced in an ste13/dap2 knock-out strain).

Example 5

Deletion of PpDppIIIp

Similarly, the methods described in the examples above to eliminate PpSte13p and PpDap2p can be used to eliminate PpDppIIIp. One such method would be to design a knockout vector in a manner similar to that provided for PpSTE13 and PpDAP2 in Example 2. Primers would be designed to amplify the 5' and 3' flanking regions of the PpDPPIII gene (FIG. 13, SEQ ID NO: 54), for an essential region of the genomic sequence, for example, a region required for functional PpDppIIIp activity is omitted. PpDppIIIp activity can be eliminated by combining these flanking regions with a selectable marker. In combination with compatible selectable markers, PpDppIIIp activity can be eliminated individually or in combination with the elimination of PpSte13p and/or PpDap2 activity. A strain in which PpSte13p, PpDap2p and PpDppIIIp activity has been eliminated would produce a strain devoid of any potential dipeptidyl aminopeptidase activity.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed:

1. A method for producing a recombinant protein having an X-P/A at the amino-terminus, wherein X is any amino acid and P/A is proline or alanine, in a *Pichia* host cell, wherein the recombinant protein is secreted into the host cell culture medium, in which STE13 and DAP2 has been deleted or disrupted, comprising:
   a. transforming the *Pichia* cell with a polynucleotide vector encoding the protein having the X-P/A at the amino-terminus;
   b. culturing the transformed *Pichia* cell in a medium under conditions which induce expression of the protein; and
   c. isolating the protein from the culture medium.

2. The method of claim 1 where the *Pichia* cell is *Pichia pastoris*.

3. The method of claim 1, wherein the host cell has been genetically engineered to produce glycoproteins comprising human-like N-glycans.

4. The method of claim 3, wherein the host cell wherein the human-like N-glycans are selected from the group consisting of hybrid and complex N-glycans.

5. The method of claim 1, wherein the host cell is genetically engineered to produce glycoproteins that have predominantly an N-glycan selected from $Man_5GlcNAc_2$, $GlcNAcMan_5GlcNAc_2$, $GalGlcNAcMan_5GlcNAc_2$, $NANAGalGlcNAcMan_5GlcNAc_2$, $GlcNAcMan_3GlcNAc_2$, $GlcNAc_{(1-4)}Man_3GlcNAc_2$, $Gal_{(1-4)}GlcNAc_{(1-4)}Man_3GlcNAc_2$, and $NANA_{(1-4)}Gal_{(1-4)}GlcNAc_{(1-4)}Man_3GlcNAc_2$.

6. The method of claim 1, wherein the *Pichia* expresses a human glycoprotein.

7. A genetically modified *Pichia* cell in which the genomic DNA encoding DPPIII, STE13 and DAP2 has been deleted or disrupted from the *Pichia* cell genome.

8. The *Pichia* cell of claim 7 which is *Pichia pastoris*.

9. The method of claim 5, wherein the host cell has been genetically engineered to produce glycoproteins comprising human-like N-glycans.

10. The method of claim 9, wherein the human-like N-glycans are selected from the group consisting of hybrid and complex N-glycans.

11. The method of claim 5, wherein the protein is a human glycoprotein.

12. The method of claim 1 wherein DPPIII, STE13 and DAP2 are deleted or disrupted in the host cell.

* * * * *